US007811588B2

(12) United States Patent
James et al.

(10) Patent No.: US 7,811,588 B2
(45) Date of Patent: Oct. 12, 2010

(54) MYCOBACTERIAL GENES DOWN-REGULATED DURING LATENCY

(75) Inventors: Brian William James, Salisbury (GB); Tobias Hampshire, Salisbury (GB); Philip Marsh, Salisbury (GB)

(73) Assignee: Health Protection Agency, Porton Down, Salisbury, Wiltshire (GB)

( * ) Notice: Subject to any disclaimer, the term of this patent is extended or adjusted under 35 U.S.C. 154(b) by 386 days.

(21) Appl. No.: 10/493,462

(22) PCT Filed: Oct. 21, 2002

(86) PCT No.: PCT/GB02/04718

§ 371 (c)(1),
(2), (4) Date: Aug. 12, 2004

(87) PCT Pub. No.: WO03/035681

PCT Pub. Date: May 1, 2003

(65) Prior Publication Data

US 2004/0253711 A1 Dec. 16, 2004

(30) Foreign Application Priority Data

Oct. 24, 2001 (GB) ................................ 0125535.5

(51) Int. Cl.
*A61K 39/04* (2006.01)
*A61K 39/02* (2006.01)
*A61K 39/00* (2006.01)
(52) U.S. Cl. ...................... 424/248.1; 424/9.1; 424/9.2; 424/184.1; 424/185.1; 424/190.1; 424/234.1; 435/4; 435/7.1; 435/7.2; 530/300; 530/350
(58) Field of Classification Search ................... 424/9.1, 424/9.2, 184.1, 185.1, 190.1, 234.1, 248.1; 435/4, 7.1, 7.2; 530/300, 350
See application file for complete search history.

(56) References Cited

U.S. PATENT DOCUMENTS

| | | | | |
|---|---|---|---|---|
| 6,573,361 B1 * | 6/2003 | Bunkers et al. | ............. | 530/324 |
| 6,583,266 B1 * | 6/2003 | Smith et al. | ................... | 530/350 |
| 6,892,139 B2 * | 5/2005 | Eisenberg et al. | ............. | 702/19 |
| 2004/0241826 A1 | 12/2004 | James et al. | | |
| 2004/0254349 A1 | 12/2004 | James et al. | | |

FOREIGN PATENT DOCUMENTS

| WO | WO 96/17951 A2 | | 6/1996 |
|---|---|---|---|
| WO | WO98/16645 | * | 4/1998 |

OTHER PUBLICATIONS

McMurray, D. Recent progress in the development and testing of vaccines against human tuberculosis. Internation Journal for Parasitology, vol. 33, pp. 547-554, 2003.*
von Reyn, C.F., et al. New vaccines for the prevention of tuberculosis. Clinical Infectious Diseases, Vo. 35, pp. 465-474, 2002.*
Orme, I.M., et al. Tuberculosis vaccine development: recent progress. Trends in Microbiology, vol. 9, No. 3, pp. 115-118, 2001.*
Honore, N., et al, "Nucleotide sequence of the first cosmid from the *Mycobacterium leprae* genome project: structure and function of the Rif—Str regions", Molecular Microbiology, vol. 7, No. 2, pp. 207-214, 1993.*
Ohara, N., et al, "Isolation and amino acid sequence of the 30S ribosomal protein S19 from *Mycobacterium bovis* BCG", FEBS Letters, vol. 331, No. 1,2, pp. 9-14, 1993.*
Cole, S.T., et al., "Deciphering the biology of *Mycobacterium tuberculosis* from the complete genome sequence," *Nature* 393:537-544 (with 10 sheets of Table 1. Functional classification of *Mycobacterium tuberculosis* protein coding genes), Macmillan Publishers Ltd. (1998).
Cole, S.T., et al., "Deciphering the biology of *Mycobacterium tuberculosis* from the complete genome sequence," Erratum in *Nature* 396:190-198, Macmillan Publishers Ltd. (1998).
Nutter, B. and Dick, T., "Up-regulation of *narX*, encoding a putative 'fused nitrate reductase' in anaerobic dormant *Mycobacterium bovis* BCG," *Fems Microbiol. Lett.* 178:63-69, Elsevier Science B.V. (1999).
Murugasu-Oei, B., et al., "Upregulation of stress response genes and ABC transporters in anaerobic stationary-phase *Mycobacterium smegmatis," Mol. Gen. Genet.* 262:677-682, Springer-Verlag (1999).
Sambrook, J., et al., "Construction and Analysis of cDNA Libraries," in *Molecular Cloning, A Laboratory Manual, 2nd Edition*, Cold Spring Harbor Laboratory Press, Cold Spring Harbor, NY, pp. 8.48-8.49 (1989).
Sherman, D.R. et al., "Regulation of the *Mycobacterium tuberculosis* hypoxic response gene encoding α-crystallin," *Proc. Natl. Acad. Sci. USA* 98:7534-7539, National Academy of Sciences (Jun. 19, 2001).
Talaat, A.M. et al., "Genome-directed primers for selective labeling of bacterial transcripts for DNA microarray analysis," *Nat. Biotechnol.* 18:679-682, Macmillan Publishers Ltd. (Jun. 2000).
EMBL Online Database Sequence, Accession No. O53607, "Putative cellulase of *Mycobacterium tuberculosis*," Created Jun. 1, 1998.
Daniel, T.M., "Soluble Mycobacterial Antigens," in *The Mycobacteria—A Sourcebook, Part A*, Kubica, G.P., and Wayne, L.G., eds., Marcel Dekker, Inc., New York, pp. 417-465 (1984).
Stedman's Medical Dictionary, 26th Edition, Williams & Wilkins, Baltimore, MD, p. 868 (1995).

(Continued)

*Primary Examiner*—Rodney P. Swartz
(74) *Attorney, Agent, or Firm*—Evan Law Group LLC

(57) ABSTRACT

A method is provided for identifying mycobacterial genes the expression of which is down-regulated during a stationary phase culture of mycobacteria under nutrient-starving conditions when compared with an exponential phase culture of mycobacteria under culture conditions that are not nutrient-starving and that support exponential growth of said mycobacteria. The described method optionally provides for identifying mycobacterial genes that are simultaneously down-regulated under low dissolved oxygen tension conditions. The down-regulated genes of the present invention form the basis of nucleic acid vaccines, or provide targets to allow preparation of attenuated mycobacteria for vaccines against mycobacterial infections. Similarly, peptides encoded by said down-regulated genes are employed in vaccines. In a further embodiment, the identified genes/peptides provide the means for identifying the presence of a mycobacterial infection in a clinical sample by nucleic acid probe or antibody detection.

6 Claims, 4 Drawing Sheets

OTHER PUBLICATIONS

Figure 1:
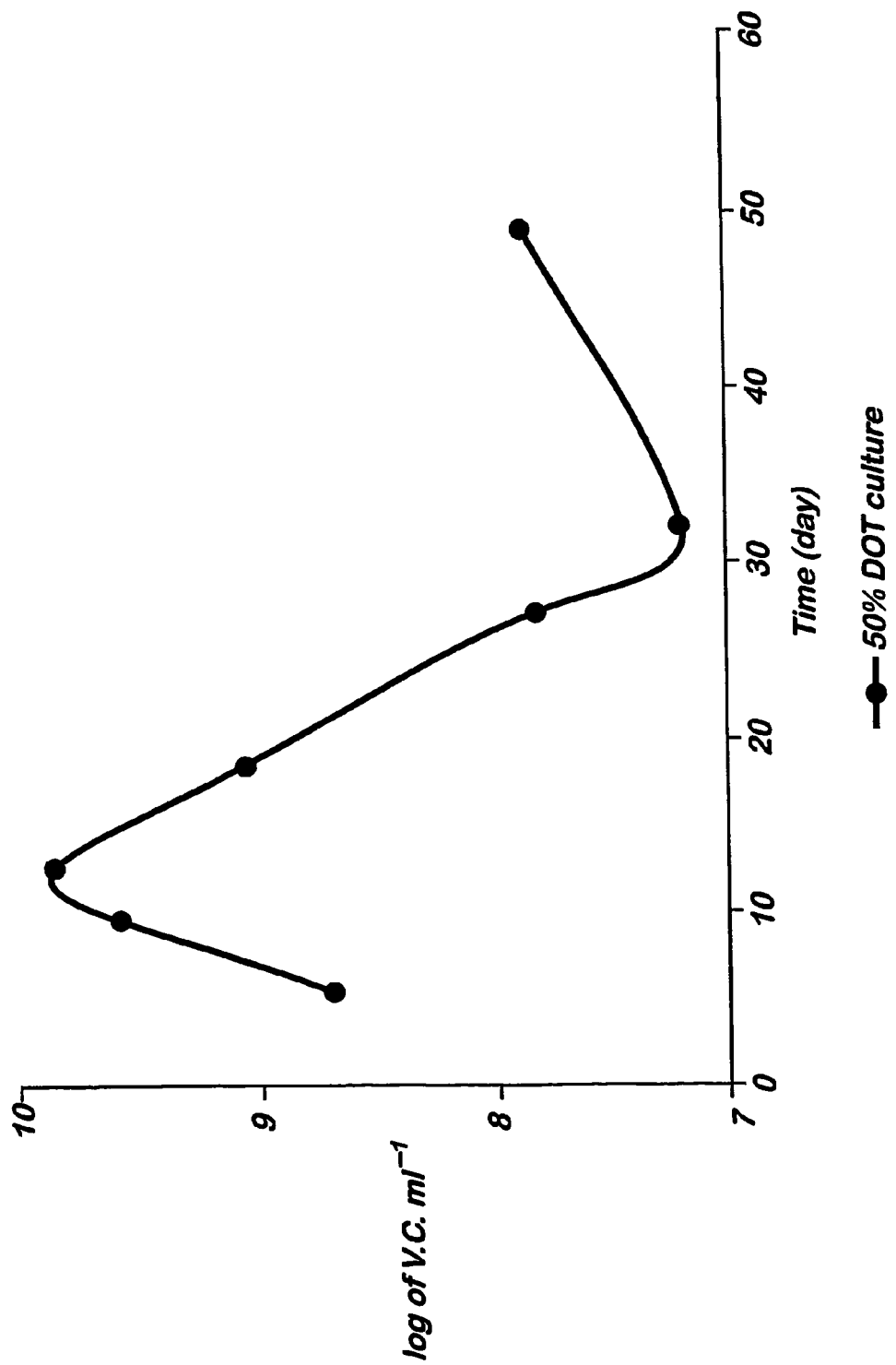

Ojha, A.K., et al., "High Intracellular Level of Guanosine Tetraphosphate in *Mycobacterium smegmatis* Changes the Morphology of the Bacterium," *Infection and Immunity* 68:4084-4091, American Society for Microbiology (2000).

Smeulders, M.J., et al., "Adaption of *Mycobacterium smegmatis* to Stationary Phase," *J.Bacteriol.* 181:270-283, American Society for Microbiology (1999).

Flynn, J.L. and Chan, J., "Tuberculosis: Latency and Reactivation," *Infect. Immun.* 69:4195-4201, American Society for Microbiology (Jul. 2001).

Ohno, H. and Kohno, S., "Trends in Research Concerning Pulmonary Myocobacteriosis Genome and Pathogenicity of Tuberculosis" *Resp. Molec. Med.* 6:202-209, Akira (May 2002).

Unverified English Language Translation of Document NPL6, Ohno, H. and Kohno, S., "Trends in Research Concerning Pulmonary Myocobacteriosis Genome and Pathogenicity of Tuberculosis," *Resp. Molec. Med.* 6:202-209, Akira (May 2002).

Wilson, M., et al., "Exploring drug-induced alterations in gene expression in *Mycobacterium tuberculosis* by microarray hybridization," *Proc. Natl. Acad. Sci. U.S.A.* 96:12833-12838, National Academy of Science (1999).

* cited by examiner

SEQUENCE LISTING

<160> NUMBER OF SEQ ID NOS: 46

<210> SEQ ID NO 1
<211> LENGTH: 380
<212> TYPE: PRT
<213> ORGANISM: Mycobacterium tuberculosis

<400> SEQUENCE: 1

Met Thr Arg Arg Thr Gly Gln Arg Trp Arg Gly Thr Leu Pro Gly Arg
1               5                   10                  15

Arg Pro Trp Thr Arg Pro Ala Pro Ala Thr Cys Arg Arg His Leu Ala
            20                  25                  30

Phe Val Glu Leu Arg His Tyr Phe Ala Arg Val Met Ser Ser Ala Ile
        35                  40                  45

Gly Ser Val Ala Arg Trp Ile Val Pro Leu Leu Gly Val Ala Ala Val

-continued

```
    50                  55                  60

Ala Ser Ile Gly Val Ile Ala Asp Pro Val Arg Val Val Arg Ala Pro
65                  70                  75                  80

Ala Leu Ile Leu Val Asp Ala Ala Asn Pro Leu Ala Gly Lys Pro Phe
                85                  90                  95

Tyr Val Asp Pro Ala Ser Ala Ala Met Val Ala Ala Arg Asn Ala Asn
            100                 105                 110

Pro Pro Asn Ala Glu Leu Thr Ser Val Ala Asn Thr Pro Gln Ser Tyr
        115                 120                 125

Trp Leu Asp Gln Ala Phe Pro Pro Ala Thr Val Gly Gly Thr Val Ala
    130                 135                 140

Arg Tyr Thr Gly Ala Ala Gln Ala Ala Gly Ala Met Pro Val Leu Thr
145                 150                 155                 160

Leu Tyr Gly Ile Pro His Arg Asp Cys Gly Ser Tyr Ala Ser Gly Gly
                165                 170                 175

Phe Ala Thr Gly Thr Asp Tyr Arg Gly Trp Ile Asp Ala Val Ala Ser
            180                 185                 190

Gly Leu Gly Ser Ser Pro Ala Thr Ile Ile Val Glu Pro Asp Ala Leu
        195                 200                 205

Ala Met Ala Asp Cys Leu Ser Pro Asp Gln Arg Gln Glu Arg Phe Asp
    210                 215                 220

Leu Val Arg Tyr Ala Val Asp Thr Leu Thr Arg Asp Pro Ala Ala Ala
225                 230                 235                 240

Val Tyr Val Asp Ala Gly His Ser Arg Trp Leu Ser Ala Glu Ala Met
                245                 250                 255

Ala Ala Arg Leu Asn Asp Val Gly Val Gly Arg Ala Arg Gly Phe Ser
            260                 265                 270

Leu Asn Val Ser Asn Phe Tyr Thr Thr Asp Glu Glu Ile Gly Tyr Gly
        275                 280                 285

Glu Ala Ile Ser Gly Leu Thr Asn Gly Ser His Tyr Val Ile Asp Thr
    290                 295                 300

Ser Arg Asn Gly Ala Gly Pro Ala Pro Asp Ala Pro Leu Asn Trp Cys
305                 310                 315                 320

Asn Pro Ser Gly Arg Ala Leu Gly Ala Pro Pro Thr Thr Ala Thr Ala
                325                 330                 335

Gly Ala His Ala Asp Ala Tyr Leu Trp Ile Lys Arg Pro Gly Glu Ser
            340                 345                 350

Asp Gly Thr Cys Gly Arg Gly Glu Pro Gln Ala Gly Arg Phe Val Ser
        355                 360                 365

Gln Tyr Ala Ile Asp Leu Ala His Asn Ala Gly Gln
    370                 375                 380

<210> SEQ ID NO 2
<211> LENGTH: 1140
<212> TYPE: DNA
<213> ORGANISM: Mycobacterium tuberculosis

<400> SEQUENCE: 2
atgacgcgtc ggactgggca gcgatggcgc gggactctgc ccgggcgccg gccttggaca      60
cggccagcgc ccgccacctg tcgtcggcat ttggcgtttg tcgaattgcg gcattatttt     120
gctcgggtga tgtcatcagc tattggttcg gtcgcgcggt ggatagtccc cctcctgggg     180
gttgcagccg ttgcttccat cggtgttatc gcggacccgg tgcgggtcgt tcgggccccg     240
gcgttgatcc tggtcgatgc ggcaaacccg ctggccggaa agcccttcta cgtcgatccc     300
```

```
gcctcggcgg ccatggtcgc cgcgcgcaac gccaacccgc cgaacgccga gctgacctcc    360
gtcgccaaca ccccgcagtc ctactggctc gaccaggcat tcccgccggc gaccgtcggc    420
ggcacggttg ccaggtacac cggagcggcg caggcggccg cgccatgcc ggttctgacg    480
ctgtatggaa tccccatcg cgactgcggt agctacgcat ccggtgggtt cgcgacgggc    540
actgattacc gcgggtggat cgacgctgtc gcatccggcc tgggctcatc gccggcgacg    600
atcatcgtcg aacccgatgc gctggccatg gccgactgcc tgtcgcctga ccagcgccag    660
gaacgtttcg acttggtgcg ctacgccgtc gacacgctga cccgcgaccc ggccgctgcc    720
gtgtacgtcg atgcggggca ttcgcgctgg ctgagcgccg aggcaatggc cgccaggctc    780
aacgatgtcg gtgtgggccg cgcgcgcggg tttagcctca acgtctcgaa cttctacacc    840
accgatgagg aaatcggcta tggcgaggcg atttcggggc tcacgaacgg ttcgcattac    900
gtgatcgaca cgtcgcgcaa cggcgccgga cccgcgcccg acgccccgct caactggtgt    960
aaccccagcg gccgcgccct gggcgcaccg cccaccacgg cgaccgcggg cgcgcacgcc   1020
gacgcttacc tgtggatcaa acgtcccggg gaatcggacg gaacctgcgg tcgcggggag   1080
cctcaggcgg gtcggttcgt tagccagtac gccatcgatc tggcccacaa cgccggccag   1140
```

<210> SEQ ID NO 3
<211> LENGTH: 417
<212> TYPE: PRT
<213> ORGANISM: Mycobacterium tuberculosis

<400> SEQUENCE: 3

```
Val Asn Leu Gln Leu Phe Leu Leu Ile Val Val Thr Ala Leu
1               5                   10                  15

Ala Phe Asp Phe Thr Asn Gly Phe His Asp Thr Gly Asn Ala Met Ala
            20                  25                  30

Thr Ser Ile Ala Ser Gly Ala Leu Ala Pro Arg Val Ala Val Ala Leu
        35                  40                  45

Pro Ala Val Leu Asn Leu Ile Gly Ala Phe Leu Ser Thr Ala Val Ala
    50                  55                  60

Ala Thr Ile Ala Lys Gly Leu Ile Asp Ala Asn Leu Val Thr Leu Glu
65                  70                  75                  80

Leu Val Phe Ala Gly Leu Val Gly Gly Ile Val Trp Asn Leu Leu Thr
                85                  90                  95

Trp Leu Leu Gly Ile Pro Ser Ser Ser His Ala Leu Ile Gly Gly
            100                 105                 110

Ile Val Gly Ala Thr Ile Ala Ala Val Gly Leu Arg Gly Val Ile Trp
        115                 120                 125

Ser Gly Val Val Ser Lys Val Ile Pro Ala Val Val Ala Ala Leu
    130                 135                 140

Leu Ala Thr Leu Val Gly Ala Val Gly Thr Trp Leu Val Tyr Arg Thr
145                 150                 155                 160

Thr Arg Gly Val Ala Glu Lys Arg Thr Glu Arg Gly Phe Arg Arg Gly
                165                 170                 175

Gln Ile Gly Ser Ala Ser Leu Val Ser Leu Ala His Gly Thr Asn Asp
            180                 185                 190

Ala Gln Lys Thr Met Gly Val Ile Phe Leu Ala Leu Met Ser Tyr Gly
        195                 200                 205

Ala Val Ser Thr Thr Ala Ser Val Pro Pro Leu Trp Val Ile Val Ser
    210                 215                 220
```

```
Cys Ala Val Ala Met Ala Ala Gly Thr Tyr Leu Gly Gly Trp Arg Ile
225                 230                 235                 240

Ile Arg Thr Leu Gly Lys Gly Leu Val Glu Ile Lys Pro Pro Gln Gly
            245                 250                 255

Met Ala Ala Glu Ser Ser Ala Ala Val Ile Leu Leu Ser Ala His
            260                 265                 270

Phe Gly Tyr Ala Leu Ser Thr Thr Gln Val Ala Thr Gly Ser Val Leu
        275                 280                 285

Gly Ser Gly Val Gly Lys Pro Gly Ala Glu Val Arg Trp Gly Val Ala
    290                 295                 300

Gly Arg Met Val Val Ala Trp Leu Val Thr Leu Pro Leu Ala Gly Leu
305                 310                 315                 320

Val Gly Ala Phe Thr Tyr Gly Leu Val His Phe Ile Gly Gly Tyr Pro
                325                 330                 335

Gly Ala Ile Leu Gly Phe Ala Leu Leu Trp Leu Thr Ala Thr Ala Ile
                340                 345                 350

Trp Leu Arg Ser Arg Arg Ala Pro Ile Asp His Thr Asn Val Asn Ala
            355                 360                 365

Asp Trp Glu Gly Asn Leu Thr Ala Gly Leu Glu Ala Gly Ala Gln Pro
    370                 375                 380

Leu Ala Asp Gln Arg Pro Pro Val Pro Ala Pro Pro Ala Pro Thr Pro
385                 390                 395                 400

Pro Pro Asn His Arg Ala Pro Gln Phe Gly Val Thr Thr Arg Asn Ala
                405                 410                 415

Pro

<210> SEQ ID NO 4
<211> LENGTH: 1251
<212> TYPE: DNA
<213> ORGANISM: Mycobacterium tuberculosis

<400> SEQUENCE: 4
gtgaaccttc agttgttcct tttgctcatt gtcgtcgtga cggcattggc gttcgacttc    60
accaacgggt tccacgacac cggaaacgcc atggcgacct cgattgccag cggcgccctg   120
gcaccgcggg tagcggtagc acttcctgcc gtgctgaacc tgatcggtgc gttttttgtcc   180 accgccgtgg cggccacaat cgccaagggt ctgatcgacg cgaatctggt gacgctggag   240
ttggtgttcg ccggcctggt cggcgggatc gtctggaacc tgttgacctg gttgctgggc   300
attccgtcga gttcctcaca tgcgctgatc ggcggcatcg tcggcgccac aattgccgcc   360
gtcggcctgc gtggggtgat ctggagcgga gtggtgtcca aggtgatcgt gccggccgtg   420
gtagccgcgc tgctggccac gctggtcgga gcagtcggca cctggctggt ctaccggacg   480
acgcgcgggg ttgccgaaaa gcgtacggaa cgcggtttcc ggcgcggcca gatcggctcg   540
gcgtcgctgg tctcgctggc gcacggcacc aacgacgcgc agaagacgat gggcgtgatc   600
ttcctggcgt tgatgtccta cggcgcggtc agcacgacgg catcggtgcc gccgctgtgg   660
gtgatcgtga gttgcgccgt ggccatggcc gccggtacct acctgggtgg ctggcgcatc   720
atccgcaccc taggcaaagg gctggtcgag atcaaaccac cgcagggtat ggccgccgag   780
tcgtcatcgg ccgccgtcat tctgttgtcc gcgcacttcg gctatgcgct gtccacaacg   840
caggtcgcga ccgggtccgt gctgggcagc ggcgtcggca gcccggcgc gaggtgcgc   900 tgggggggtag ccggccgcat ggtggtcgcg tggctggtga cgctccccgtt ggccgggctg   960 gtcggggcct tcacctacgg gctggtgcat ttcatcggtg gctaccccgg tgcgatcctc  1020
```

```
ggtttcgcac tgttgtggct gaccgccacc gccatctggc tgcggtcgcg cagggcgccg   1080
atcgaccaca ccaacgtcaa cgccgactgg gaaggcaacc tgacggccgg cctggaagcg   1140
ggtgcgcagc cgcttgcgga tcagaggccg ccggtgcctg caccgccggc tccgactccc   1200
ccaccgaacc accgagcacc acagttcggc gtcaccacga ggaacgcccc g            1251
```

<210> SEQ ID NO 5
<211> LENGTH: 231
<212> TYPE: PRT
<213> ORGANISM: Mycobacterium tuberculosis

<400> SEQUENCE: 5

```
Met Thr Ser Gln Thr Gly Val Arg Asp Glu Leu Leu His Ala Gly Val
1               5                   10                  15

Arg Leu Leu Asp Asp His Gly Pro Asp Ala Leu Gln Thr Arg Lys Val
            20                  25                  30

Ala Ala Ala Ala Gly Thr Ser Thr Met Ala Val Tyr Thr His Phe Gly
        35                  40                  45

Gly Met Arg Gly Leu Ile Ala Ala Ile Ala Glu Glu Gly Leu Arg Gln
    50                  55                  60

Phe Asp Val Ala Leu Thr Val Pro Gln Thr Ala Asp Pro Val Ala Asp
65                  70                  75                  80

Leu Leu Ala Ile Gly Thr Ala Tyr Arg Arg Tyr Ala Ile Glu Arg Pro
                85                  90                  95

His Met Tyr Arg Leu Met Phe Gly Ser Thr Ser Ala His Gly Ile Asn
            100                 105                 110

Val Pro Ala Arg Asp Val Leu Thr Leu Lys Val Ala Glu Ile Glu His
        115                 120                 125

Gln His Pro Ser Phe Ala His Val Val Arg Ala Val His Arg Cys Leu
    130                 135                 140

Leu Ala Gly Arg Phe Ala Thr Ala Leu Gly Ala Asp Asp Asp Thr Ala
145                 150                 155                 160

Ile Val Ala Thr Ala Ala Gln Phe Trp Ser Gln Ile His Gly Phe Val
                165                 170                 175

Met Leu Glu Leu Ala Gly Phe Tyr Gly Asp Arg Gly Ala Ala Val Glu
            180                 185                 190

Pro Val Leu Ala Ala Met Thr Val Asn Leu Leu Val Ala Leu Gly Asp
        195                 200                 205

Ser Pro Glu Arg Ala Gln Cys Ser Leu Arg Ala Glu Gln Thr Gln Lys
    210                 215                 220

Asn Thr Leu Gly Arg Ala Thr
225                 230
```

<210> SEQ ID NO 6
<211> LENGTH: 693
<212> TYPE: DNA
<213> ORGANISM: Mycobacterium tuberculosis

<400> SEQUENCE: 6

```
atgacctcgc agaccggtgt tcgcgacgag ctgctgcacg ccggcgtgcg actgctcgac   60
gatcacgggc ccgacgcgct gcagacccgc aaggtggccg ccgcagcagg cacctcgacg   120
atggcggtgt acacccattt cggcgggatg cgcggactga tcgccgccat agccgaagaa   180
gggctacgcc agttcgatgt cgcgctgacg gtcccgcaga ccgccgatcc ggtcgccgac   240
ctgctggcca tcggcaccgc ctaccggcgc tacgccatcg agcgcccgca catgtaccgg   300
```

```
ctaatgttcg gcagcaccag cgcacacggc atcaacgtgc cagcgcgcga cgtgttgacc      360
ctcaaggttg ccgagatcga acaccagcac cccagtttcg cgcatgtggt gcgagcggtg      420
caccggtgcc tgctggccgg ccggttcgcg accgcgcttg gagccgacga cgacacggca      480
atagttgcca ccgcggcgca gttttggtca cagatccacg gcttcgtgat gctcgagctg      540
gccggcttct acgcgatcg aggcgcggcc gtcgaaccgg tgctcgccgc gatgacggtg       600
aacctgcttg tcgcgctggg agattcaccc gagcgggcgc agtgttcgct acgggccgag      660
cagacgcaaa agaacacgct gggcagagct act                                   693
```

<210> SEQ ID NO 7
<211> LENGTH: 217
<212> TYPE: PRT
<213> ORGANISM: Mycobacterium tuberculosis
<400> SEQUENCE: 7

```
Met Ala Arg Lys Gly Ile Leu Gly Thr Lys Leu Gly Met Thr Gln Val
1               5                  10                  15

Phe Asp Glu Ser Asn Arg Val Val Pro Val Thr Val Val Lys Ala Gly
            20                  25                  30

Pro Asn Val Val Thr Arg Ile Arg Thr Pro Glu Arg Asp Gly Tyr Ser
        35                  40                  45

Ala Val Gln Leu Ala Tyr Gly Glu Ile Ser Pro Arg Lys Val Asn Lys
    50                  55                  60

Pro Leu Thr Gly Gln Tyr Thr Ala Ala Gly Val Asn Pro Arg Arg Tyr
65                  70                  75                  80

Leu Ala Glu Leu Arg Leu Asp Asp Ser Asp Ala Ala Thr Glu Tyr Gln
                85                  90                  95

Val Gly Gln Glu Leu Thr Ala Glu Ile Phe Ala Asp Gly Ser Tyr Val
            100                 105                 110

Asp Val Thr Gly Thr Ser Lys Gly Lys Gly Phe Ala Gly Thr Met Lys
        115                 120                 125

Arg His Gly Phe Arg Gly Gln Gly Ala Ser His Gly Ala Gln Ala Val
    130                 135                 140

His Arg Arg Pro Gly Ser Ile Gly Gly Cys Ala Thr Pro Ala Arg Val
145                 150                 155                 160

Phe Lys Gly Thr Arg Met Ala Gly Arg Met Gly Asn Asp Arg Val Thr
                165                 170                 175

Val Leu Asn Leu Leu Val His Lys Val Asp Ala Glu Asn Gly Val Leu
            180                 185                 190

Leu Ile Lys Gly Ala Val Pro Gly Arg Thr Gly Gly Leu Val Met Val
        195                 200                 205

Arg Ser Ala Ile Lys Arg Gly Glu Lys
    210                 215
```

<210> SEQ ID NO 8
<211> LENGTH: 651
<212> TYPE: DNA
<213> ORGANISM: Mycobacterium tuberculosis
<400> SEQUENCE: 8

```
atggcacgaa agggcattct cggtaccaag ctgggtatga cgcaggtatt cgacgaaagc      60
aacagagtag taccggtgac cgtggtcaag gccgggccca acgtggtaac ccgcatccgc     120
acgcccgaac gcgacggtta tagcgccgtg cagctggcct atggcgagat cagcccacgc     180
```

-continued

```
aaggtcaaca agccgctgac aggtcagtac accgccgccg gcgtcaaccc acgccgatac    240
ctggcggagc tgcggctgga cgactcggat gccgcgaccg agtaccaggt tgggcaagag    300
ttgaccgcgg agatcttcgc cgatggcagc tacgtcgatg tgacgggtac ctccaagggc    360
aaaggtttcg ccggcaccat gaagcggcac ggcttccgcg tcagggcgc cagtcacggt     420 gcccaggcgg tgcaccgccg tccgggctcc atcggcggat gtgccacgcc ggcgcgggtg    480
ttcaagggca cccggatggc cggcggatg ggcaatgacc gggtgaccgt tcttaacctt     540
ttggtgcata aggtcgatgc cgagaacggc gtgctgctga tcaagggtgc ggttcctggc    600
cgcaccggtg gactggtcat ggtccgcagt gcgatcaaac gaggtgagaa g             651
```

<210> SEQ ID NO 9
<211> LENGTH: 481
<212> TYPE: PRT
<213> ORGANISM: Mycobacterium tuberculosis

<400> SEQUENCE: 9

```
Met Pro Ser Pro Thr Val Thr Ser Pro Gln Val Ala Val Asn Asp Ile
1               5                   10                  15

Gly Ser Ser Glu Asp Phe Leu Ala Ala Ile Asp Lys Thr Ile Lys Tyr
            20                  25                  30

Phe Asn Asp Gly Asp Ile Val Glu Gly Thr Ile Val Lys Val Asp Arg
        35                  40                  45

Asp Glu Val Leu Leu Asp Ile Gly Tyr Lys Thr Glu Gly Val Ile Pro
    50                  55                  60

Ala Arg Glu Leu Ser Ile Lys His Asp Val Asp Pro Asn Glu Val Val
65                  70                  75                  80

Ser Val Gly Asp Glu Val Glu Ala Leu Val Leu Thr Lys Glu Asp Lys
                85                  90                  95

Glu Gly Arg Leu Ile Leu Ser Lys Lys Arg Ala Gln Tyr Glu Arg Ala
            100                 105                 110

Trp Gly Thr Ile Glu Ala Leu Lys Glu Lys Asp Glu Ala Val Lys Gly
        115                 120                 125

Thr Val Ile Glu Val Val Lys Gly Gly Leu Ile Leu Asp Ile Gly Leu
    130                 135                 140

Arg Gly Phe Leu Pro Ala Ser Leu Val Glu Met Arg Arg Val Arg Asp
145                 150                 155                 160

Leu Gln Pro Tyr Ile Gly Lys Glu Ile Glu Ala Lys Ile Ile Glu Leu
                165                 170                 175

Asp Lys Asn Arg Asn Asn Val Val Leu Ser Arg Arg Ala Trp Leu Glu
            180                 185                 190

Gln Thr Gln Ser Glu Val Arg Ser Glu Phe Leu Asn Asn Leu Gln Lys
        195                 200                 205

Gly Thr Ile Arg Lys Gly Val Val Ser Ser Ile Val Asn Phe Gly Ala
    210                 215                 220

Phe Val Asp Leu Gly Gly Val Asp Gly Leu Val His Val Ser Glu Leu
225                 230                 235                 240

Ser Trp Lys His Ile Asp His Pro Ser Glu Val Val Gln Val Gly Asp
                245                 250                 255

Glu Val Thr Val Glu Val Leu Asp Val Asp Met Asp Arg Glu Arg Val
            260                 265                 270

Ser Leu Ser Leu Lys Ala Thr Gln Glu Asp Pro Trp Arg His Phe Ala
        275                 280                 285

Arg Thr His Ala Ile Gly Gln Ile Val Pro Gly Lys Val Thr Lys Leu
```

```
                290                 295                 300
Val Pro Phe Gly Ala Phe Val Arg Val Glu Gly Ile Glu Gly Leu
305                 310                 315                 320

Val His Ile Ser Glu Leu Ala Glu Arg His Val Glu Val Pro Asp Gln
                325                 330                 335

Val Val Ala Val Gly Asp Asp Ala Met Val Lys Val Ile Asp Ile Asp
                340                 345                 350

Leu Glu Arg Arg Arg Ile Ser Leu Ser Leu Lys Gln Ala Asn Glu Asp
                355                 360                 365

Tyr Thr Glu Glu Phe Asp Pro Ala Lys Tyr Gly Met Ala Asp Ser Tyr
370                 375                 380

Asp Glu Gln Gly Asn Tyr Ile Phe Pro Glu Gly Phe Asp Ala Glu Thr
385                 390                 395                 400

Asn Glu Trp Leu Glu Gly Phe Glu Lys Gln Arg Ala Glu Trp Glu Ala
                405                 410                 415

Arg Tyr Ala Glu Ala Glu Arg Arg His Lys Met His Thr Ala Gln Met
                420                 425                 430

Glu Lys Phe Ala Ala Ala Glu Ala Ala Gly Arg Gly Ala Asp Asp Gln
                435                 440                 445

Ser Ser Ala Ser Ser Ala Pro Ser Glu Lys Thr Ala Gly Gly Ser Leu
450                 455                 460

Ala Ser Asp Ala Gln Leu Ala Ala Leu Arg Glu Lys Leu Ala Gly Ser
465                 470                 475                 480

Ala

<210> SEQ ID NO 10
<211> LENGTH: 1443
<212> TYPE: DNA
<213> ORGANISM: Mycobacterium tuberculosis

<400> SEQUENCE: 10
atgccgagtc ccaccgtcac ctcgccgcaa gtagccgtca cgacataggc tctagcgag      60 gactttctcg ccgcaataga caaaacgatc aagtacttca cgatggcga catcgtcgaa     120 ggcaccatcg tcaaagtgga ccgggacgag gtgctcctcg acatcggcta caagaccgaa    180
ggcgtgatcc ccgcccgcga actgtccatc aagcacgacg tcgaccccaa cgaggtcgtt    240
tccgtcggtg acgaggtcga agccctggtg ctcaccaagg aggacaaaga gggccggctc    300
atcctctcca gaaacgcgc gcagtacgag cgtgcctggg gcaccatcga ggcgctcaag    360
gagaaggacg aggccgtcaa gggcacggtc atcgaggtcg tcaagggtgg cctgatcctc    420
gacatcgggc tgcgcggttt cctgcccgcc tcgctggtgg agatgcgccg ggtgcgcgac    480
ctgcagccct acatcggcaa ggagatcgag gccaagatca tcgagctgga caagaaccgc    540
aacaacgtgg tgctgtcccg tcgcgcctgg ctggagcaga cccagtccga ggtgcgcagc    600
gagttcctga ataacttgca aaaaggcacc atccgaaagg gtgtcgtgtc ctcgatcgtc    660
aacttcggcg cgttcgtcga ctcggcggt gtggacggtc tggtgcatgt ctccgagcta    720
tcgtggaagc acatcgacca cccgtccgag gtggtccagg ttggtgacga ggtcaccgtc    780
gaggtgctcg acgtcgacat ggaccgtgag cgggtttcgt tgtcactcaa ggcgactcag    840
gaagacccgt ggcggcactt cgcccgcact cacgcgatcg gcagatcgt gccgggcaag    900 gtcaccaagt tggttccgtt cggtgcattc gtccgcgtcg aggagggtat cgagggcctg    960
gtgcacatct ccgagctggc cgagcgtcac gtcgaggtgc ccgatcaggt ggttgccgtc   1020
```

-continued

```
ggcgacgacg cgatggtcaa ggtcatcgac atcgacctgg agcgccgtcg gatctcgttg      1080
tcgctcaagc aagccaatga ggactacacc gaggagttcg acccggcgaa gtacggcatg      1140
gccgacagtt acgacgagca gggcaactac atcttccccg agggcttcga tgccgaaacc      1200
aacgaatggc ttgagggatt cgaaaagcag cgcgccgaat gggaagctcg gtacgccgag      1260
gccgagcgcc ggcacaagat gcacaccgcg cagatggaga agttcgccgc cgccgaggcg      1320
gctggacgcg gcgcggacga tcagtcgtcg gccagtagcg caccgtcgga aaagaccgcg      1380
ggtggatcac tggccagcga cgcccagctg gcggccctgc gggaaaaact cgccggcagc      1440
gct                                                                   1443
```

<210> SEQ ID NO 11
<211> LENGTH: 380
<212> TYPE: PRT
<213> ORGANISM: Mycobacterium tuberculosis

<400> SEQUENCE: 11

```
Leu Asp Thr Val Leu Gly Leu Ser Ile Thr Pro Thr Thr Leu Gly Trp
 1               5                  10                  15

Val Leu Ala Glu Gly His Gly Ala Asp Gly Ala Ile Leu Asp Arg Asn
            20                  25                  30

Glu Leu Glu Leu His Ser Gly Arg Asn Ala Gln Ala Ile His Thr Ala
        35                  40                  45

Glu Gln Leu Ala Ala Glu Val Leu Ala His Glu Val Ala Ala Ala
    50                  55                  60

Gly Asp His Arg Leu Arg Val Ile Gly Val Thr Trp Asn Ala Glu Ala
65                  70                  75                  80

Ser Ala Gln Ala Ala Leu Leu Val Glu Ser Leu Thr Gly Ala Gly Phe
                85                  90                  95

Asp Asn Val Val Pro Val Arg Arg Leu Arg Ala Ile Glu Thr Leu Ala
            100                 105                 110

Gln Ala Ile Ala Pro Val Ile Gly Tyr Glu Gln Ile Ala Val Cys Val
        115                 120                 125

Leu Glu His Glu Ser Ala Thr Val Val Met Val Asp Thr His Asp Gly
    130                 135                 140

Lys Thr Gln Ile Ala Val Lys His Val Cys Arg Gly Leu Ser Gly Leu
145                 150                 155                 160

Thr Ser Trp Leu Thr Gly Met Phe Gly Arg Asp Ala Trp Arg Pro Ala
                165                 170                 175

Gly Val Val Val Gly Ser Asp Ser Glu Val Ser Glu Phe Ser Trp
            180                 185                 190

Gln Leu Glu Arg Val Leu Pro Val Pro Val Phe Ala Gln Thr Met Ala
        195                 200                 205

Gln Val Thr Val Ala Arg Gly Ala Ala Leu Ala Ala Gln Ser Thr
    210                 215                 220

Glu Phe Thr Asp Ala Gln Leu Val Ala Asp Ser Val Ser Gln Pro Thr
225                 230                 235                 240

Val Ala Pro Arg Arg Ser Arg His Tyr Ala Gly Ala Ala Ala Leu
                245                 250                 255

Ala Ala Ala Ala Val Thr Phe Val Ala Ser Leu Ser Leu Ala Val Gly
            260                 265                 270

Ile Gln Leu Ala Pro His Asn Asp Thr Gly Thr Ala Lys His Gly Ala
        275                 280                 285

His Lys Pro Thr Pro Arg Ile Ala Lys Ala Val Ala Pro Ala Val Pro
```

```
                    290                 295                 300
Pro Pro Pro Thr Val Thr Pro Val Pro Ala Arg Ala Pro Arg Pro
305                 310                 315                 320

Ala Ala Gln His Glu Pro Pro Ala Arg Val Thr Ser Gly Glu Ala Leu
                325                 330                 335

Thr Glu Pro Asn Pro Pro Glu Glu Gln Pro Asn Ala Ser Ala Pro Gln
            340                 345                 350

Gln Asp Arg Asn Asp Ser Gln Pro Ile Thr Arg Val Leu Glu His Ile
        355                 360                 365

Pro Gly Ala Tyr Gly Asp Ser Ala Pro Pro Ala Glu
    370                 375                 380

<210> SEQ ID NO 12
<211> LENGTH: 1140
<212> TYPE: DNA
<213> ORGANISM: Mycobacterium tuberculosis

<400> SEQUENCE: 12
ttggacacgg tacttgggct ctcgataacg cctaccaccc tggggtgggt cctcgctgaa      60
ggacacggcg cagacggcgc catcttggac cgcaacgaat ggagctaca tagcggtcgt     120 aacgcgcagg ccatacatac cgcagagcag ctggcggcgg aagttctgct cgcccatgaa    180
gtggccgctg caggcgatca tcggttgcgc gtcatcggag tgacctggaa cgccgaagct    240
tcggctcagg cggcgctgct ggtagagtcg ctgaccggtg caggtttcga caatgtggtg    300
ccggttcggc ggctacgtgc catcgagaca ctggcgcagg ctatcgcacc cgttatcggc    360
tacgagcaaa tcgcggtatg cgttcttgag catgagtcgg cgaccgtcgt catggtcgac    420
acccacgacg gaaagacgca gatcgccgtc aagcatgtgt gccgcggatt atcaggactg    480
acctcctggc tgaccggcat gtttggtcgc gatgcctggc gcccggccgg cgtggtcgtg    540
gtcggctcgg atagcgaggt cagcgaattc tcgtggcagc tcgaaagggt cctgccggtg    600
ccggtctttg cgcaaacgat ggcgcaggtt acggtcgcgc ggggtgcggc cctggcggcg    660
gcccagagca ccgagttcac cgatgcgcag ctagtggccg acagcgtcag ccaaccaacg    720
gtcgcgccca ggcgatcccg gcactacgcc ggggcggcgg cagcgttggc cgccgcggcc    780
gtgaccttcg tggcttcgct gtccctagcg gtgggcatcc agctggctcc gcacaacgat    840
accgggacgg cgaagcacgg agcgcacaag ccgacgccac gtatcgcaaa ggccgtggcg    900
ccggcggtgc cgcctccgcc gacggtcacg ccaccagtcc ctgctcgggc accccggccg    960
gctgcgcagc acgaaccacc cgctcgcgtc acctccggcg aagcgctcac ggagccgaac   1020
ccgcctgagg agcaaccgaa tgcttctgcg ccgcaacagg atcggaatga cagccagccg   1080
atcactcgag tgctagagca catacccggc gcttacggtg actcggcacc cccagctgag   1140

<210> SEQ ID NO 13
<211> LENGTH: 118
<212> TYPE: PRT
<213> ORGANISM: Mycobacterium tuberculosis

<400> SEQUENCE: 13

Met Leu Ile Ile Ala Leu Val Leu Ala Leu Ile Gly Leu Leu Ala Leu
1               5                   10                  15

Val Phe Ala Val Val Thr Ser Asn Gln Leu Val Ala Trp Val Cys Ile
                20                  25                  30

Gly Ala Ser Val Leu Gly Val Ala Leu Leu Ile Val Asp Ala Leu Arg
            35                  40                  45
```

```
Glu Arg Gln Gln Gly Gly Ala Asp Glu Ala Asp Gly Ala Gly Glu Thr
    50                  55                  60

Gly Val Ala Glu Glu Ala Asp Val Asp Tyr Pro Glu Glu Ala Pro Glu
 65                 70                  75                  80

Glu Ser Gln Ala Val Asp Ala Gly Val Ile Gly Ser Glu Glu Pro Ser
                85                  90                  95

Glu Glu Ala Ser Glu Ala Thr Glu Glu Ser Ala Val Ser Ala Asp Arg
            100                 105                 110

Ser Asp Asp Ser Ala Lys
        115

<210> SEQ ID NO 14
<211> LENGTH: 354
<212> TYPE: DNA
<213> ORGANISM: Mycobacterium tuberculosis

<400> SEQUENCE: 14
atgctgatca ttgcgctggt cttggccctg attgggctcc tggccttggt gttcgcggtg      60
gtcaccagca accagctagt ggcctgggta tgcatcgggg ccagcgtgct gggtgtggcg     120
ttgctgatcg tcgatgcgtt gcgagaacgc cagcaaggtg gcgcggacga agctgatggg     180
gctggggaaa cgggtgtcgc ggaggaagcc gacgtcgact accccggagga agcccccgag     240 gagagccaag ccgtcgacgc cggtgtcatc ggcagtgagg agccatcgga ggaggccagc     300
gaagcgaccg aggagtcggc ggtatcggcg gaccgaagcg acgacagcgc caag           354

<210> SEQ ID NO 15
<211> LENGTH: 143
<212> TYPE: PRT
<213> ORGANISM: Mycobacterium tuberculosis

<400> SEQUENCE: 15

Met Thr Ala Pro Ala Ser Leu Pro Ala Pro Leu Ala Glu Val Val Ser
 1               5                   10                  15

Asp Phe Ala Glu Val Gln Gly Gln Asp Lys Leu Arg Leu Leu Leu Glu
            20                  25                  30

Phe Ala Asn Glu Leu Pro Ala Leu Pro Ser His Leu Ala Glu Ser Ala
        35                  40                  45

Met Glu Pro Val Pro Glu Cys Gln Ser Pro Leu Phe Leu His Val Asp
    50                  55                  60

Ala Ser Asp Pro Asn Arg Val Arg Leu His Phe Ser Pro Ala Glu
 65                 70                  75                  80

Ala Pro Thr Thr Arg Gly Phe Ala Ser Ile Leu Ala Ala Gly Leu Asp
                85                  90                  95

Glu Gln Pro Ala Ala Asp Ile Leu Ala Val Pro Glu Asp Phe Tyr Thr
            100                 105                 110

Glu Leu Gly Leu Ala Ala Leu Ile Ser Pro Leu Arg Leu Arg Gly Met
        115                 120                 125

Ser Ala Met Leu Ala Arg Ile Lys Arg Arg Leu Arg Glu Ala Asp
    130                 135                 140

<210> SEQ ID NO 16
<211> LENGTH: 429
<212> TYPE: DNA
<213> ORGANISM: Mycobacterium tuberculosis

<400> SEQUENCE: 16
```

-continued

```
atgaccgcgc cgcgagcct gcccgcgccg ctagcagagg tggtatccga cttcgccgaa      60
gtccagggtc aagacaagct gaggctgttg ctggaattcg ccaacgagct gccggcgctt    120
ccgtcgcacc tggccgagtc cgctatggag ccggtccccg agtgccagtc tccgctgttt    180
ttgcacgtcg acgcgagtga ccccaaccgg gtgcgcctgc atttcagcgc gccggccgaa    240
gcgccaacca cgcgcgggtt cgcctcgatc ctggccgccg gcctagacga gcaaccggcc    300
gccgacatct tggcggtgcc cgaggatttc tacaccgagc tgggtctggc tgccttgatc    360
agcccactgc ggttgcgggg aatgtcggcg atgctggccc ggatcaagcg ccggctgcgc    420
gaagcggac                                                            429
```

<210> SEQ ID NO 17
<211> LENGTH: 201
<212> TYPE: PRT
<213> ORGANISM: Mycobacterium tuberculosis

<400> SEQUENCE: 17

Met Ala Arg Tyr Thr Gly Pro Val Thr Arg Lys Ser Arg Arg Leu Arg
1               5                   10                  15

Thr Asp Leu Val Gly Gly Asp Gln Ala Phe Glu Lys Arg Pro Tyr Pro
            20                  25                  30

Pro Gly Gln His Gly Arg Ala Arg Ile Lys Glu Ser Glu Tyr Leu Leu
        35                  40                  45

Gln Leu Gln Glu Lys Gln Lys Ala Arg Phe Thr Tyr Gly Val Met Glu
    50                  55                  60

Lys Gln Phe Arg Arg Tyr Tyr Glu Glu Ala Val Arg Gln Pro Gly Lys
65                  70                  75                  80

Thr Gly Glu Glu Leu Leu Lys Ile Leu Glu Ser Arg Leu Asp Asn Val
                85                  90                  95

Ile Tyr Arg Ala Gly Leu Ala Arg Thr Arg Arg Met Ala Arg Gln Leu
            100                 105                 110

Val Ser His Gly His Phe Asn Val Asn Gly Val His Val Asn Val Pro
        115                 120                 125

Ser Tyr Arg Val Ser Gln Tyr Asp Ile Val Asp Val Arg Asp Lys Ser
    130                 135                 140

Leu Asn Thr Val Pro Phe Gln Ile Ala Arg Glu Thr Ala Gly Glu Arg
145                 150                 155                 160

Pro Ile Pro Ser Trp Leu Gln Val Val Gly Glu Arg Gln Arg Val Leu
                165                 170                 175

Ile His Gln Leu Pro Glu Arg Ala Gln Ile Asp Val Pro Leu Thr Glu
            180                 185                 190

Gln Leu Ile Val Glu Tyr Tyr Ser Lys
        195                 200

<210> SEQ ID NO 18
<211> LENGTH: 603
<212> TYPE: DNA
<213> ORGANISM: Mycobacterium tuberculosis

<400> SEQUENCE: 18

```
atggctcgtt acaccggacc cgtcacccgc aaatcacggc ggttgcgcac cgacctcgtc     60
ggtggcgacc aggccttcga gaagcgtccc tacccgcccg ccaacacgg tcgcgcgcgg    120 atcaaggaaa gcgaatatct gcttcagctg caggagaagc agaaggcccg tttcacatac    180
ggcgtaatgg aaaagcagtt ccgccgctac tacgaagagg ccgtgcggca gcccggcaag    240
```

```
acgggtgaag aactgctgaa gatcctcgaa agccggctgg acaacgtcat ctaccgtgcc   300
gggctggcgc gcacccggcg gatggctcgc cagctggtca gccacgggca tttcaacgtc   360
aacggcgtgc acgtcaacgt ccccagttac cgggtgtcgc agtacgacat cgtcgacgtg   420
cgggacaagt ccctgaacac ggtgccgttc cagattgccc gggagacggc gggcgagcgt   480
ccgatcccga gctggctgca agtggtgggg gagcggcaac gcgtcctgat ccaccagcta   540
cccgagcgcg cgcagatcga cgtcccactc accgagcagc tgatcgtcga gtactactca   600
aag                                                                 603
```

```
<210> SEQ ID NO 19
<211> LENGTH: 393
<212> TYPE: PRT
<213> ORGANISM: Mycobacterium tuberculosis

<400> SEQUENCE: 19
```

Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
50                  55                  60

Leu Met Ala Ala Ala Ser Pro Tyr Val Ala Trp Met Ser Val Thr
65                  70                  75                  80

Ala Gly Gln Ala Gln Leu Thr Ala Ala Gln Val Arg Val Ala Ala
                85                  90                  95

Ala Tyr Glu Thr Ala Tyr Arg Leu Thr Val Pro Pro Val Ile Ala
            100                 105                 110

Glu Asn Arg Thr Glu Leu Met Thr Leu Thr Ala Thr Asn Leu Leu Gly
            115                 120                 125

Gln Asn Thr Pro Ala Ile Glu Ala Asn Gln Ala Ala Tyr Ser Gln Met
    130                 135                 140

Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
        195                 200                 205

Gln Gln Leu Ala Gln Pro Ala Gln Gly Val Val Pro Ser Ser Lys Leu
    210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
            260                 265                 270

Ala Ala Gln Ala Val Glu Thr Ala Ala Glu Asn Gly Val Trp Ala Met
        275                 280                 285

Ser Ser Leu Gly Ser Gln Leu Gly Ser Ser Leu Gly Ser Ser Gly Leu
    290                 295                 300

```
Gly Ala Gly Val Ala Ala Asn Leu Gly Arg Ala Ala Ser Val Gly Ser
305                 310                 315                 320

Leu Ser Val Pro Pro Ala Trp Ala Ala Asn Gln Ala Val Thr Pro
            325                 330                 335

Ala Ala Arg Ala Leu Pro Leu Thr Ser Leu Thr Ser Ala Ala Gln Thr
            340                 345                 350

Ala Pro Gly His Met Leu Gly Gly Leu Pro Leu Gly His Ser Val Asn
        355                 360                 365

Ala Gly Ser Gly Ile Asn Asn Ala Leu Arg Val Pro Ala Arg Ala Tyr
        370                 375                 380

Ala Ile Pro Arg Thr Pro Ala Ala Gly
385                 390
```

<210> SEQ ID NO 20
<211> LENGTH: 1179
<212> TYPE: DNA
<213> ORGANISM: Mycobacterium tuberculosis

<400> SEQUENCE: 20

```
gtggtggatt tcggggcgtt accaccggag atcaactccg cgaggatgta cgccggcccg      60
ggttcggcct cgctggtggc cgccgcgaag atgtgggaca gcgtggcgag tgacctgttt     120
tcggccgcgt cggcgtttca gtcggtggtc tgggtctga cggtggggtc gtggataggt     180
tcgtcggcgg gtctgatggc ggcggcggcc tcgccgtatg tggcgtggat gagcgtcacc     240
gcggggcagg cccagctgac cgccgcccag gtccgggttg ctgcggcggc ctacgagaca     300
gcgtataggc tgacggtgcc cccgccggtg atcgccgaga accgtaccga actgatgacg     360
ctgaccgcga ccaacctctt ggggcaaaac acgccggcga tcgaggccaa tcaggccgca     420
tacagccaga tgtggggcca agacgcggag gcgatgtatg gctacgccgc cacggcggcg     480
acggcgaccg aggcgttgct gccgttcgag gacgccccac tgatcaccaa ccccggcggg     540
ctccttgagc aggccgtcgc ggtcgaggag gccatcgaca ccgccgcggc gaaccagttg     600
atgaacaatg tgccccaagc gctgcaacag ctggcccagc cagcgcaggg cgtcgtacct     660
tcttccaagc tgggtgggct gtggacggcg gtctcgccgc atctgtcgcc gctcagcaac     720
gtcagttcga tagccaacaa ccacatgtcg atgatgggca cggtgtgtc gatgaccaac     780
accttgcact cgatgttgaa gggcttagct ccggcggcgg ctcaggccgt ggaaaccgcg     840
gcggaaaacg gggtctgggc gatgagctcg ctgggcagcc agctggggtc gtcgctgggt     900
tcttcgggtc tgggcgctgg ggtggccgcc aacttgggtc gggcggcctc ggtcggttcg     960
ttgtcggtgc cgccagcatg ggccgcggcc aaccaggcgg tcaccccggc ggcgcgggcg    1020
ctgccgctga ccagcctgac cagcgccgcc caaaccgccc ccggacacat gctgggcggg    1080
ctaccgctgg ggcactcggt caacgccggc agcggtatca acaatgcgct gcgggtgccg    1140
gcacgggcct acgcgatacc ccgcacaccg gccgccgga                           1179
```

<210> SEQ ID NO 21
<211> LENGTH: 565
<212> TYPE: PRT
<213> ORGANISM: Mycobacterium tuberculosis

<400> SEQUENCE: 21

```
Met Thr Arg Gly Arg Lys Pro Arg Pro Gly Arg Ile Val Phe Val Gly
1               5                   10                  15

Ser Gly Pro Gly Asp Pro Gly Leu Leu Thr Thr Arg Ala Ala Ala Val
            20                  25                  30
```

```
Leu Ala Asn Ala Ala Leu Val Phe Thr Asp Pro Asp Val Pro Glu Pro
             35                  40                  45

Val Val Ala Leu Ile Gly Thr Asp Leu Pro Val Ser Gly Pro Ala
 50                  55                  60

Pro Ala Glu Pro Val Ala Gly Asn Gly Asp Ala Ala Gly Gly Gly Ser
 65                  70                  75                  80

Ala Gln Glu His Gly Arg Ala Ser Ala Val Val Ser Gly Gly Pro
             85                  90                  95

Asp Ile Arg Pro Ala Leu Gly Asp Pro Ala Asp Val Ala Lys Thr Leu
             100                 105                 110

Thr Ala Glu Ala Arg Ser Gly Val Asp Val Val Arg Leu Val Ala Gly
             115                 120                 125

Asp Pro Leu Thr Val Asp Ala Val Ile Ser Glu Val Asn Ala Val Ala
             130                 135                 140

Arg Thr His Leu His Ile Glu Ile Val Pro Gly Leu Ala Ala Ser Ser
145                 150                 155                 160

Ala Val Pro Thr Tyr Ala Gly Leu Pro Leu Gly Ser Ser His Thr Val
                 165                 170                 175

Ala Asp Val Arg Ile Asp Pro Glu Asn Thr Asp Trp Asp Ala Leu Ala
             180                 185                 190

Ala Ala Pro Gly Pro Leu Ile Leu Gln Ala Thr Ala Ser His Leu Ala
             195                 200                 205

Glu Ser Ala Arg Ser Leu Ile Asp His Gln Leu Ala Glu Ser Thr Pro
 210                 215                 220

Cys Val Val Thr Ala His Gly Thr Thr Cys Gln Gln Arg Ser Val Glu
225                 230                 235                 240

Thr Thr Leu Gln Gly Leu Thr Asp Pro Ala Val Leu Gly Ala Thr Asp
                 245                 250                 255

Pro Ala Cys Ser Ala Asn Gly Arg Asp Ser Gln Ala Gly Pro Leu Ile
             260                 265                 270

Val Thr Ile Gly Lys Thr Val Thr Ser Arg Ala Lys Leu Asn Trp Trp
             275                 280                 285

Glu Ser Arg Ala Leu Tyr Gly Trp Thr Val Leu Val Pro Arg Thr Lys
 290                 295                 300

Asp Gln Ala Gly Glu Met Ser Glu Arg Leu Thr Ser Tyr Gly Ala Leu
305                 310                 315                 320

Pro Val Glu Val Pro Thr Ile Ala Val Glu Pro Pro Arg Ser Pro Ala
                 325                 330                 335

Gln Met Glu Arg Ala Val Lys Gly Leu Val Asp Gly Arg Phe Gln Trp
             340                 345                 350

Ile Val Phe Thr Ser Thr Asn Ala Val Arg Ala Val Trp Glu Lys Phe
             355                 360                 365

Gly Glu Phe Gly Leu Asp Ala Arg Ala Phe Ser Gly Val Lys Ile Ala
             370                 375                 380

Cys Val Gly Glu Ser Thr Ala Asp Arg Val Arg Ala Phe Gly Ile Ser
385                 390                 395                 400

Pro Glu Leu Val Pro Ser Gly Glu Gln Ser Ser Leu Gly Leu Leu Asp
                 405                 410                 415

Asp Phe Pro Pro Tyr Asp Ser Val Phe Asp Pro Val Asn Arg Val Leu
             420                 425                 430

Leu Pro Arg Ala Asp Ile Ala Thr Glu Thr Leu Ala Glu Gly Leu Arg
             435                 440                 445
```

```
Glu Arg Gly Trp Glu Ile Glu Asp Val Thr Ala Tyr Arg Thr Val Arg
    450                 455                 460

Ala Ala Pro Pro Ala Thr Thr Arg Glu Met Ile Lys Thr Gly Gly
465                 470                 475                 480

Phe Asp Ala Val Cys Phe Thr Ser Ser Thr Val Arg Asn Leu Val
                485                 490                 495

Gly Ile Ala Gly Lys Pro His Ala Arg Thr Ile Ala Cys Ile Gly
                500                 505                 510

Pro Lys Thr Ala Glu Thr Ala Ala Glu Phe Gly Leu Arg Val Asp Val
        515                 520                 525

Gln Pro Asp Thr Ala Ala Ile Gly Pro Leu Val Asp Ala Leu Ala Glu
    530                 535                 540

His Ala Ala Arg Leu Arg Ala Glu Gly Ala Leu Pro Pro Pro Arg Lys
545                 550                 555                 560

Lys Ser Arg Arg Arg
            565

<210> SEQ ID NO 22
<211> LENGTH: 1695
<212> TYPE: DNA
<213> ORGANISM: Mycobacterium tuberculosis

<400> SEQUENCE: 22
```

| | | |
|---|---|---|
| atgacgcgag ggcgtaagcc gagaccgggc cgcatcgttt tcgtgggctc cggtccgggc | 60 |
| gaccccggct tgcttacgac acgggctgcc gcggtgctgg ccaacgccgc gctggtgttc | 120 |
| accgatcccg acgtaccgga gccggtggtg cgcctgatcg gcacggatct gccccccgtg | 180 |
| tccggcccgg cgcccgccga gccggttgcc gggaacggcg atgcggccgg cggaggaagt | 240 |
| gcgcaggaac acggccgggc cgcgtccgcg gtagtctccg gtggtcctga catccgcccg | 300 |
| gcgctgggcg atcccgccga tgtggccaag acgctgaccg ccgaggcccg ttcgggtgtc | 360 |
| gacgtggtgc ggctggtggc gggcgatccg ctcacggtgg atgcggtaat cagcgaggtg | 420 |
| aacgccgtcg cacgcaccca cctgcacatc gaaatcgtgc cggcctggc cgccagcagc | 480 |
| gcggtcccga cctatgccgg gttgccgctg ggttcgtcgc acaccgtcgc cgacgtgcgt | 540 |
| atcgaccccg aaaacaccga ctgggacgcg ctggctgccg cacccgggcc gctgatcctg | 600 |
| caggccaccg catcgcatct agccgaatcg gcccgcagcc tgatcgatca ccagctggcc | 660 |
| gagtccactc cgtgcgtggt gaccgcacac ggcaccacct gtcagcagcg ttcggtcgag | 720 |
| accacacttc agggattgac cgaccccgcc gtcctgggcg ctaccgaccc cgcgtgctcc | 780 |
| gcaaacggga gggactccca ggccggaccg ctgatagtga ccatcggcaa gacggtgacc | 840 |
| agtcgggcaa agctgaactg gtgggagagc gcgccctct acggctggac ggtgttggtg | 900 |
| ccgcgcacca aggaccaggc cggcgagatg agcgagcggc tcacgtcgta cggcgcgctg | 960 |
| ccggtggagg tgccgaccat cgccgtcgag ccgccgcgca gccccgcgca gatggagcgc | 1020 |
| gccgtcaagg gcctggtcga tggccgattc cagtggatcg tgttcacctc caccaacgcg | 1080 |
| gtgcgtgcgg tgtgggagaa gttcggcgag ttcggtctgg atgcccgcgc gttctccggg | 1140 |
| gtgaagatcg cctgtgtcgg cgagtcgacg gccgaccggg tgcgcgcctt cggaatcagt | 1200 |
| cccgagctgt tgccctccgg ggagcagtcc tcgcttggct tgctagacga cttcccgccc | 1260 |
| tacgacagcg tttttcgaccc ggtgaaccgg gttttgctgc gcgcgccga catcgccacc | 1320 |
| gaaacgctgg ccgagggact gcgagagcgt ggctgggaga tcgaggacgt caccgcctac | 1380 |
| cggaccgtgc gggccgcgcc gccgccggcc actacccggg aaatgatcaa gacgggcggg | 1440 |

```
tttgacgcgg tatgtttcac ctccagctcg acggtgcgaa acctggtcgg catcgccggc   1500
aagccgcacg cgcggacgat catcgcctgc atagggccaa agaccgccga gaccgcagcc   1560
gagttcggct tgcgggtcga tgtccagccg acaccgccg ccatcggccc gctggtcgat    1620
gcgctggccg agcatgccgc ccggttgcgc gctgagggtg cgctgccccc gccgcgcaag   1680
aagagccgca ggcgc                                                    1695

<210> SEQ ID NO 23
<211> LENGTH: 388
<212> TYPE: PRT
<213> ORGANISM: Mycobacterium tuberculosis

<400> SEQUENCE: 23

Met Ser Glu Asp Arg Thr Gly His Gln Gly Ile Ser Gly Pro Ala Thr
1               5                   10                  15

Arg Ala Ile His Ala Gly Tyr Arg Pro Asp Pro Ala Thr Gly Ala Val
            20                  25                  30

Asn Val Pro Ile Tyr Ala Ser Ser Thr Phe Ala Gln Asp Gly Val Gly
        35                  40                  45

Gly Leu Arg Gly Gly Phe Glu Tyr Ala Arg Thr Gly Asn Pro Thr Arg
    50                  55                  60

Ala Ala Leu Glu Ala Ser Leu Ala Ala Val Glu Glu Gly Ala Phe Ala
65                  70                  75                  80

Arg Ala Phe Ser Ser Gly Met Ala Ala Thr Asp Cys Ala Leu Arg Ala
                85                  90                  95

Met Leu Arg Pro Gly Asp His Val Val Ile Pro Asp Asp Ala Tyr Gly
            100                 105                 110

Gly Thr Phe Arg Leu Ile Asp Lys Val Phe Thr Arg Trp Asp Val Gln
        115                 120                 125

Tyr Thr Pro Val Arg Leu Ala Asp Leu Asp Ala Val Gly Ala Ala Ile
    130                 135                 140

Thr Pro Arg Thr Arg Leu Ile Trp Val Glu Thr Pro Thr Asn Pro Leu
145                 150                 155                 160

Leu Ser Ile Ala Asp Ile Thr Ala Ile Ala Glu Leu Gly Thr Asp Arg
                165                 170                 175

Ser Ala Lys Val Leu Val Asp Asn Thr Phe Ala Ser Pro Ala Leu Gln
            180                 185                 190

Gln Pro Leu Arg Leu Gly Ala Asp Val Val Leu His Ser Thr Thr Lys
        195                 200                 205

Tyr Ile Gly Gly His Ser Asp Val Val Gly Gly Ala Leu Val Thr Asn
    210                 215                 220

Asp Glu Glu Leu Asp Glu Glu Phe Ala Phe Leu Gln Asn Gly Ala Gly
225                 230                 235                 240

Ala Val Pro Gly Pro Phe Asp Ala Tyr Leu Thr Met Arg Gly Leu Lys
                245                 250                 255

Thr Leu Val Leu Arg Met Gln Arg His Ser Glu Asn Ala Cys Ala Val
            260                 265                 270

Ala Glu Phe Leu Ala Asp His Pro Ser Val Ser Val Leu Tyr Pro
        275                 280                 285

Gly Leu Pro Ser His Pro Gly His Glu Ile Ala Ala Arg Gln Met Arg
    290                 295                 300

Gly Phe Gly Gly Met Val Ser Val Arg Met Arg Ala Gly Arg Arg Ala
305                 310                 315                 320
```

```
Ala Gln Asp Leu Cys Ala Lys Thr Arg Val Phe Ile Leu Ala Glu Ser
            325                 330                 335

Leu Gly Gly Val Glu Ser Leu Ile Glu His Pro Ser Ala Met Thr His
            340                 345                 350

Ala Ser Thr Ala Gly Ser Gln Leu Glu Val Pro Asp Asp Leu Val Arg
            355                 360                 365

Leu Ser Val Gly Ile Glu Asp Ile Ala Asp Leu Leu Gly Asp Leu Glu
            370                 375                 380

Gln Ala Leu Gly
385

<210> SEQ ID NO 24
<211> LENGTH: 1164
<212> TYPE: DNA
<213> ORGANISM: Mycobacterium tuberculosis

<400> SEQUENCE: 24
atgagcgaag accgcacggg acaccaggga atcagcggac cggccacccg cgccatccac      60
gctggctacc gcccggatcc ggcgaccggg gcggtgaacg tgccgatcta cgccagcagc     120
accttcgccc aagacggcgt cggcggtctg cgtggcggtt tcgaatacgc acgcaccggc     180
aaccccaccc gggccgcatt ggaggcctcg ctggcggcag tcgaggaggg tgctttcgcg     240
cgggcattca gttccgggat ggccgcgacc gactgcgccc tgcgggcgat gttacggccc     300
ggagaccacg tcgtcattcc gatgacgcc tacggcggca cattccggtt gatagacaag     360
gtgttcaccc ggtgggatgt ccagtacacg ccggtgcggc ttgccgatct ggatgcggtg     420
ggtgccgcga ttactccgcg cacccggctg atttgggtgg agacgcccac caatccgcta     480
ctgtcgatcg ccgatatcac ggccattgcc gagctgggca cagacagatc ggcaaaagta     540
ttggtggaca ataccttttgc ctcacccgcg ttgcagcagc cgttgcggct gggcgccgat     600
gtggtgttgc actcgactac caagtacatc ggcggccatt ccgacgtggt gggaggtgcg     660
ctggtcacca cgacgaaga gctggacgag gagttcgctt tcttgcagaa cggcgccggc     720
gcggtgcccg gaccattcga cgcctacctg accatgcgcg gcctgaagac cttggtgctg     780
cggatgcagc ggcacagtga aaatgcctgt gcggtagcgg aattcctcgc tgatcatccg     840
tcggtgagtt ctgtgttgta tccgggtttg cccagtcatc ccgggcatga gattgccgcg     900
cgacagatgc gcggcttcgg cggcatggtt tcggtgcgga tgcgggccgg tcggcgtgcg     960
gcgcaggacc tgtgtgccaa gacccgcgtc ttcatcctgg ccgagtcgct gggtgggg    1020 gagtcgctga tcgaacatcc cagcgccatg acccatgcgt cgacggccgg ttcgcaattg    1080
gaggtgcccg acgatctggt gcggctttcg gtcggtatcg aagacattgc cgacctgctc    1140
ggcgatctcg aacaggccct gggt                                            1164

<210> SEQ ID NO 25
<211> LENGTH: 944
<212> TYPE: PRT
<213> ORGANISM: Mycobacterium tuberculosis

<400> SEQUENCE: 25

Val Phe Ala Trp Trp Gly Arg Thr Val Tyr Arg Tyr Arg Phe Ile Val
1               5                   10                  15

Ile Gly Val Met Val Ala Leu Cys Leu Gly Gly Val Phe Gly Leu
            20                  25                  30

Ser Leu Gly Lys His Val Thr Gln Ser Gly Phe Tyr Asp Asp Gly Ser
            35                  40                  45
```

-continued

```
Gln Ser Val Gln Ala Ser Val Leu Gly Asp Gln Val Tyr Gly Arg Asp
 50                  55                  60

Arg Ser Gly His Ile Val Ala Ile Phe Gln Ala Pro Ala Gly Lys Thr
 65                  70                  75                  80

Val Asp Asp Pro Ala Trp Ser Lys Lys Val Asp Glu Leu Asn Arg
                 85                  90                  95

Phe Gln Gln Asp His Pro Asp Gln Val Leu Gly Trp Ala Gly Tyr Leu
                 100                 105                 110

Arg Ala Ser Gln Ala Thr Gly Met Ala Thr Ala Asp Lys Lys Tyr Thr
                 115                 120                 125

Phe Val Ser Ile Pro Leu Lys Gly Asp Asp Asp Thr Ile Leu Asn
                 130                 135                 140

Asn Tyr Lys Ala Ile Ala Pro Asp Leu Gln Arg Leu Asp Gly Gly Thr
 145                 150                 155                 160

Val Lys Leu Ala Gly Leu Gln Pro Val Ala Glu Ala Leu Thr Gly Thr
                 165                 170                 175

Ile Ala Thr Asp Gln Arg Arg Met Glu Val Leu Ala Leu Pro Leu Val
                 180                 185                 190

Ala Val Val Leu Phe Phe Val Phe Gly Gly Val Ile Ala Ala Gly Leu
                 195                 200                 205

Pro Val Met Val Gly Gly Leu Cys Ile Ala Gly Ala Leu Gly Ile Met
 210                 215                 220

Arg Phe Leu Ala Ile Phe Gly Pro Val His Tyr Phe Ala Gln Pro Val
 225                 230                 235                 240

Val Ser Leu Ile Gly Leu Gly Ile Ala Ile Asp Tyr Gly Leu Phe Ile
                 245                 250                 255

Val Ser Arg Phe Arg Glu Glu Ile Ala Glu Gly Tyr Asp Thr Glu Thr
                 260                 265                 270

Ala Val Arg Arg Thr Val Ile Thr Ala Gly Arg Thr Val Thr Phe Ser
                 275                 280                 285

Ala Val Leu Ile Val Ala Ser Ala Ile Gly Leu Leu Leu Phe Pro Gln
                 290                 295                 300

Gly Phe Leu Lys Ser Leu Thr Tyr Ala Thr Ile Ala Ser Val Met Leu
 305                 310                 315                 320

Ser Ala Ile Leu Ser Ile Thr Val Leu Pro Ala Cys Leu Gly Ile Leu
                 325                 330                 335

Gly Lys His Val Asp Ala Leu Gly Val Arg Thr Leu Phe Arg Val Pro
                 340                 345                 350

Phe Leu Ala Asn Trp Lys Ile Ser Ala Ala Tyr Leu Asn Trp Leu Ala
                 355                 360                 365

Asp Arg Leu Gln Arg Thr Lys Thr Arg Glu Glu Val Glu Ala Gly Phe
 370                 375                 380

Trp Gly Lys Leu Val Asn Arg Val Met Lys Arg Pro Val Leu Phe Ala
 385                 390                 395                 400

Ala Pro Ile Val Ile Met Ile Leu Leu Ile Ile Pro Val Gly Lys
                 405                 410                 415

Leu Ser Leu Gly Gly Ile Ser Glu Lys Tyr Leu Pro Pro Thr Asn Ser
                 420                 425                 430

Val Arg Gln Ala Gln Glu Glu Phe Asp Lys Leu Phe Pro Gly Tyr Arg
                 435                 440                 445

Thr Asn Pro Leu Thr Leu Val Ile Gln Thr Ser Asn His Gln Pro Val
 450                 455                 460
```

-continued

```
Thr Asp Ala Gln Ile Ala Asp Ile Arg Ser Lys Ala Met Ala Ile Gly
465                 470                 475                 480

Gly Phe Ile Glu Pro Asp Asn Asp Pro Ala Asn Met Trp Gln Glu Arg
                485                 490                 495

Ala Tyr Ala Val Gly Ala Ser Lys Asp Pro Ser Val Arg Val Leu Gln
                500                 505                 510

Asn Gly Leu Ile Asn Pro Ala Asp Ala Ser Lys Lys Leu Thr Glu Leu
                515                 520                 525

Arg Ala Ile Thr Pro Lys Gly Ile Thr Val Leu Val Gly Gly Thr
530                 535                 540

Pro Ala Leu Glu Leu Asp Ser Ile His Gly Leu Phe Ala Lys Met Pro
545                 550                 555                 560

Leu Met Val Val Ile Leu Leu Thr Thr Thr Ile Val Leu Met Phe Leu
                565                 570                 575

Ala Phe Gly Ser Val Val Leu Pro Ile Lys Ala Thr Leu Met Ser Ala
                580                 585                 590

Leu Thr Leu Gly Ser Thr Met Gly Ile Leu Thr Trp Ile Phe Val Asp
                595                 600                 605

Gly His Phe Ser Lys Trp Leu Asn Phe Thr Pro Thr Pro Leu Thr Ala
                610                 615                 620

Pro Val Ile Gly Leu Ile Ile Ala Leu Val Phe Gly Leu Ser Thr Asp
625                 630                 635                 640

Tyr Glu Val Phe Leu Val Ser Arg Met Val Glu Ala Arg Glu Arg Gly
                645                 650                 655

Met Ser Thr Gln Glu Ala Ile Arg Ile Gly Thr Ala Ala Thr Gly Arg
                660                 665                 670

Ile Ile Thr Ala Ala Ala Leu Ile Val Ala Val Ala Gly Ala Phe
                675                 680                 685

Val Phe Ser Asp Leu Val Met Met Lys Tyr Leu Ala Phe Gly Leu Met
                690                 695                 700

Ala Ala Leu Leu Leu Asp Ala Thr Val Val Arg Met Phe Leu Val Pro
705                 710                 715                 720

Ser Val Met Lys Leu Leu Gly Asp Asp Cys Trp Trp Ala Pro Arg Trp
                725                 730                 735

Ala Arg Arg Leu Gln Thr Arg Ile Gly Leu Gly Glu Ile His Leu Pro
                740                 745                 750

Asp Glu Arg Lys Arg Pro Val Ser Asn Gly Arg Pro Ala Arg Pro Pro
                755                 760                 765

Val Thr Ala Gly Leu Val Ala Ala Arg Ala Ala Gly Asp Pro Arg Pro
                770                 775                 780

Pro His Asp Pro Thr His Pro Leu Ala Glu Ser Pro Arg Pro Ala Arg
785                 790                 795                 800

Ser Ser Pro Ala Ser Ser Pro Glu Leu Thr Pro Ala Leu Glu Ala Thr
                805                 810                 815

Ala Ala Pro Ala Ala Pro Ser Gly Ala Ser Thr Thr Arg Met Gln Ile
                820                 825                 830

Gly Ser Thr Glu Pro Pro Thr Thr Arg Leu Ala Ala Ala Gly Arg
                835                 840                 845

Ser Val Gln Ser Pro Ala Ser Thr Pro Pro Thr Pro Thr Pro Pro
                850                 855                 860

Ser Ala Pro Ser Ala Gly Gln Thr Arg Ala Met Pro Leu Ala Ala Asn
865                 870                 875                 880

Arg Ser Thr Asp Ala Ala Gly Asp Pro Ala Glu Pro Thr Ala Ala Leu
```

|  | 885 | 890 | 895 |  |
|---|---|---|---|---|

Pro Ile Ile Arg Ser Asp Gly Asp Ser Glu Ala Ala Thr Glu Gln
             900                 905                 910

Leu Asn Ala Arg Gly Thr Ser Asp Lys Thr Arg Gln Arg Arg Gly
         915                 920                 925

Gly Gly Ala Leu Ser Ala Gln Asp Leu Leu Arg Arg Glu Gly Arg Leu
         930                 935                 940

<210> SEQ ID NO 26
<211> LENGTH: 2832
<212> TYPE: DNA
<213> ORGANISM: Mycobacterium tuberculosis

<400> SEQUENCE: 26

```
gtgttcgcct ggtggggtcg aactgtgtac cgctaccggt tcatcgtaat cggggtcatg      60
gtcgctctat gcctcggcgg cggcgttttc gggctgagcc tcggcaagca cgtcacgcag     120
agcggcttct acgacgacgg cagccaatcg gtgcaagcat cggtgctggg cgaccaggtc     180
tacggccgag accgaagcgg tcacatcgtc gcgatcttcc aagccccagc ggcaagacc      240
gttgacgacc cggcctggtc aaagaaggtc gtcgacgagc tcaaccggtt ccagcaggat     300
caccccgacc aggtcttggg atgggccggc tacctgagag cgagtcaggc gaccggcatg     360
gccaccgccg acaagaagta caccttcgtt ccatcccgc tcaagggtga tgacgacgac      420
accatcctca caactacaa ggccatcgca cccgacctgc agcggctcga cggaggcacg      480
gtgaagctcg ccgggctgca accggtgcc gaggcgttga ccggcaccat cgccaccgac      540
caacggcgaa tggaagtgct ggcgctgccg ttggtggcgg tggtgttgtt cttcgtgttc     600
ggcggcgtga tcgccgccgg cctaccggtg atggtcggag gctgtgcat cgccggcgcg     660
ctgggcatca tgcggttcct cgcgatcttc ggtcccgtgc actatttcgc ccagcccgtg     720
gtgtcgctga tcggtctggg gatcgccatc gactacgggt tgttcatcgt gagccggttc     780
cgcgaagaga tcgccgaagg ctacgacacc gagacggcag tacggcgcac ggtgatcacc     840
gccgacgca cggtgacgtt ctcggcgtg ttgatcgtcg cgtcggcgat cggtctgctg      900
ctcttcccgc agggtttcct gaagtcgctg acctacgcca cgatcgcatc ggtgatgctg     960
tcggccatcc tgtctatcac cgtgttgccg gcctgtctgg ggatcctggg caaacacgtc    1020
gacgcgctcg gcgtgcggac cctgttccgg gtgcccttcc tggcgaactg aagatttcg    1080
gccgcctacc tgaactggct cgccgaccgc ctgcagcgga ccaagacccg cgaagaggtc    1140
gaagccggct tctggggcaa gctggttaac cgggtgatga agcgcccagt gctgttcgcc    1200
gcaccgatcg tcatcatcat gatttttgctg attatcccgg tgggcaagct gtcattgggc    1260
gggatcagcg agaagtactt gccgccgacc aattcggtgc gccaggcgca ggaggagttc    1320
gacaaactct ccccggata ccgcaccaat ccgctgacac tggtgatcca gaccagcaac    1380
catcaaccgg tcaccgacgc gcagatcgct gacatccgca gcaaggcgat ggcgatcggc    1440
ggattcatcg agccggacaa cgatccggcg aatatgtggc aagagcgtgc ctacgcggta    1500
ggcgcatcta aagatccatc ggtgcgcgtc ctgcagaacg ggttgatcaa cccggctgac    1560
gcgtcgaaga agctcaccga gctgcgcgcg atcacccgc ccaaaggaat cacggtcttg    1620
gtcggtggaa ctcccgccct ggagctggat tcaatccacg gcctgttcgc gaagatgccg    1680
ctgatggtgg tcatcctgct gaccaccacg atcgtcttga tgttcttggc gttcggctcg    1740
gtggtgctgc caatcaaggc gacgctgatg agcgctctga cgctcgggtc caccatgggc    1800
```

-continued

```
atcctgacgt ggatattcgt cgacggacac ttttcgaagt ggctgaattt cacgccgacc    1860
ccgctgacag cgccggtgat cgggctgatc atcgcgctgg tcttcggcct atccaccgac    1920
tacgaggtgt tcttggtgtc ccggatggtc gaggcgcgag agcgcggcat gtcgacccag    1980
gaggcgatcc ggatcggcac cgcagccacc ggacgcatca ttaccgccgc ggcgctgatt    2040
gttgccgtcg tcgcgggcgc gttcgtgttc tccgacctgg tgatgatgaa gtatctggcc    2100
tttggactga tggcggcgct gctgctggac gcgaccgtgg tgcggatgtt tttagtgcca    2160
tcggtgatga agctgctcgg cgatgactgc tggtgggcac cgcgctgggc cagacgcctg    2220
cagacccgca tcgggctggg cgagatccac ctgcccgacg agcgcaagcg gcccgtcagc    2280
aacgggcgtc ccgcacgtcc tccggtcaca gctgggctgg ttgcggcgcg cgccgctggg    2340
gacccgcgcc caccgcacga tccgacccat ccgctggcgg agtcacctcg accgcccgc     2400 tcgagtccag caagctcacc ggagctcacg cctgccctgg aagcaactgc cgcgccggcg    2460
gcgccgtctg gggcgagcac cacacggatg cagatcgggt cgtcgacgga gccgccgaca    2520
acccgcctcg cggctgccgg tcggtccgtg cagtcgccag catccacgcc gccaccaacc    2580
ccgaccccgc catcggcccc gtctgccggt cagacccggg ctatgccgct tgcggcgaac    2640
cgctccacag acgcagccgg tgacccggcc gaacccaccg cggccctgcc aatcatacgg    2700
tcggacggcg acgactcaga ggcagccact gagcagctga atgcccgcgg cacgagcgat    2760
aagacgcgtc agcgccgccg cggcggcggc gccctgtccg cccaggatct gcttcgccgc    2820
gaaggacgcc tt                                                       2832
```

<210> SEQ ID NO 27
<211> LENGTH: 920
<212> TYPE: PRT
<213> ORGANISM: Mycobacterium tuberculosis

<400> SEQUENCE: 27

```
Met Pro Ser Pro Ala Gly Arg Leu His Arg Ile Arg Tyr Ile Arg Leu
1               5                   10                  15

Lys Lys Ser Ser Pro Asp Cys Arg Ala Thr Ile Thr Ser Gly Ser Ala
            20                  25                  30

Asp Gly Gln Arg Arg Ser Pro Arg Leu Thr Asn Leu Leu Val Val Ala
        35                  40                  45

Ala Trp Val Ala Ala Val Ile Ala Asn Leu Leu Leu Thr Phe Thr
    50                  55                  60

Gln Ala Glu Pro His Asp Thr Ser Pro Ala Leu Leu Pro Gln Asp Ala
65                  70                  75                  80

Lys Thr Ala Ala Ala Thr Ser Arg Ile Ala Gln Ala Phe Pro Gly Thr
                85                  90                  95

Gly Ser Asn Ala Ile Ala Tyr Leu Val Val Glu Gly Gly Ser Thr Leu
            100                 105                 110

Glu Pro Gln Asp Gln Pro Tyr Tyr Asp Ala Ala Val Gly Ala Leu Arg
        115                 120                 125

Ala Asp Thr Arg His Val Gly Ser Val Leu Asp Trp Trp Ser Asp Pro
    130                 135                 140

Val Thr Ala Pro Leu Gly Thr Ser Pro Asp Gly Arg Ser Ala Thr Ala
145                 150                 155                 160

Met Val Trp Leu Arg Gly Glu Ala Gly Thr Thr Gln Ala Ala Glu Ser
                165                 170                 175

Leu Asp Ala Val Arg Ser Val Leu Arg Gln Leu Pro Pro Ser Glu Gly
            180                 185                 190
```

```
Leu Arg Ala Ser Ile Val Val Pro Ala Ile Thr Asn Asp Met Pro Met
    195                 200                 205
Gln Ile Thr Ala Trp Gln Ser Ala Thr Ile Val Thr Val Ala Ala Val
    210                 215                 220
Ile Ala Val Leu Leu Leu Arg Ala Arg Leu Ser Val Arg Ala Ala
225                 230                 235                 240
Ala Ile Val Leu Leu Thr Ala Asp Leu Ser Leu Ala Val Ala Trp Pro
                245                 250                 255
Leu Ala Ala Val Val Arg Gly His Asp Trp Gly Thr Asp Ser Val Phe
                260                 265                 270
Ser Trp Thr Leu Ala Ala Val Leu Thr Ile Gly Thr Ile Thr Ala Ala
        275                 280                 285
Thr Met Leu Ala Ala Arg Leu Gly Ser Asp Ala Gly His Ser Ala Ala
        290                 295                 300
Pro Thr Tyr Arg Asp Ser Leu Pro Ala Phe Ala Leu Pro Gly Ala Cys
305                 310                 315                 320
Val Ala Ile Phe Thr Gly Pro Leu Leu Leu Ala Arg Thr Pro Ala Leu
                325                 330                 335
His Gly Val Gly Thr Ala Gly Leu Gly Val Phe Val Ala Leu Ala Ala
                340                 345                 350
Ser Leu Thr Val Leu Pro Ala Leu Ile Ala Leu Ala Gly Ala Ser Arg
        355                 360                 365
Gln Leu Pro Ala Pro Thr Thr Gly Ala Gly Trp Thr Gly Arg Leu Ser
        370                 375                 380
Leu Pro Val Ser Ser Ala Ser Ala Leu Gly Thr Ala Ala Val Leu Ala
385                 390                 395                 400
Ile Cys Met Leu Pro Ile Ile Gly Met Arg Trp Gly Val Ala Glu Asn
                405                 410                 415
Pro Thr Arg Gln Gly Gly Ala Gln Val Leu Pro Gly Asn Ala Leu Pro
                420                 425                 430
Asp Val Val Ile Lys Ser Ala Arg Asp Leu Arg Asp Pro Ala Ala
        435                 440                 445
Leu Ile Ala Ile Asn Gln Val Ser His Arg Leu Val Glu Val Pro Gly
    450                 455                 460
Val Arg Lys Val Glu Ser Ala Ala Trp Pro Ala Gly Val Pro Trp Thr
465                 470                 475                 480
Asp Ala Ser Leu Ser Ser Ala Gly Arg Leu Ala Asp Gln Leu Gly
                485                 490                 495
Gln Gln Ala Gly Ser Phe Val Pro Ala Val Thr Ala Ile Lys Ser Met
                500                 505                 510
Lys Ser Ile Ile Glu Gln Met Ser Gly Ala Val Asp Gln Leu Asp Ser
        515                 520                 525
Thr Val Asn Val Thr Leu Ala Gly Ala Arg Gln Ala Gln Gln Tyr Leu
        530                 535                 540
Asp Pro Met Leu Ala Ala Ala Arg Asn Leu Lys Asn Lys Thr Thr Glu
545                 550                 555                 560
Leu Ser Glu Tyr Leu Glu Thr Ile His Thr Trp Ile Val Gly Phe Thr
                565                 570                 575
Asn Cys Pro Asp Asp Val Leu Cys Thr Ala Met Arg Lys Val Ile Glu
                580                 585                 590
Pro Tyr Asp Ile Val Val Thr Gly Met Asn Glu Leu Ser Thr Gly Ala
    595                 600                 605
```

```
Asp Arg Ile Ser Ala Ile Ser Thr Gln Thr Met Ser Ala Leu Ser Ser
        610                 615                 620
Ala Pro Arg Met Val Ala Gln Met Arg Ser Ala Leu Ala Gln Val Arg
625                 630                 635                 640
Ser Phe Val Pro Lys Leu Glu Thr Thr Ile Gln Asp Ala Met Pro Gln
                645                 650                 655
Ile Ala Gln Ala Ser Ala Met Leu Lys Asn Leu Ser Ala Asp Phe Ala
            660                 665                 670
Asp Thr Gly Glu Gly Gly Phe His Leu Ser Arg Lys Asp Leu Ala Asp
        675                 680                 685
Pro Ser Tyr Arg His Val Arg Glu Ser Met Phe Ser Ser Asp Gly Thr
    690                 695                 700
Ala Thr Arg Leu Phe Leu Tyr Ser Asp Gly Gln Leu Asp Leu Ala Ala
705                 710                 715                 720
Ala Ala Arg Ala Gln Gln Leu Glu Ile Ala Ala Gly Lys Ala Met Lys
                725                 730                 735
Tyr Gly Ser Leu Val Asp Ser Gln Val Thr Val Gly Gly Ala Ala Gln
            740                 745                 750
Ile Ala Ala Val Arg Asp Ala Leu Ile His Asp Ala Val Leu Leu
        755                 760                 765
Ala Val Ile Leu Leu Thr Val Val Ala Leu Ala Ser Met Trp Arg Gly
    770                 775                 780
Ala Val His Gly Ala Ala Val Gly Val Gly Val Leu Ala Ser Tyr Leu
785                 790                 795                 800
Ala Ala Leu Gly Val Ser Ile Ala Leu Trp Gln His Leu Leu Asp Arg
                805                 810                 815
Glu Leu Asn Ala Leu Val Pro Leu Val Ser Phe Ala Val Leu Ala Ser
            820                 825                 830
Cys Gly Val Pro Tyr Leu Val Ala Gly Ile Lys Ala Gly Arg Ile Ala
        835                 840                 845
Asp Glu Ala Thr Gly Ala Arg Ser Lys Gly Ala Val Ser Gly Arg Gly
    850                 855                 860
Ala Val Ala Pro Leu Ala Leu Gly Gly Val Phe Gly Ala Gly Leu
865                 870                 875                 880
Val Leu Val Ser Gly Gly Ser Phe Ser Val Leu Ser Gln Ile Gly Thr
                885                 890                 895
Val Val Val Leu Gly Leu Gly Val Leu Ile Thr Val Gln Arg Ala Trp
            900                 905                 910
Leu Pro Thr Thr Pro Gly Arg Arg
        915                 920
```

<210> SEQ ID NO 28
<211> LENGTH: 2760
<212> TYPE: DNA
<213> ORGANISM: Mycobacterium tuberculosis

<400> SEQUENCE: 28

| | |
|---|---|
| atgcctagtc cggctggccg tctacacaga attcggtata tccgtttgaa aaagtcctcc | 60 |
| ccggactgcc gcgccaccat caccagcggg tcagccgacg gtcagcgaag gtcaccccgg | 120 |
| ctcaccaacc tgctcgtcgt cgccgcctgg gttgccgcgg cggtgatcgc aaatctgctt | 180 |
| ctcacgttca cgcaagcaga accgcacgac accagcccgg cgctgctgcc acaagatgcc | 240 |
| aagacagccg ccgccaccag ccggattgcg caggctttcc ccggcaccgg tagcaacgct | 300 |
| atcgcctatc tcgtcgtgga aggcggcagc acgcttgagc cgcaggacca gccttactac | 360 |

-continued

```
gacgccgccg tcggtgccct gcgcgccgac acccgccacg tgggatccgt cctcgactgg      420
tggtcagatc ccgtcaccgc cccgctggga accagccccg acggccgctc cgctacggcc      480
atggtgtggc tgcggggcga ggcgggcacc acccaagctg ccgaatccct cgatgccgtc      540
cgatcggtgc tgcgccagtt accgcccagt gaggggcttc gcgccagcat cgtggtcccg      600
gcaatcacca acgacatgcc gatgcagata accgcctggc agagcgcgac gatcgtgacc      660
gttgcggcgg tgatcgccgt cctactgctg ctgcgggcgc gcctgtcggt gcgggccgcg      720
gcgatcgtgc tgctgaccgc ggacttgtcg cttgcggtgg cctggccgct ggccgcggtg      780
gtgcggggac acgattgggg aaccgattcg gtattttctt ggacgctggc cgcggtcctg      840
acgatcggaa ccatcaccgc agccaccatg ctggccgcgc ggctcgggtc cgacgcaggt      900
cattcggccg cgcccacata ccgcgacagc ctgcccgcgt tcgccctgcc cggggcgtgt      960
gtcgccatat tcaccggccc gctgctgctg gcccgaaccc cagcgctgca cggagttggc     1020
actgccgggc taggtgtctt tgtggcactt gcggcttcgt tgacggtgct gcctgccctg     1080
atcgcgcttg ccggagcgtc acggcagtta ccggcaccaa ccacgggtgc cggctggaca     1140
ggccggttgt cgctacccgt ctcttctgct tcggccctgg gcacagcggc agtgctggcg     1200
atctgcatgc tacccatcat cgggatgcgg tggggtgtgg ccgagaaccc gacaaggcaa     1260
ggcggcgcac aagtccttcc ggggaatgcg cttcccgatg tggtggtgat caaatccgct     1320
cgggacctga gggacccagc cgcgctcatc gccatcaacc aggtcagcca ccgtctggtg     1380
gaggttcccg gtgtgcgcaa ggtggagtcg gcggcatggc cggccggtgt cccgtggacc     1440
gacgcctcgc tcagttccgc ggccggcagg ctcgccgacc agctgggtca gcaggccgga     1500
tcgttcgtgc cggcggtgac tgcgatcaaa tcgatgaagt ccataatcga acagatgagc     1560
ggcgcggtcg accaactgga cagcaccgtg aacgtgactc tcgccggggc aaggcaagca     1620
cagcaatacc tcgatcccat gctcgccgcc gcgcggaacc tcaaaaacaa accaccgaa      1680 ctgtcggaat acctggaaac gatccacacc tggattgtcg gcttcacaaa ctgccccgac     1740
gacgtcctgt gcacgccat cgcaaggtc attgaaccct acgacatcgt ggtcaccggc      1800
atgaacgagc tgtccactgg cgccgaccgc atctccgcga tatcgacaca gacaatgagc     1860
gcgttgtcct cggcaccgcg gatggtggcg cagatgcggt cggcgctagc acaggtgcgc     1920
tcgttcgtac ccaagctgga aacaaccatc caggacgcca tgccgcaaat agcgcaggcg     1980
tcggcgatgc tgaagaatct cagcgccgat ttcgccgata ccggtgaggg cggcttccac     2040
ctgtccagga aggacctggc ggacccgtcg taccggcacg tacgggaatc gatgttctcg     2100
tcagacggaa ccgccacccg gctgttcctc tattctgacg acaactggaa ccttgctgcg     2160
gcagcacgcg cgcagcagct cgagatcgcc gcgggcaagg cgatgaaata cggaagcctg     2220
gtcgacagcc aggtcacggt gggtggggcc gcgcaaatag ccgcggctgt ccgcgatgcc     2280
ctcatccacg atgctgtgct actggccgtt atcttgctca cggtagtggc tctggccagc     2340
atgtggcgcg gtgccgtcca cggtgctgcg gttggcgtgg tgtgctggc ctcttacctc      2400 gccgccctgg gggtctcgat tgcactgtgg caacacctac tggatcgcga gctcaacgcc     2460
ttggtcccgc tggtgtcgtt cgccgtcctc gcttcgtgcg gcgtcccgta tctcgttgcc     2520
ggcatcaaag ccggtcgtat cgccgacgag gcaacgggtg cgcggtccaa gggggcggta     2580
tccgggcggg gagcggttgc gccgcttgcg gcgctcggtg gcgtattcgg cgctggcctg     2640
gtgctggtgt cgggaggttc cttcagcgtg ctcagtcaga ttggcacggt tgttgtgctc     2700
```

```
ggtctgggcg tgctgatcac ggtgcagcga gcgtggcttc cgaccacgcc agggcggcgt    2760
```

```
<210> SEQ ID NO 29
<211> LENGTH: 84
<212> TYPE: PRT
<213> ORGANISM: Mycobacterium tuberculosis

<400> SEQUENCE: 29
```

Met Ala Lys Ser Ser Lys Arg Arg Pro Ala Pro Glu Lys Pro Val Lys
1               5                   10                  15

Thr Arg Lys Cys Val Phe Cys Ala Lys Lys Asp Gln Ala Ile Asp Tyr
            20                  25                  30

Lys Asp Thr Ala Leu Leu Arg Thr Tyr Ile Ser Glu Arg Gly Lys Ile
        35                  40                  45

Arg Ala Arg Arg Val Thr Gly Asn Cys Val Gln His Gln Arg Asp Ile
    50                  55                  60

Ala Leu Ala Val Lys Asn Ala Arg Glu Val Ala Leu Leu Pro Phe Thr
65                  70                  75                  80

Ser Ser Val Arg

```
<210> SEQ ID NO 30
<211> LENGTH: 252
<212> TYPE: DNA
<213> ORGANISM: Mycobacterium tuberculosis

<400> SEQUENCE: 30
```

```
atggccaagt ccagcaagcg gcgcccggct ccggaaaagc cggtcaagac gcgtaaatgc     60
gtgttctgcg cgaagaagga ccaagcgatc gactacaagg acaccgcgct gttgcgcacc    120
tacatcagcg agcgcggcaa gatccgcgcg cgtcgggtca cgggcaactg cgtgcagcac    180
cagcgagaca tcgcgctcgc ggtgaagaac gcccgcgagg tggcgctgct gccctttacg    240
tcttcggtgc gg                                                        252
```

```
<210> SEQ ID NO 31
<211> LENGTH: 280
<212> TYPE: PRT
<213> ORGANISM: Mycobacterium tuberculosis

<400> SEQUENCE: 31
```

Val Pro His Ser Trp Thr Pro Thr Ser Val Met Thr Pro Pro Leu Val
1               5                   10                  15

Val Ala Ala Phe Arg Pro Val Gly His Tyr Arg Leu Ala Thr Asp Arg
            20                  25                  30

Ala Gly Gly Pro Cys Ser Pro Pro Ala Thr Gly Ala Lys Leu Thr Ser
        35                  40                  45

Ser Val Ala Ser Arg Pro Thr Val Gly Thr Lys Pro Gln Trp Trp His
    50                  55                  60

Thr Leu Val Met Ser Met Ser Leu Thr Ala Gly Arg Gly Pro Gly Arg
65                  70                  75                  80

Pro Pro Ala Ala Lys Ala Asp Glu Thr Arg Lys Arg Ile Leu His Ala
                85                  90                  95

Ala Arg Gln Val Phe Ser Glu Arg Gly Tyr Asp Gly Ala Thr Phe Gln
            100                 105                 110

Glu Ile Ala Val Arg Ala Asp Leu Thr Arg Pro Ala Ile Asn His Tyr
        115                 120                 125

Phe Ala Asn Lys Arg Val Leu Tyr Gln Glu Val Val Glu Gln Thr His
    130                 135                 140

```
Glu Leu Val Ile Val Ala Gly Ile Glu Arg Ala Arg Arg Glu Pro Thr
145                 150                 155                 160

Leu Met Gly Arg Leu Ala Val Val Asp Phe Ala Met Glu Ala Asp
            165                 170                 175

Ala Gln Tyr Pro Ala Ser Thr Ala Phe Leu Ala Thr Val Leu Glu
            180                 185                 190

Ser Gln Arg His Pro Glu Leu Ser Arg Thr Glu Asn Asp Ala Val Arg
            195                 200                 205

Ala Thr Arg Glu Phe Leu Val Trp Ala Val Asn Asp Ala Ile Glu Arg
        210                 215                 220

Gly Glu Leu Ala Ala Asp Val Asp Val Ser Ser Leu Ala Glu Thr Leu
225                 230                 235                 240

Leu Val Val Leu Cys Gly Val Gly Phe Tyr Ile Gly Phe Val Gly Ser
                245                 250                 255

Tyr Gln Arg Met Ala Thr Ile Thr Asp Ser Phe Gln Gln Leu Leu Ala
            260                 265                 270

Gly Thr Leu Trp Arg Pro Pro Thr
        275                 280

<210> SEQ ID NO 32
<211> LENGTH: 840
<212> TYPE: DNA
<213> ORGANISM: Mycobacterium tuberculosis

<400> SEQUENCE: 32
gtgccgcact cttggacccc gacctctgtc atgacgccgc cgctcgtcgt ggccgcgttc      60
aggccggtcg gccattaccg actcgcaacg gacagagccg gtgggccctg ctcgcccccg     120
gcgaccggag ccaagctgac aagttccgta gcatcccgcc caacggtagg taccaagccg     180
cagtggtggc acactttagt gatgtcaatg tcgctcacgg ccggtcgcgg cccgggacgt     240 ccccccggcgg cgaaagcaga tgagactcgg aagcgtattc tgcacgccgc ccgtcaagtg     300
ttcagcgaac gtggttatga cggcgcgact tttcaggaga tcgccgtccg cgccgacctg     360
acccgaccgg cgatcaacca ctacttcgcc aacaagcggg tgctctacca agaggtggtg     420
gagcaaaccc cgaactcgt cattgtggcc ggcatcgaac gggcacgccg cgagccgacc     480
ttgatggggc ggctggcggt cgtcgttgac ttcgcgatgg aggccgatgc ccagtatccc     540
gcctcgaccg cgttcctggc caccaccgtg ctcgaatccc agcggcatcc agaattgagt     600
cggaccgaaa acgatgcggt gcgagcaacc cgagaattcc tggtttgggc tgtcaatgat     660
gcgatcgaac gcggtgaact agccgccgac gtcgatgtct cttcgttggc cgagacgctg     720
ttggtcgtgt tgtgtggcgt gggcttctat atcggttttg tcgggagcta tcagcggatg     780
gcgaccatca ccgattcgtt ccagcagctg ttggccggca cgctctggcg gcctccgacc     840

<210> SEQ ID NO 33
<211> LENGTH: 663
<212> TYPE: PRT
<213> ORGANISM: Mycobacterium tuberculosis

<400> SEQUENCE: 33

Val Thr Leu Ala Ile Pro Ser Gly Ile Asp Leu Ser His Ile Asp Ala
1               5                   10                  15

Asp Ala Arg Pro Gln Asp Asp Leu Phe Gly His Val Asn Gly Arg Trp
            20                  25                  30

Leu Ala Glu His Glu Ile Pro Ala Asp Arg Ala Thr Asp Gly Ala Phe
```

```
                35                  40                  45
Arg Ser Leu Phe Asp Arg Ala Glu Thr Gln Val Arg Asp Leu Ile Ile
 50                  55                  60
Gln Ala Ser Gln Ala Gly Ala Ala Val Gly Thr Asp Ala Gln Arg Ile
 65                  70                  75                  80
Gly Asp Leu Tyr Ala Ser Phe Leu Asp Glu Glu Ala Val Glu Arg Ala
                 85                  90                  95
Gly Val Gln Pro Leu His Asp Glu Leu Ala Thr Ile Asp Ser Ala Ala
                100                 105                 110
Asp Ala Thr Glu Leu Ala Ala Leu Gly Thr Leu Gln Arg Ala Gly
            115                 120                 125
Val Gly Gly Gly Ile Gly Val Tyr Val Asp Thr Asp Ser Lys Asp Ser
130                 135                 140
Thr Arg Tyr Leu Val His Phe Thr Gln Ser Gly Ile Gly Leu Pro Asp
145                 150                 155                 160
Glu Ser Tyr Tyr Arg Asp Glu Gln His Ala Ala Val Leu Ala Ala Tyr
                165                 170                 175
Pro Gly His Ile Ala Arg Met Phe Gly Leu Val Tyr Gly Gly Glu Ser
            180                 185                 190
Arg Asp His Ala Lys Thr Ala Asp Arg Ile Val Ala Leu Glu Thr Lys
        195                 200                 205
Leu Ala Asp Ala His Trp Asp Val Val Lys Arg Arg Asp Ala Asp Leu
210                 215                 220
Gly Tyr Asn Leu Arg Thr Phe Ala Gln Leu Gln Thr Glu Gly Ala Gly
225                 230                 235                 240
Phe Asp Trp Val Ser Trp Val Thr Ala Leu Gly Ser Ala Pro Asp Ala
                245                 250                 255
Met Thr Glu Leu Val Val Arg Gln Pro Asp Tyr Leu Val Thr Phe Ala
            260                 265                 270
Ser Leu Trp Ala Ser Val Asn Val Glu Asp Trp Lys Cys Trp Ala Arg
        275                 280                 285
Trp Arg Leu Ile Arg Ala Arg Ala Pro Trp Leu Thr Arg Ala Leu Val
290                 295                 300
Ala Glu Asp Phe Glu Phe Tyr Gly Arg Thr Leu Thr Gly Ala Gln Gln
305                 310                 315                 320
Leu Arg Asp Arg Trp Lys Arg Gly Val Ser Leu Val Glu Asn Leu Met
                325                 330                 335
Gly Asp Ala Val Gly Lys Leu Tyr Val Gln Arg His Phe Pro Pro Asp
            340                 345                 350
Ala Lys Ser Arg Ile Asp Thr Leu Val Asp Asn Leu Gln Glu Ala Tyr
        355                 360                 365
Arg Ile Ser Ile Ser Glu Leu Asp Trp Met Thr Pro Gln Thr Arg Gln
370                 375                 380
Arg Ala Leu Ala Lys Leu Asn Lys Phe Thr Ala Lys Val Gly Tyr Pro
385                 390                 395                 400
Ile Lys Trp Arg Asp Tyr Ser Lys Leu Ala Ile Asp Arg Asp Leu
                405                 410                 415
Tyr Gly Asn Val Gln Arg Gly Tyr Ala Val Asn His Asp Arg Glu Leu
            420                 425                 430
Ala Lys Leu Phe Gly Pro Val Asp Arg Asp Glu Trp Phe Met Thr Pro
        435                 440                 445
Gln Thr Val Asn Ala Tyr Tyr Asn Pro Gly Met Asn Glu Ile Val Phe
450                 455                 460
```

-continued

```
Pro Ala Ala Ile Leu Gln Pro Pro Phe Phe Asp Pro Gln Ala Asp Glu
465                 470                 475                 480

Ala Ala Asn Tyr Gly Gly Ile Gly Ala Val Ile Gly His Glu Ile Gly
            485                 490                 495

His Gly Phe Asp Asp Gln Gly Ala Lys Tyr Asp Gly Asp Gly Asn Leu
        500                 505                 510

Val Asp Trp Trp Thr Asp Asp Arg Thr Glu Phe Ala Ala Arg Thr
    515                 520                 525

Lys Ala Leu Ile Glu Gln Tyr His Ala Tyr Thr Pro Arg Asp Leu Val
530                 535                 540

Asp His Pro Gly Pro Pro His Val Gln Gly Ala Phe Thr Ile Gly Glu
545                 550                 555                 560

Asn Ile Gly Asp Leu Gly Gly Leu Ser Ile Ala Leu Leu Ala Tyr Gln
            565                 570                 575

Leu Ser Leu Asn Gly Asn Pro Ala Pro Val Ile Asp Gly Leu Thr Gly
        580                 585                 590

Met Gln Arg Val Phe Phe Gly Trp Ala Gln Ile Trp Arg Thr Lys Ser
    595                 600                 605

Arg Ala Ala Glu Ala Ile Arg Arg Leu Ala Val Asp Pro His Ser Pro
610                 615                 620

Pro Glu Phe Arg Cys Asn Gly Val Val Arg Asn Val Asp Ala Phe Tyr
625                 630                 635                 640

Gln Ala Phe Asp Val Thr Glu Asp Asp Ala Leu Phe Leu Asp Pro Gln
            645                 650                 655

Arg Arg Val Arg Ile Trp Asn
            660
```

<210> SEQ ID NO 34
<211> LENGTH: 1989
<212> TYPE: DNA
<213> ORGANISM: Mycobacterium tuberculosis

<400> SEQUENCE: 34

| | | | |
|---|---|---|---|
| gtgacacttg ccatcccctc gggtatcgac ctgagccaca tcgacgctga tgcccgaccc | 60 |
| caagacgacc tgttcggcca cgttaacggc cgctggctgg ctgaacacga gataccagcg | 120 |
| gaccgagcga ccgacggcgc cttccgtagc ctgttcgacc gcgccgagac acaagtgcga | 180 |
| gacctgatca tccaggccag ccaagcaggt gctgcggtag caccgatgc gcagcgcatc | 240 |
| ggcgacctct acgccagctt cctcgacgag gaagccgtcg agcgcgcagg ggtgcaaccg | 300 |
| ctgcacgacg aattggccac gattgacagc gcggccgacg ccaccgaatt ggccgccgcc | 360 |
| cttggcactc tgcaacgtgc cggcgtgggc ggcggcatcg gagtctatgt cgataccgat | 420 |
| tccaaagact cgacccgtta cttggtgcat tcacccaat ccggcatcgg attacccgac | 480 |
| gagtcctact accgtgacga gcaacacgcc gccgtgctag cggcctaccc ggggcacatc | 540 |
| gcccggatgt tcggcctggt gtacgggggc gagagccgtg accatgccaa accgcggac | 600 |
| cgcatcgtcg cgctggagac caaactcgcc gacgcgcatt gggatgtggt gaagcgccgc | 660 |
| gacgccgacc ttggctacaa cctgcgcacg tttgcccagc tgcagaccga aggggcgggt | 720 |
| ttcgactggg tcagctggt gaccgcattg gggagcgctc cggacgccat gacggaactg | 780 |
| gttgtgcgcc aacctgatta cctcgtcacc tttgcctcgc tgtgggcgag cgttaacgtt | 840 |
| gaagactgga aatgctgggc gcgttggcgt ttgatccgcg cccgggcccc ctggctgacc | 900 |
| cgcgccctgg tcgccgagga cttcgaattc tacggccgca cgcttaccgg cgcacagcag | 960 |

-continued

```
cttcgggacc gttggaagcg tggggtgtca ctggtggaga acctgatggg cgatgccgtc   1020
ggaaagctct atgtacaacg ccatttcccg ccggatgcca agtcccgcat cgacaccctg   1080
gtggacaacc tgcaggaggc gtatcggatc agcatcagcg agctggattg gatgacgccg   1140
cagacccggc aacgcgcgct agcgaagctg aacaagttca ccgccaaagt cggctatccg   1200
atcaagtggc gcgactactc gaagctggcg atcgaccgcg acgacctcta cggtaacgtc   1260
cagcgcggct acgccgtcaa ccatgaccgc gagctagcca agcttttcgg cccggtcgac   1320
cgcgacgagt ggttcatgac accacaaacc gtcaacgcct actacaaccc ggggatgaac   1380
gaaatcgtct tccccgcagc gattttacag ccaccatttt tcgatccgca ggccgacgag   1440
gccgccaact acgcgggat cggggcggtg atcgggcacg agatcgggca cggtttcgac   1500
gatcagggcg ccaaatacga cggcgacggc aatctggtcg attggtggac cgacgacgat   1560
cgcaccgagt cgccgcccg caccaaagcg ttgatcgagc agtaccacgc ttacacgccg   1620
cgcgatctcg tcgaccaccc cggcccgcct catgtgcaag gcgcgttcac cataggcgag   1680
aacatcggcg acctgggcgg gctgtcgatc gccctgctgg cttaccagct ctcgctgaac   1740
ggcaaccccg ctccggttat cgacgggctg accggcatgc aacgggtgtt cttcggctgg   1800
gcacaaatat ggcgaaccaa atcgcgtgca gccgaagcaa tccgccggtt ggcggtcgat   1860
ccgcactccc cgccggagtt ccggtgcaac ggtgtggttc gcaacgtgga cgcttttttat   1920 caggccttcg acgtcaccga ggatgacgcg ctgtttctgg acccgcagcg cagggtccgg   1980
atctggaac                                                          1989
```

<210> SEQ ID NO 35
<211> LENGTH: 275
<212> TYPE: PRT
<213> ORGANISM: Mycobacterium tuberculosis

<400> SEQUENCE: 35

```
Met Ser Asn Ala Pro Glu Pro Asp Arg Ser Ala Gly Glu Ser Gly Ser
1               5                   10                  15

Glu Pro Ala Gly Glu Arg Ser Ala Asp Pro Gly Glu Glu Arg Thr Glu
            20                  25                  30

Ser Tyr Pro Leu Val Pro His Asp Ala Glu Thr Glu Thr Val Val Ile
        35                  40                  45

Thr Thr Ser Asp Asn Asp Ala Ala Val Thr Gln Pro Glu Ala Gln Arg
    50                  55                  60

Glu Arg Arg Phe Thr Ala Pro Gly Phe Asp Ala Lys Glu Thr Gln Val
65                  70                  75                  80

Ile Val Thr Ala His Glu Ala Ala Thr Glu Val Phe Gln Thr Asn Gln
                85                  90                  95

Ala Pro Thr Thr Pro Pro Arg Met Pro Thr Gly Met Pro Pro Lys Thr
            100                 105                 110

Ala Val Pro Gln Ser Ile Pro Pro Arg Thr Glu Ala Thr Ser Val Arg
        115                 120                 125

Gln Arg Thr Trp Gly Trp Ala Leu Ala Val Val Val Ile Val Leu Ala
    130                 135                 140

Leu Ala Ala Ile Ala Ile Leu Gly Thr Val Leu Thr Arg Gly Lys
145                 150                 155                 160

His Ser Lys Met Ser Gln Glu Asp Gln Val Arg Gln Ala Ile Gln Ser
                165                 170                 175

Leu Asp Ile Ala Ile Gln Thr Gly Asp Leu Thr Ala Leu Arg Ser Leu
```

```
            180             185             190
Thr Cys Gly Ser Thr Arg Asp Gly Tyr Val Asp Tyr Asp Glu Arg Asp
        195                 200                 205

Trp Ala Glu Thr Tyr Arg Arg Val Ser Ala Ala Lys Gln Tyr Pro Val
        210                 215                 220

Ile Ala Ser Ile Asp Gln Val Val Asn Gly Ala His Ala Glu Ala
225                 230                 235                 240

Asn Val Thr Thr Phe Met Ala Phe Asp Pro Gln Val Arg Ser Thr Arg
                    245                 250                 255

Ser Leu Asp Leu Gln Phe Arg Asp Gln Trp Lys Ile Cys Gln Ser
            260                 265                 270

Ser Ser Asn
        275

<210> SEQ ID NO 36
<211> LENGTH: 825
<212> TYPE: DNA
<213> ORGANISM: Mycobacterium tuberculosis

<400> SEQUENCE: 36
atgtccaacg cacccgagcc agaccgctca gccggtgaat ccgggagcga accggccggc     60
gagcggtccg ccgatcctgg cgaggaacgc accgaaagct accccctggt gcctcacgac    120
gccgaaaccg agaccgtggt gatcaccacc tccgacaacg atgccgcggt tacgcaaccg    180
gaagcgcagc gcgaacgccg tttcaccgcg cccggcttcg acgccaagga gacccaggtg    240
atcgtcacgg cccacgaggc agccaccgag gttttccaaa ccaaccaggc gccgaccacc    300
ccgccgcgga tgccaaccgg aatgcccccg aaaactgctg tgccacaatc aatcccgcca    360
cggacggagg cgacgtcagt ccggcaacgc acctgggct gggcgctggc ggtggtagtg     420
atcgtgctgg cgttggcggc aatcgcgatc ctgggcaccg tgctgctgac cgcggcaaa     480 cattcgaaga tgtcgcagga agatcaggtg cggcaggcca tccagagctt ggacatcgcc    540
atccagaccg cgacctgac cgcgctgcgt tccctgactt gtggctccac cgcgatggc     600 tacgtggatt atgacgagcg tgattgggcc gaaacctatc gccgggtttc ggcggccaaa    660
caatatccgg tcatcgccag catcgaccag gtcgtcgtca acggcgcgca cgccgaggcc    720
aatgtcacca ctttcatggc gttcgatccc caggtccgct cgacccgcag cctcgaccta    780
cagtttcgcg acgatcagtg gaagatctgc cagtcctcca gcaac                   825

<210> SEQ ID NO 37
<211> LENGTH: 158
<212> TYPE: PRT
<213> ORGANISM: Mycobacterium tuberculosis

<400> SEQUENCE: 37

Val Ala Leu Ser Ala Asp Ile Val Gly Met His Tyr Arg Tyr Pro Asp
1               5                   10                  15

His Tyr Glu Val Glu Arg Glu Lys Ile Arg Glu Tyr Ala Val Ala Val
                20                  25                  30

Gln Asn Asp Asp Ala Trp Tyr Phe Glu Glu Asp Gly Ala Ala Glu Leu
            35                  40                  45

Gly Tyr Lys Gly Leu Leu Ala Pro Leu Thr Phe Ile Cys Val Phe Gly
        50                  55                  60

Tyr Lys Ala Gln Ala Ala Phe Phe Lys His Ala Asn Ile Ala Thr Ala
65                  70                  75                  80
```

-continued

Glu Ala Gln Ile Val Gln Val Asp Gln Val Leu Lys Phe Glu Lys Pro
            85                  90                  95

Ile Val Ala Gly Asp Lys Leu Tyr Cys Asp Val Tyr Val Asp Ser Val
            100                 105                 110

Arg Glu Ala His Gly Thr Gln Ile Ile Val Thr Lys Asn Ile Val Thr
            115                 120                 125

Asn Glu Glu Gly Asp Leu Val Gln Glu Thr Tyr Thr Thr Leu Ala Gly
            130                 135                 140

Arg Ala Gly Glu Asp Gly Glu Gly Phe Ser Asp Gly Ala Ala
145                 150                 155

<210> SEQ ID NO 38
<211> LENGTH: 474
<212> TYPE: DNA
<213> ORGANISM: Mycobacterium tuberculosis

<400> SEQUENCE: 38
gtggcgttga gcgcagacat cgttgggatg cattaccggt atcccgacca ctacgaggtg    60
gagcgggaga agattcgcga gtacgccgtc gccgttcaaa acgacgacgc gtggtatttc   120
gaggaggacg gcgccgccga actcgggtat aagggcttgc tggctccgtt gacgtttatc   180
tgtgtgttcg gctacaaggc ccaggcggcg ttcttcaagc atgcgaacat cgcgaccgcg   240
gaggcgcaga tcgtccaggt agaccaagtg ctgaaattcg agaaaccgat cgtggcgggc   300
gacaagctgt actgcgacgt ctatgtggat cggtgcgtg aggcgcacgg cacccagatc   360
atcgtgacca gaacatcgt caccaacgag aaggtgacc tcgtgcagga gacctatacg   420
accctggcgg gccgtgccgg cgaggatgga gagggatttt ctgatggcgc tgcg          474

<210> SEQ ID NO 39
<211> LENGTH: 318
<212> TYPE: PRT
<213> ORGANISM: Mycobacterium tuberculosis

<400> SEQUENCE: 39

Val His Arg Leu Arg Ala Ala Glu His Pro Arg Pro Asp Tyr Val Leu
 1               5                  10                  15

Leu His Ile Ser Asp Thr His Leu Ile Gly Gly Asp Arg Arg Leu Tyr
            20                  25                  30

Gly Ala Val Asp Ala Asp Arg Leu Gly Glu Leu Leu Glu Gln Leu
            35                  40                  45

Asn Gln Ser Gly Leu Arg Pro Asp Ala Ile Val Phe Thr Gly Asp Leu
    50                  55                  60

Ala Asp Lys Gly Glu Pro Ala Ala Tyr Arg Lys Leu Arg Gly Leu Val
65                  70                  75                  80

Glu Pro Phe Ala Ala Gln Leu Gly Ala Glu Leu Val Trp Val Met Gly
            85                  90                  95

Asn His Asp Asp Arg Ala Glu Leu Arg Lys Phe Leu Leu Asp Glu Ala
            100                 105                 110

Pro Ser Met Ala Pro Leu Asp Arg Val Cys Met Ile Asp Gly Leu Arg
            115                 120                 125

Ile Ile Val Leu Asp Thr Ser Val Pro Gly His His Gly Glu Ile
            130                 135                 140

Arg Ala Ser Gln Leu Gly Trp Leu Ala Glu Glu Leu Ala Thr Pro Ala
145                 150                 155                 160

Pro Asp Gly Thr Ile Leu Ala Leu His His Pro Pro Ile Pro Ser Val
            165                 170                 175

```
Leu Asp Met Ala Val Thr Val Glu Leu Arg Asp Gln Ala Ala Leu Gly
            180                 185                 190

Arg Val Leu Arg Gly Thr Asp Val Arg Ala Ile Leu Ala Gly His Leu
        195                 200                 205

His Tyr Ser Thr Asn Ala Thr Phe Val Gly Ile Pro Val Ser Val Ala
    210                 215                 220

Ser Ala Thr Cys Tyr Thr Gln Asp Leu Thr Val Ala Ala Gly Gly Thr
225                 230                 235                 240

Arg Gly Arg Asp Gly Ala Gln Gly Cys Asn Leu Val His Val Tyr Pro
                245                 250                 255

Asp Thr Val Val His Ser Val Ile Pro Leu Gly Gly Gly Glu Thr Val
            260                 265                 270

Gly Thr Phe Val Ser Pro Gly Gln Ala Arg Arg Lys Ile Ala Glu Ser
        275                 280                 285

Gly Ile Phe Ile Glu Pro Ser Arg Arg Asp Ser Leu Phe Lys His Pro
    290                 295                 300

Pro Met Val Leu Thr Ser Ser Ala Pro Arg Ser Pro Val Asp
305                 310                 315

<210> SEQ ID NO 40
<211> LENGTH: 954
<212> TYPE: DNA
<213> ORGANISM: Mycobacterium tuberculosis

<400> SEQUENCE: 40
gtgcatagac ttagggccgc ggagcatccg cggccggatt acgttctctt acatatcagc        60
gacactcatc tcatcggggg ggatcgtcgg ctctacgggg cggtggacgc cgacgaccgg       120
ctgggcgaac tgctcgaaca gttgaaccaa tccggccttc gtcccgatgc gatcgtcttc       180
accggcgatt tggccgataa gggcgaaccg gcggcatacc gcaagctccg aggcctggtc       240
gagccgttcg cggcgcagtt gggcgccgag ctcgtctggg tgatgggtaa ccacgacgac       300
cgggccgaac tacgcaaatt cttgctggac gaagcgccat cgatggcgcc gctagaccgg       360
gtgtgcatga tcgacggtct gcgcatcatc gtgttggata cctcggtacc cggacatcat       420
cacggcgaaa tccgcgcgtc ccaattgggt tggcttgctg aagagttggc cacgccagcg       480
ccggacggca ccattttggc gttgcatcat ccgccgattc cgagtgtttt ggatatggcc       540
gtcacggtgg agctgcgcga ccaggctgcg cttgggcgag tgctgcgggg cactgacgtt       600
cgcgccattt tggccgggca cctgcactac tcgacgaatg ccaccttcgt cgggatccca       660
gtgtcggttg cctcggcgac ttgctacacc caggacctga ccgtcgctgc tggaggaacg       720
cgtggcagag acggcgccca aggttgcaac ctggtgcacg tctatccgga caccgtcgtg       780
cattcggtga ttccgctggg cggcggagaa acggtcggca cctttgtctc acccgggcag       840
gcgcgacgca aaatcgccga gagcggcatt ttcatcgaac cgtcgcgtcg cgattcgcta       900
ttcaagcacc ctccgatggt gctgacgtcc tcggcaccgc gaagtcccgt cgac            954

<210> SEQ ID NO 41
<211> LENGTH: 129
<212> TYPE: PRT
<213> ORGANISM: Mycobacterium tuberculosis

<400> SEQUENCE: 41

Leu Asn Ala Ala Met Asn Leu Lys Arg Glu Phe Val His Arg Val Gln
1               5                   10                  15
```

Arg Phe Val Val Asn Pro Ile Gly Arg Gln Leu Pro Met Thr Met Leu
            20                  25                  30

Glu Thr Ile Gly Arg Lys Thr Gly Gln Pro Arg Arg Thr Ala Val Gly
        35                  40                  45

Gly Arg Val Val Asp Asn Gln Phe Trp Met Val Ser Glu His Gly Glu
    50                  55                  60

His Ser Asp Tyr Val Tyr Asn Ile Lys Ala Asn Pro Ala Val Arg Val
65                  70                  75                  80

Arg Ile Gly Gly Arg Trp Arg Ser Gly Thr Ala Tyr Leu Leu Pro Asp
                85                  90                  95

Asp Asp Pro Arg Gln Arg Leu Arg Gly Leu Pro Arg Leu Asn Ser Ala
            100                 105                 110

Gly Val Arg Ala Met Gly Thr Asp Leu Leu Thr Ile Arg Val Asp Leu
            115                 120                 125

Asp

<210> SEQ ID NO 42
<211> LENGTH: 387
<212> TYPE: DNA
<213> ORGANISM: Mycobacterium tuberculosis

<400> SEQUENCE: 42
ttgaatgcag ctatgaatct caagcgggaa ttcgtccatc gcgtgcaacg gttcgtggtc      60
aatccaatcg gccggcaact gccgatgacc atgctcgaaa ccatcggccg caaaacggga     120
cagccgcggc gtaccgcggt gggcgggcgc gtcgtagaca accagttctg gatggtgtcc     180
gagcacggcg agcattccga ttacgtctac aacatcaagg ccaaccccgc cgtgcgggtc     240
cgcatcggcg gccgatggcg cagtgggacc gcctacctgc tacccgacga cgatccgagg     300
cagcggctgc gcggcctacc ccggctgaac agtgccggcg tacgcgcgat gggcaccgac     360
ttgctgacca tccgggtgga tttggac                                          387

<210> SEQ ID NO 43
<211> LENGTH: 27
<212> TYPE: PRT
<213> ORGANISM: Mycobacterium tuberculosis

<400> SEQUENCE: 43

Met Pro Ala Ser Ser Leu Gly Thr Gly Ser Pro Ala Ala Asp Arg Leu
1               5                   10                  15

Asp Ala Thr His Glu Arg Arg Arg Glu Val Ile
            20                  25

<210> SEQ ID NO 44
<211> LENGTH: 81
<212> TYPE: DNA
<213> ORGANISM: Mycobacterium tuberculosis

<400> SEQUENCE: 44
atgccggcat cgagtctggg taccgggtcg cccgccgccg acaggctcga cgccacccac      60
gagcgtcggc gtgaggtcat t                                                 81

<210> SEQ ID NO 45
<211> LENGTH: 287
<212> TYPE: PRT
<213> ORGANISM: Mycobacterium tuberculosis

<400> SEQUENCE: 45

```
Val Thr Val Ser Asp Ser Pro Ala Gln Arg Gln Thr Pro Pro Gln Thr
1               5                   10                  15

Pro Gly Gly Thr Ala Pro Arg Ala Arg Thr Ala Ala Phe Phe Asp Leu
            20                  25                  30

Asp Lys Thr Ile Ile Ala Lys Ser Ser Thr Leu Ala Phe Ser Lys Pro
        35                  40                  45

Phe Phe Ala Gln Gly Leu Leu Asn Arg Arg Ala Val Leu Lys Ser Ser
    50                  55                  60

Tyr Ala Gln Phe Ile Phe Leu Leu Ser Gly Ala Asp His Asp Gln Met
65                  70                  75                  80

Asp Arg Met Arg Thr His Leu Thr Asn Met Cys Ala Gly Trp Asp Val
                85                  90                  95

Ala Gln Val Arg Ser Ile Val Asn Glu Thr Leu His Asp Ile Val Thr
            100                 105                 110

Pro Leu Val Phe Ala Glu Ala Ala Asp Leu Ile Ala Ala His Lys Leu
            115                 120                 125

Cys Gly Arg Asp Val Val Val Ser Ala Ser Gly Glu Glu Ile Val
        130                 135                 140

Gly Pro Ile Ala Arg Ala Leu Gly Ala Thr His Ala Met Ala Thr Arg
145                 150                 155                 160

Met Ile Val Glu Asp Gly Lys Tyr Thr Gly Glu Val Ala Phe Tyr Cys
                165                 170                 175

Tyr Gly Glu Gly Lys Ala Gln Ala Ile Arg Glu Leu Ala Ala Ser Glu
            180                 185                 190

Gly Tyr Pro Leu Glu His Cys Tyr Ala Tyr Ser Asp Ser Ile Thr Asp
        195                 200                 205

Leu Pro Met Leu Glu Ala Val Gly His Ala Ser Val Val Asn Pro Asp
210                 215                 220

Arg Gly Leu Arg Lys Glu Ala Ser Val Arg Gly Trp Pro Val Leu Ser
225                 230                 235                 240

Phe Ser Arg Pro Val Ser Leu Arg Asp Arg Ile Pro Ala Pro Ser Ala
            245                 250                 255

Ala Ala Ile Ala Thr Thr Ala Ala Val Gly Ile Ser Ala Leu Ala Ala
        260                 265                 270

Gly Ala Val Thr Tyr Ala Leu Leu Arg Arg Phe Ala Phe Gln Pro
        275                 280                 285

<210> SEQ ID NO 46
<211> LENGTH: 861
<212> TYPE: DNA
<213> ORGANISM: Mycobacterium tuberculosis

<400> SEQUENCE: 46
gtgaccgtct ccgactcgcc cgcccagcgg caaaccccac cgcaaacacc gggaggcacc      60
gctccgcgag cccgcaccgc ggccttttc gacctggaca agaccatcat tgccaagtcc     120
agcacactgg cgttcagcaa acctttcttc gctcagggac tgctcaaccg ccgcgccgtg     180
ctgaagtcca gctacgcgca gttcatcttt ctgctgtccg gtgctgacca tgaccagatg     240
gaccggatgc gcacccacct gaccaacatg tgcgccggtt gggacgtagc ccaggtgcgg     300
tcgatagtca cgaaaccct gcacgacatc gtgaccccac tggtgttcgc cgaggccgcg     360
gacctcatcg ccgcccacaa gctgtgcggc cgcgacgtcg tggtggtctc ggcttcgggc     420
gaggagatct cggcccgat cgcccgcgcg ctggcgcga cccatgcgat ggcgacccgg     480
atgatcgtcg aggacggcaa gtacacaggc gaggtcgcgt tctactgcta cggcgaaggt     540
```

-continued

```
aaggcgcaag  ccatccgtga  gctggctgcc  agtgagggct  acccgctgga  acactgctac     600
gcgtactccg  actcgatcac  cgatctgccg  atgcttgagg  cggttgggca  tgcctcggtg     660
gtcaaccctg  atcgcggctt  acgaaaggaa  gccagcgtgc  gcggttggcc  cgtgttgtcg     720
ttctctcggc  cggtgtcgct  gcgcgaccgg  atcccggcac  cgtcagccgc  ggcgatcgcc     780
acgactgcgg  cggtgggtat  cagcgcccta  gccgccggcg  cggtcaccta  cgcgctacta     840
cgccgcttcg  cgtttcagcc  c                                                  861
```

MYCOBACTERIAL GENES DOWN-REGULATED DURING LATENCY

The present invention relates to a method of identifying a gene in *mycobacteria* the expression of which is down-regulated during mycobacterial latency, to the isolated peptide products, variants, derivatives or fragments thereof and to inhibitors thereof, to antibodies that bind to said peptides, variants, derivatives or fragments, to DNA and RNA vectors that express said polypeptide, variants, derivatives or fragments, to attenuated *mycobacteria* in which the activity of at least one of said genes has been modified, to vaccines against mycobacterial infections, and to methods of detecting the presence of a mycobacterial infection.

Many microorganisms are capable of forming intracellular infections. These include: infections caused by species of *Salmonella, Yersinia, Shigella, Campylobacter, Chlamydia* and *Mycobacteria*. Some of these infections are exclusively intracellular, others contain both intracellular and extracellular components. However, it is the intracellular survival cycle of bacterial infection which is suspected as a main supportive factor for disease progression.

Generally, these microorganisms do not circulate freely in the body, for example, in the bloodstream, and are often not amenable to drug treatment regimes. Where drugs are available, this problem has been exacerbated by the development of multiple drug resistant microorganisms.

A number of factors have contributed to the problem of microbial resistance. One is the accumulation of mutations over time and the subsequent horizontal and vertical transfer of the mutated genes to other organisms. Thus, for a given pathogen, entire classes of antibiotics have been rendered inactive. A further factor has been the absence of a new class of antibiotics in recent years. The emergence of multiple drug-resistant pathogenic bacteria represents a serious threat to public health and new forms of therapy are urgently required.

For similar reasons, vaccine therapies have not proved effective against such intracellular microorganisms. Also, increased systemic concentration of antibiotics to improve bioavailability within cells may result in severe side effects.

*Mycobacterium tuberculosis* (TB) and closely related species make up a small group of *mycobacteria* known as the *Mycobacterium tuberculosis* complex (MTC). This group comprises five species *M. tuberculosis, M. microti, M. bovis, M. caneti*, and *M. africanum* which are the causative agent in the majority of *tuberculosis* (TB) cases throughout the world.

*M. tuberculosis* is responsible for more than three million deaths a year world-wide. Other *mycobacteria* are also pathogenic in man and animals, for example *M. avium* subsp. *paratuberculosis* which causes Johne's disease in ruminants, *M. bovis* which causes *tuberculosis* in cattle, *M. avium* and *M. intracellulare* which cause *tuberculosis* in immunocompromised patients (eg. AIDS patients, and bone marrow transplant patients) and *M. leprae* which causes leprosy in humans. Another important mycobacterial species is *M. vaccae*.

*M. tuberculosis* infects macrophage cells within the body. Soon after macrophage infection, most *M. tuberculosis* bacteria enter and replicate within cellular phagosome vesicles, where the bacteria are sequestered from host defences and extracellular factors.

It is the intracellular survival and multiplication or replication of bacterial infection which is suspected as a main supportive factor for mycobacterial disease progression.

A number of drug therapy regimens have been proposed for combatting *M. tuberculosis* infections, and currently combination therapy including the drug isoniazid has proved most effective. However, one problem with such treatment regimes is that they are long-term, and failure to complete such treatment can promote the development of multiple drug resistant microorganisms.

A further problem is that of providing an adequate bioavailability of the drug within the cells to be treated. Whilst it is possible to increase the systemic concentration of a drug (eg. by administering a higher dosage) this may result in severe side effects caused by the increased drug concentration.

The effectiveness of vaccine prevention against *M. tuberculosis* has varied widely. The current *M. tuberculosis* vaccine, BCG, is an attenuated strain of *M. bovis*. It is effective against severe complications of TB in children, but it varies greatly in its effectiveness in adults particularly across ethnic groups. BCG vaccination has been used to prevent tuberculous meningitis and helps prevent the spread of *M. tuberculosis* to extra-pulmonary sites, but does not prevent infection.

The limited efficacy of BCG and the global prevalence of TB has led to an international effort to generate new, more effective vaccines. The current paradigm is that protection will be mediated by the stimulation of a Th1 immune response.

BCG vaccination in man was given orally when originally introduced, but that route was discontinued because of loss of viable BCG during gastric passage and of frequent cervical adenopathy. In experimental animal species, aerosol or intratracheal delivery of BCG has been achieved without adverse effects, but has varied in efficacy from superior protection than parenteral inoculation in primates, mice and guinea pigs to no apparent advantage over the subcutaneous route in other studies.

Conventional mycobacterial vaccines, including BCG, protect against disease and not against infection. Ideally a new mycobacterial vaccine will impart sterile immunity, and a post-exposure vaccine capable of boosting the immune system to kill latent *mycobacteria* or prevent reactivation to active disease-causing microorganisms would also be valuable against latent infection.

There is therefore a need for an improved and/or alternative vaccine or therapeutic agent for combatting mycobacterial infections.

An additional major problem associated with the control of mycobacterial infections, especially *M. tuberculosis* infections, is the presence of a large reservoir of asymptomatic individuals infected with *mycobacteria*. Dormant *mycobacteria* are even more resistant to front-line drugs.

Infection with *mycobacteria* (eg. *M. tuberculosis*) rarely leads to active disease, and most individuals develop a latent infection which may persist for many years before reactivating to cause disease (Wayne, 1994). The current strategy for controlling such infection is early detection and treatment of patients with active disease. Whilst this is essential to avoid deaths and control transmission, it has no effect on eliminating the existing reservoir of infection or on preventing new cases of disease through reactivation.

Furthermore, conventional methods for the detection of a latent mycobacterial infection by skin testing may be compromised. For example, current TB detection methods based on tuberculin skin testing are compromised by BCG vaccination and by exposure to environmental *mycobacteria*.

Thus, new strategies are required for more effective diagnosis, treatment and prevention of mycobacterial latent infection.

To develop specific strategies for addressing latent mycobacterial infection it is necessary to elucidate the physiological, biochemical and molecular properties of these microorganisms.

However, at present, there is no suitable in vivo model for studying mycobacterial latent infection and such a model is unlikely to provide sufficient microbial material to enable detailed analysis of the physiological and molecular changes that occur.

In this respect, conventional mycobacterial culture systems for analysing gene and protein expression profiles have been based on simple, crude batch-type systems, such as those described in Sherman, D. R et al (2001) PNAS Vol. 98, No. 13, pp. 7534-7539; Imboden, P. (1998) Gene 213, pp. 107-117; Boon, C. et al (2001) J. Bacteriol. Vol. 183, No. 8, pp. 2672-2676; Cunningham, A. F et al (1998), J. Bacteriol. Vol. 180, No. 4, pp. 801-808; and Murugasu-Oei, B. et al (1999), Mol. Gen. Genet., Vol. 262, pp. 677-682. In these crude batch systems, mycobacterial growth follows a typical sigmoid growth curve involving an exponential growth phase and a stationary phase. The transition from exponential phase to stationary phase involves rapid and transient switches in terms of gene and protein expression, which switches are initiated by a complex set of undefined or poorly defined interactive stimuli as the *mycobacteria* become starved of essential nutrients.

In summary, studies to date have used either static cultures that allow tubercle bacilli to generate oxygen-depletion-gradients and enter a non-replicating persistent state in the sediment layer, or agitated sealed liquid cultures (Wayne and Lin, 1982; Cunningham and Spreadbury, 1998; Wayne and Hayes, 1996). Transition to a non-replicating persistent state in these models coincides with a shift-down to glyoxylate metabolism, resistance to isoniazid and rifampicin and susceptibility to the anaerobic bactericidal action of metronidazole (Wayne and Hayes, 1996).

Such studies are poorly defined and controlled, and experiments relying on self-generated oxygen-depletion gradients have yielded inconsistent results. Furthermore, these studies do not consider other physicochemical stimuli that may be important in vivo, and have been conducted over a short duration, in many cases 2-3 weeks.

In view of the above, there is a need for a defined and controlled model for studying mycobacterial (eg. TB) persistence, which simulates key features of the in vivo environment.

According to a first aspect of the invention there is provided an isolated mycobacterial peptide, or a fragment or derivative or variant thereof, wherein the peptide is encoded by a mycobacterial gene the expression of which gene is down-regulated during a stationary phase culture of *mycobacteria* under nutrient-starving culture conditions when compared with an exponential phase culture of *mycobacteria* under culture conditions that are not nutrient-starving and which support exponential growth of said *mycobacteria*.

The following various embodiments (eg. preferred culture conditions, and sampling times) described for the first aspect of the present invention apply equally to the second and subsequent aspects of the present invention.

During infection, *mycobacteria* (eg. *M. tuberculosis*) encounter a dynamic host environment and modulate the expression of genes required for infection.

The selection conditions of the present invention permit identification of mycobacterial genes that are not required for maintenance of mycobacterial latency. Such selection conditions therefore permit the identification of genes that may be expressed in vivo during active mycobacterial infection, or during/following re-activation of a *mycobacterium* from a latent state. Active infection refers to an infectious state in which the *mycobacteria* demonstrate high metabolic activity and undergo cell division. Latency is discussed in more detail below.

The term latency is synonymous with persistence, and describes a reversible state of low metabolic activity in which mycobacterial cells can survive for extended periods without cell division. During latency (ie. latent infection), the clinical symptoms associated with a mycobacterial infection do not become manifest, and the host suffers no significant ill.

However, re-activation of latent *mycobacteria* may be induced by environmental stimuli, resulting in the development of an active mycobacterial infection with the associated clinical symptoms. The present inventors believe that stimuli such as an increase in nutrient availability, optionally together with an increase in the local dissolved oxygen concentration may induce re-activation.

For example, re-activation of latent *mycobacteria* may occur when previously limiting nutrients, and optionally oxygen, become available. This may happen, for example, following breakdown of a mycobacterial infection granuloma structure.

Studies of TB pathogenesis have established that tubercle bacilli reside in a number of different locations in the lung, for example lining the walls of cavitary lesions where the close proximity to bronchioles provides a source of air; within macrophages where oxygen availability may be more limited or within granulomas. Studies of granuloma structure, where the bacilli are encased by layers of macrophages and lymphocytes and may persist for prolonged periods, have led scientists to the conclusion that the environment within a granuloma is most likely to be anoxic. Therefore TB may encounter a range of atmospheric conditions from the point of transmission and inhalation through to long-term persistence in a granuloma.

The present inventors believe that *mycobacteria* such as *M. tuberculosis* must be able to adapt and respond to changes in nutrient, and optionally oxygen, availability in order to cause infection. The initial stages of infection, which include dissemination and phagocytosis, occur under aerobic conditions, and tubercle bacilli replicate rapidly in the aerobic environments of the cavitary lesion as well as within macrophages.

In vitro studies have demonstrated that *mycobacteria* such as *M. tuberculosis* can adapt and survive under nutrient- and oxygen-depleted conditions, and can grow over a range of oxygen tensions. Adaptation to carbon starvation, and optionally to a low dissolved oxygen tension, triggers transition to a non-replicating persistent state in vitro that may be analogous to latency in vivo.

Antigens repressed during latency and that have been identified according to the present invention may play an early and important role in the development of an effective immune response against replicating bacilli during the active stages of disease, and consequently represent good vaccine candidates. In addition, genes repressed under latency conditions are important therapeutic targets for preventing the establishment, spread and reactivation of disease. The identified genes are likely to be required for re-activation of latent *mycobacteria*, and replication of said re-activated bacilli. They are therefore key targets for the development of therapeutic agents and post-exposure vaccines to prevent re-activation of latent infection. Alternatively, said genes may be exploited in a treatment regime designed to trigger re-activation of latent bacilli. When re-activated, tubercle bacilli are more susceptible to treatment regimes. Thus, the antigens and genes of the present invention may form the basis for vaccines against pre- and post-infections by *mycobacteria*.

The term "nutrient-starving" in the context of the present invention means that the concentration of the primary carbon, and preferably the primary energy source, is insufficient to support optimal "exponential growth" of the *mycobacteria*. "Nutrient-starving" is a term that is generally associated with the stationary phase of a batch culture growth curve, or with the onset of late exponential/early stationary phase when the concentration of carbon is approaching depletion and starts to restrict the growth rate. Essential nutrients other than carbon (eg. nitrogen, iron, and oxygen) may also limit growth. Under such conditions the *mycobacteria* become metabolically stressed, rather than simply reduced in growth rate. By comparison, "nutrient limiting" is a term associated with continuous culture where growth is controlled/limited by the rate of addition of an essential nutrient to the culture system.

In more detail, exponential growth is that period of growth that is associated with a logarithmic increase in mycobacterial cell mass (also known as the "log" phase) when the bacteria are multiplying at their maximum specific growth rate for the prevailing culture conditions. During this period of growth the concentrations of essential nutrients diminish and those of end-products increase. However, once the primary carbon and/or primary energy source falls to below a critical level, it is no longer possible for all of the mycobacterial cells within the culture to obtain sufficient carbon and/or energy needed to support optimal cellular function and cell division. Once this occurs, exponential growth stops and the *mycobacteria* enter stationary phase. Growth may also cease due to the accumulation of inhibitory secondary metabolites, or as a result of pH changes.

Carbon starvation normally refers to a supply of exogenous carbon that is insufficient to enable the bacteria to grow/replicate. However, there may be other energy sources (eg. endogenous reserves, secondary metabolites) that are available to maintain essential-cellular functions and viability without supporting growth. Thus, carbon starvation is associated with a stationary phase condition in which the carbon source has become depleted and bacterial growth has substantially ceased.

During onset of stationary phase, DNA synthesis may continue for some time after net increase in cell mass has ceased, and the *mycobacteria* may divide to produce cells small in size and low in RNA content. Many proteins, including extra-cellular enzymes, may be synthesized during the stationary phase.

The onset of stationary phase vis-a-vis addition of a mycobacterial inoculum to the culture vessel will depend on a number of factors such as the particular mycobacterial species/strain, the composition of the culture media (eg. the particular primary carbon and energy source), and the physical culture parameters employed.

However, as a guide, the end of exponential phase and the onset of stationary phase generally corresponds to that point in the growth phase associated with the maximum number of viable counts of *mycobacteria*.

In use of the present invention, the exponential phase mycobacterial cells are harvested from the culture vessel at a point in the growth phase before the maximum number of total viable counts has been achieved. This point in the growth phase may be mimicked under continuous culture conditions employing a steady state growth rate approximating $\mu_{max}$ and providing a generation time of approximately 18-24 hours. In a preferred embodiment, the exponential phase mycobacterial cells are harvested when a value of between 2 and 0.5 (more preferably between 1 and 0.5) log units of viable counts per ml of culture medium less than the maximum number of viable counts per ml of culture medium has been achieved. Thus, the "exponential" phase cells are generally harvested during mid-log phase.

For example, if the maximum viable count value is $1\times10^{10}$ per ml, then the "exponential" phase cells would be preferably harvested once a value of between $1\times10^8$ and $1\times10^{9.5}$ (more preferably between $1\times10^9$ and $1\times10^{9.5}$) viable counts per ml has been achieved. In the case of *M. tuberculosis*, this would be approximately 3-10, preferably 4-7 days post-inoculation.

Similarly, in use of the present invention, the stationary phase mycobacterial cells are harvested from the culture vessel at a point in the growth phase after the maximum number of total viable counts has been achieved. This point in the growth phase may be mimicked under continuous culture conditions supporting a generation time of at least 3 days. In a preferred embodiment, the stationary phase mycobacterial cells are harvested when the viable counts per ml of culture medium has fallen to between 0.5 and 3 (more preferably between 1.5 and 2.5) log units less than the maximum number of viable counts per ml of culture medium. Thus, the "stationary" phase cells are generally harvested during mid- to late-stationary phase.

For example, if the maximum viable count value is $1\times10^{10}$ per ml, then the stationary phase cells would be preferably harvested once the viable count number had fallen to a value of between $1\times10^{9.5}$ and $1\times10^{7}$ (more preferably between $1\times10^{8.5}$ and $1\times10^{7.5}$) viable counts per ml. In the case of *M. tuberculosis*, this would be approximately day 25-60, preferably day 30-50, more preferably day 40-50, post-inoculation. For mycobacteria generally, the stationary phase cells are preferably harvested at least 25, preferably at least 30, more preferably at least 40 days post-inoculation. Longer post-inoculation harvesting times of at least 100 days, even at least 150 days may be employed. The above harvesting times apply to all aspects of the present invention.

The preferred culture method employed by the present invention is that of batch fermenter culture. In contrast to the crude prior art Wayne-type, simple batch culture systems, the batch fermenter system, of the present invention permits careful monitoring of growth culture parameters such as pH, temperature, available nutrients, and dissolved oxygen tension (DOT). In particular, temperature and DOT may be strictly controlled.

Thus, in use of the present method it is possible to ensure that the principal latency induction parameter employed is starvation of the primary carbon, and preferably the starvation of the primary carbon and energy source. In contrast, the crude prior art, simple batch systems simultaneously expose the cultured *mycobacteria* to a complex range of interactive environmental stimuli, which stimuli may obscure or modify the cellular effects associated with a single, principal stimulus in isolation.

Thus, the present invention substantially avoids the accidental induction or up-regulation of genes which are solely responsive to other environmental switches may be substantially prevented. Accordingly, false-positive identification of genes that are down-regulated under conditions unrelated to carbon starvation and/or energy limitation may be substantially avoided.

Suitable media for culturing *mycobacteria* are described in Wayne, L. G. (1994) [in *Tuberculosis*: Pathogenesis, Protection, and Control published by the American Society for Microbiology, pp. 73-83]. These include Middlebrook 7H9

Medium [see Barker, L. P., et al. (1998) Molec. Microbiol., vol. 29 (5), pp. 1167-1177; and WO00/52139 in the name of the present Applicant].

In use of the method, the starting concentration of the primary carbon source (and preferably the primary energy source) is at least 0.5, preferably at least 1 gl$^{-1}$ of culture medium. Such concentrations are generally considered to be non nutrient-starving. Similarly, the onset of the stationary phase is generally associated with a primary carbon and energy source concentration of less than 0.5, preferably less than 0.2, and more preferably less than 0.1 gl$^{-1}$ of culture medium In a preferred embodiment, the primary carbon and energy source is glycerol. The starting concentration of this component is at least 1, preferably 1-3, more preferably approximately 2 gl$^{-1}$ of culture medium. The onset of stationary phase is associated with a concentration of less than 0.2, preferably less than 0.1 gl$^{-1}$ of culture medium.

Other primary carbon and energy sources may be employed such as glucose, pyruvate, and fatty acids (eg. palmitate, and butyrate). These sources may be employed at substantially the same concentrations as for glycerol.

The pH of the culture medium is preferably maintained between pH 6 and 8, more preferably between pH 6.5 and 7.5, most preferably at about pH 6.9.

In one embodiment, the dissolved oxygen tension (DOT) is maintained throughout the culture process at at least 40% air saturation when measured at 37° C., more preferably between 50 and 70% air saturation when measured at 37° C., most preferably at 50% air saturation when measured at 37° C.

The dissolved oxygen tension parameter is calculated by means of an oxygen electrode and conventional laboratory techniques at 37° C. Thus, 100% air saturation corresponds to a solution which is saturated with air, whereas 0% corresponds to a solution which has been thoroughly purged with an inert gas such as nitrogen. Calibration is performed under standard atmospheric pressure conditions and 37° C., and with conventional air comprising approximately 21% oxygen. Thus, the DOT values quoted in the present application concern DOT when measured at 37° C. and standard atmospheric pressure. A reference temperature and pressure is indicated, as DOT may vary with temperature and pressure.

In another embodiment of the present invention, latency may be induced by a combination of carbon and/or energy source starvation, and a low DOT.

In a preferred embodiment, the DOT is maintained at at least 40% air saturation, more preferably between 50 and 70% air saturation, until the mycobacterial culture has entered early-mid log phase. The DOT may be then lowered so as to become limiting, for example in increments over a 5 or 6 day period, and the culture maintained at a DOT of 0-10, preferably at a DOT of approximately 5% or less until the stationary phase cells are harvested.

The present inventors believe that the carbon and energy starvation, and optional low oxygen tension, induction conditions of the present invention are culture conditions that are conducive for a *mycobacterium* to express at least one gene that would be normally expressed in vivo during infection.

In use, it is preferred that those genes (ie. as represented by cDNAs in the detection assay) that are down-regulated by at least 1.5-fold under stationary phase, nutrient-starving conditions vis-a-vis exponential phase, non nutrient-starving conditions are selected. In more preferred embodiments, the corresponding down-regulation selection criterion is at least 2-fold, more preferably 3-fold, most preferably 4-fold. In further embodiments down-regulation levels of at least 10-fold, preferably 50-fold may be employed. The above down-regulation criteria apply to all aspects of the present invention.

The *mycobacterium* is selected from the species *M. phlei, M. smegmatis, M. africanum, M. caneti, M. fortuitum, M. marinum, M. ulcerans, M. tuberculosis, M. bovis, M. microti, M. avium, M. paratuberculosis, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae, M. caneti,* and *M. shimoidei*. Of particular interest are members of the MTC, preferably *M. tuberculosis*.

The term peptide throughout this specification is synonymous with protein.

Use of mycobacterial peptide compositions according to the present invention provide excellent vaccine candidates for targeting *mycobacteria* in patients infected with *mycobacteria*.

The terms "isolated," "substantially pure," and "substantially homogenous" are used interchangeably to describe a peptide which has been separated from components which naturally accompany it. A peptide is substantially pure when at least about 60 to 75% of a sample exhibits a single peptide sequence. A substantially pure peptide will typically comprise about 60 to 90% w/w of a protein sample, more usually about 95%, and preferably will be over about 99% pure. Peptide purity or homogeneity may be indicated by, for example, polyacrylamide gel electrophoresis of a protein sample, followed by visualizing a single polypeptide band upon staining the gel. Alternatively, higher resolution may be provided by using, for example, HPLC.

A peptide is considered to be isolated when it is separated from the contaminants which accompany it in its natural state. Thus, a peptide which is chemically synthesized or synthesized in a cellular system different from the cell from which it naturally originates will be substantially free from its naturally associated components.

The present invention provides peptides which may be purified from *mycobacteria* as well as from other types of cells transformed with recombinant nucleic acids encoding these peptides.

If desirable, the amino acid sequence of the proteins of the present invention may be determined by protein sequencing methods.

The terms "peptide", "oligopeptide", "polypeptide", and "protein" are used interchangeably and do not refer to a specific length of the product. These terms embrace post-translational modifications such as glycosylation, acetylation, and phosphorylation.

The term "fragment" means a peptide having at least five, preferably at least ten, more preferably at least twenty, and most preferably at least thirty-five amino acid residues of the peptide which is the gene product of the down-regulated gene in question. The fragment preferably includes at least one epitope of the gene product in question.

The term "variant" means a peptide or peptide fragment having at least seventy, preferably at least eighty, more preferably at least ninety percent amino acid sequence homology with the peptide that is the gene product of the down-regulated gene in question. An example of a "variant" is a peptide or peptide fragment of a down-regulated gene which contains one or more analogs of an amino acid (eg. an unnatural amino acid), or a substituted linkage. The terms "homology" and "identity" are considered synonymous in this specification. In a further embodiment, a "variant" may be a mimic of the peptide or peptide fragment, which mimic reproduces at least one epitope of the peptide or peptide fragment. The mimic may be, for example, a nucleic acid mimic, preferably a DNA mimic.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85:2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and www.ncbi.nlm.nih.gov of the National Center for Biotechnology Information].

In a preferred homology comparison, the identity exists over a region of the sequences that is at least 10 amino acid, preferably at least 20 amino acid, more preferably at least 30 amino acid residues in length.

The term "derivative" means a protein comprising the peptide (or fragment, or variant thereof) which peptide is the gene product of the down-regulated gene in question. Thus, a derivative may include the peptide in question, and a further peptide sequence which may introduce one or more additional epitopes. The further peptide sequence should preferably not interfere with the basic folding and thus conformational structure of the peptide in question. Examples of a "derivative" are a fusion protein, a conjugate, and a graft. Thus, two or more peptides (or fragments, or variants) may be joined together to form a derivative. Alternatively, a peptide (or fragment, or variant) may be joined to an unrelated molecule (eg. a second, unrelated peptide). Derivatives may be chemically synthesized, but will be typically prepared by recombinant nucleic acid methods. Additional components such as lipid, and/or polysaccharide, and/or polyketide components may be included.

All of the molecules "fragment", "variant" and "derivative" have a common antigenic cross-reactivity and/or substantially the same in vivo biological activity as the gene product of the down-regulated gene in question from which they are derived. For example, an antibody capable of binding to a fragment, variant or derivative would be also capable of binding to the gene product of the down-regulated gene in question. It is a preferred feature that the fragment, variant and derivative each possess the active site of the peptide which is the down-regulated peptide in question. Alternatively, all of the above embodiments of a peptide of the present invention share a common ability to induce a "recall response" of a T-lymphocyte which has been previously exposed to an antigenic component of a mycobacterial infection.

In a preferred embodiment, the peptide is selected from the group consisting of SEQ ID NO: 1, 3, 5, 7, 9, 11, 13, 15, 17, 19, 21, 23, 25, 27, 29, 31, 33, 35, 37, 39, 41, 43, and 45.

According to a second aspect of the present invention there is provided a method of identifying a mycobacterial gene the expression of which is down-regulated during mycobacterial latency, said method comprising:

culturing a first *mycobacterium* under culture conditions that are nutrient-starving and which do not support exponential growth of the first *mycobacterium*;

culturing a second *mycobacterium* under culture conditions that are not nutrient-starving and which support exponential growth of the second *mycobacterium*;

obtaining first and second mRNA populations from said first and second *mycobacteria* respectively, wherein said first mRNA population is obtained from the first *mycobacterium* which has been harvested during stationary phase and wherein said second mRNA is obtained from the second *mycobacterium* which has been harvested during exponential phase growth;

preparing first and second cDNA populations from said first and second mRNA populations respectively, during which cDNA preparation a detectable label is introduced into the cDNA molecules of the first and second cDNA populations;

isolating corresponding first and second cDNA molecules from the first and second cDNA populations, respectively;

comparing relative amounts of label or corresponding signal emitted from the label present in the isolated first and second cDNA molecules;

identifying a greater amount of label or signal provided by the isolated second cDNA molecule than that provided by the isolated first cDNA molecule; and identifying the first cDNA and the corresponding mycobacterial gene which is down-regulated during mycobacterial latency.

Reference to "down-regulated" embraces switched-off. A gene is switched-off when there is substantially no transcription of said gene.

Reference to gene throughout this specification embraces open reading frames (ORFs).

The term "corresponding first and second cDNA molecules from the first and second cDNA populations" refers to cDNAs having substantially the same nucleotide sequence. Thus, by isolating the cDNA copies relating to a given gene under each culture condition (ie. exponential phase, and stationary phase), it is possible to quantify the relative copy number of cDNA for that gene for each culture condition. Since each cDNA copy has been produced from an mRNA molecule, the cDNA copy number reflects the corresponding mRNA copy number for each culture condition, and thus it is possible to identify down-regulated genes.

In one embodiment, the first and second cDNA molecules are isolated from the corresponding first and second cDNA populations by hybridisation to an array containing immobilised DNA sequences which are representative of each known gene (or ORF) of a particular mycobacterial species' genome. Thus, a first cDNA may be considered "corresponding" to a second cDNA if both cDNAs hybridise to the same immobilised DNA sequence. Alternatively, representative DNA sequences from a particular mycobacterial strain, or from a number of different species and/or strains may be employed in the array.

In another embodiment, the first and second cDNAs are prepared by incorporation of a fluorescent label. The first and second cDNAs may incorporate labels which fluoresce at different wavelengths, thereby permitting dual fluorescence and simultaneous detection of two cDNA samples.

The type of label employed naturally determines how the output of the detection method is read. When using fluorescent labels, a confocal laser scanner is preferably employed.

According to one embodiment, fluorescently labelled cDNA sequences from stationary and exponential phase cultured systems were allowed to hybridise with a whole mycobacterial genome array. The first cDNA population was labelled with fluorescent label A, and the second cDNA population was labelled with fluorescent label B. The array was scanned at two different wavelengths corresponding to the excitable maxima of each dye and the intensity of the emitted light was recorded. Multiple arrays were then preferably prepared for each cDNA and a mean intensity value was calculated across the two cDNA populations for each spot with each dye, against which relative induction or up-regulation was quantified.

In addition to the above mRNA isolation and cDNA preparation and labelling, genomic DNA may be isolated from the first and second *mycobacteria*. Thus, in a preferred embodiment, labelled DNA is also prepared from the isolated DNA. The labelled DNA may be then included on each array as a control.

According to a third aspect of the present invention, there is provided an inhibitor of a mycobacterial peptide, wherein the peptide is encoded by a gene the expression of which is down-regulated during a stationary phase culture of *mycobacteria* under nutrient-starving culture conditions when compared with an exponential phase culture of *mycobacteria* under culture conditions that are not nutrient-starving and that support exponential growth of said *mycobacteria*, and wherein the inhibitor is capable of preventing or inhibiting the mycobacterial peptide from exerting its native biological effect.

Such inhibitors may be employed to prevent the onset of, or to cause a break in the period of mycobacterial latency (ie. induce re-activation). In this respect, *mycobacteria* are more susceptible to treatment regimens when in a non-latent state, and the combined use of drugs to kill latent *mycobacteria* (eg. TB) would significantly reduce the incidence of *mycobacteria* by targeting the reservoir for new disease and would thereby help reduce the problem of emerging drug-resistant strains.

The inhibitor may be a peptide, carbohydrate, synthetic molecule, or an analogue thereof. Inhibition of the mycobacterial peptide may be effected at the nucleic acid level (ie. DNA, or RNA), or at the peptide level. Thus, the inhibitor may act directly on the peptide. Alternatively, the inhibitor may act indirectly on the peptide by, for example, causing inactivation of the down-regulated mycobacterial gene.

In preferred embodiments, the inhibitor is capable of inhibiting one or more of the following: endoglucanase, endo-1,4-beta-glucanase, carboxymethyl cellulase, inorganic phosphate transporter protein, transcriptional regulatory protein, 50S ribosomal protein L3, ribosomal protein S1, 30S ribosomal protein S4, uroporphyrin III C-methyltransferase, uroporphyrinogen III methylase, urogen III methylase, crystathionine gamma synthase, O-succinylhomoserine[thiol]-lyase, and zinc metalloprotease.

In a further embodiment, the inhibitor may be an antibiotic capable of targeting the down-regulated mycobacterial gene identifiable by the present invention, or the gene product thereof. The antibiotic is preferably specific for the gene and/or gene product.

In a further embodiment, the inhibitor may act on a gene or gene product the latter of which interacts with the down-regulated gene. Alternatively, the inhibitor may act on a gene or gene product thereof upon which the gene product of the down-regulated gene acts.

Inhibitors of the present invention may be prepared utilizing the sequence information provided herein. For example, this may be performed by overexpressing the peptide, purifying the peptide, and then performing X-ray crystallography on the purified peptide to obtain its molecular structure. Next, compounds are created which have similar molecular structures to all or portions of the peptide or its substrate. The compounds may be then combined with the peptide and attached thereto so as to block one or more of its biological activities.

Also included within the invention are isolated or recombinant polynucleotides that bind to the regions of the mycobacterial chromosome containing sequences that are associated with down-regulation under carbon starvation and optionally low oxygen tension (ie. virulence), including antisense and triplex-forming polynucleotides. As used herein, the term "binding" refers to an interaction or complexation between an oligonucleotide and a target nucleotide sequence, mediated through hydrogen bonding or other molecular forces. The term "binding" more specifically refers to two types of internucleotide binding mediated through base-base hydrogen bonding. The first type of binding is "Watson-Crick-type" binding interactions in which adenine-thymine (or adenine-uracil) and guanine-cytosine base-pairs are formed through hydrogen bonding between the bases. An example of this type of binding is the binding traditionally associated with the DNA double helix and in RNA-DNA hybrids; this type of binding is normally detected by hybridization procedures.

The second type of binding is "triplex binding". In general, triplex binding refers to any type of base-base hydrogen bonding of a third polynucleotide strand with a duplex DNA (or DNA-RNA hybrid) that is already paired in a Watson-Crick manner.

In a preferred embodiment, the inhibitor may be an antisense nucleic acid sequence which is complementary to at least part of the inducible or up-regulatable gene.

The inhibitor, when in the form of a nucleic acid sequence, in use, comprises at least 15 nucleotides, preferably at least 20 nucleotides, more preferably at least 30 nucleotides, and most preferably at least 50 nucleotides.

According to a fourth aspect of the invention, there is provided an antibody that binds to a peptide encoded by a gene, or to a fragment or variant or derivative of said peptide, the expression of which gene is down-regulated during a stationary phase culture of *mycobacteria* under nutrient-starving culture conditions when compared with an exponential phase culture of *mycobacteria* under culture conditions that are not nutrient-starving.

The antibody preferably has specificity for the peptide in question, and following binding thereto may initiate coating of a *mycobacterium* expressing said peptide. Coating of the bacterium preferably leads to opsonization thereof. This, in turn, leads to the bacterium being destroyed. It is preferred that the antibody is specific for the *mycobacterium* (eg. species and/or strain) which is to be targeted.

In use, the antibody is preferably embodied in an isolated form.

Opsonization by antibodies may influence cellular entry and spread of *mycobacteria* in phagocytic and non-phagocytic cells by preventing or modulating receptor-mediated entry and replication in macrophages.

The peptides, fragments, variants or derivatives of the present invention may be used to produce antibodies, including polyclonal and monoclonal. If polyclonal antibodies are desired, a selected mammal (eg. mouse, rabbit, goat, horse, etc.) is immunized with an immunogenic polypeptide. Serum from the immunized animal is collected and treated according to known procedures. If serum containing polyclonal antibodies to a desired mycobacterial epitope contains antibodies to other antigens, the polyclonal antibodies may be purified by immunoaffinity chromatography.

Alternatively, general methodology for making monoclonal antibodies by hybridomas involving, for example, preparation of immortal antibody-producing cell lines by cell fusion, or other techniques such as direct transformation of B lymphocytes with oncogenic DNA, or transfection with Epstein-Barr virus may be employed.

The antibody employed in this aspect of the invention may belong to any antibody isotype family, or may be a derivative or mimic thereof. Reference to antibody throughout this specification embraces recombinantly produced antibody, and any part of an antibody which is capable of binding to a mycobacterial antigen.

In one embodiment the antibody belongs to the IgG, IgM or IgA isotype families.

In a preferred embodiment, the antibody belongs to the IgA isotype family. Reference to the IgA isotype throughout this specification includes the secretory form of this antibody (ie. sIgA). The secretory component (SC) of sIgA may be added in vitro or in vivo. In the latter case, the use of a patient's natural SC labelling machinery may be employed.

In one embodiment, the antibody may be raised against a peptide from a member of the MTC, preferably against *M. tuberculosis*.

In a preferred embodiment, the antibody is capable of binding to a peptide selected from the group consisting of SEQ ID NO: 1, 3, 5, 7, 9, 11, 13, 15, 17, 19, 21, 23, 25, 27, 29, 31, 33, 35, 37, 39, 41, 43, 45, (or a fragment, variant, or derivative thereof).

In a further embodiment, the antigen is an exposed component of a mycobacterial *bacillus*. In another embodiment, the antigen is a cell surface component of a mycobacterial *bacillus*.

The antibody of the present invention may be polyclonal, but is preferably monoclonal.

Without being bound by any theory, it is possible that following mycobacterial infection of a macrophage, the macrophage is killed and the bacilli are released. It is at this stage that the *mycobacteria* are considered to be most vulnerable to antibody attack. Thus, it is possible that the antibodies of the present invention act on released bacilli following macrophage death, and thereby exert a post-infection effect.

It is possible that the passive protection aspect (ie. delivery of antibodies) of the present invention is facilitated by enhanced accessibility of the antibodies of the present invention to antigens on mycobacterial bacilli. It is also possible that antibody binding may block macrophage infection by steric hindrance or disruption of its oligomeric structure. Thus, antibodies acting on mycobacterial bacilli released from killed, infected macrophages may interfere with the spread of re-infection to fresh macrophages. This hypothesis involves a synergistic action between antibodies and cytotoxic T cells, acting early after infection, eg. γδ and NK T cells, but could later involve also CD8 and CD4 cytotoxic T cells.

According to a fifth aspect of the invention, there is provided an attenuated *mycobacterium* in which a gene has been modified thereby rendering the *mycobacterium* substantially reduced in ability to enter a latent state, wherein said gene is a gene the expression of which is down-regulated during a stationary phase culture of *mycobacteria* under nutrient-starving culture conditions when compared with an exponential phase culture of *mycobacteria* under culture conditions that are not nutrient-starving. The modification preferably inactivates the gene in question, and preferably renders the *mycobacterium* substantially non-pathogenic.

The term "modified" refers to any genetic manipulation such as a nucleic acid or nucleic acid sequence replacement, a deletion, or an insertion which renders the *mycobacterium* substantially reduced in ability to enter a latent state. In one embodiment the entire down-regulatable gene may be deleted.

In a preferred embodiment, gene to be modified has a wild-type coding sequence selected from the group consisting of SEQ ID NO: 2, 4, 6, 8, 10, 12, 14, 16, 18, 20, 22, 24, 26, 28, 30, 32, 34, 36, 38, 40, 42, 44, 46.

It will be appreciated that the above wild-type sequences may include minor variations depending on the Database employed. The term "wild-type" indicates that the sequence in question exists as a coding sequence in nature.

According to a sixth aspect of the invention, there is provided an attenuated microbial carrier, comprising a peptide encoded by a gene, or a fragment or variant or derivative of said peptide, the expression of which gene is down-regulated during a stationary phase culture of *mycobacteria* under nutrient-starving culture conditions when compared with an exponential phase culture of *mycobacteria* under culture conditions that are not nutrient-starving.

In use, the peptide (or fragment, variant or derivative) is either at least partially exposed at the surface of the carrier, or the carrier becomes degraded in vivo so that at least part of the peptide (or fragment, variant or derivative) is otherwise exposed to a host's immune system.

In a preferred embodiment, the attenuated microbial carrier is attenuated *salmonella*, attenuated vaccinia virus, attenuated fowlpox virus, or attenuated *M. bovis* (eg. BCG strain).

In a preferred embodiment, the peptide is selected from the group consisting of SEQ ID NO: 1, 3, 5, 7, 9, 11, 13, 15, 17, 19, 21, 23, 25, 27, 29, 31, 33, 35, 37, 39, 41, 43, 45.

According to a seventh aspect of the invention, there is provided a DNA plasmid comprising a promoter, a polyadenylation signal, and a DNA sequence that encodes a gene or a fragment or variant of derivative of said gene, the expression of which gene is down-regulated during a stationary phase culture of *mycobacteria* under nutrient-starving culture conditions when compared with an exponential phase culture of *mycobacteria* under culture conditions that are not nutrient-starving, wherein the promoter and polyadenylation signal are operably linked to the DNA sequence. Reference to gene preferably means the peptide-coding sequence of the down-regulated gene.

The term DNA "fragment" used in this invention will usually comprise at least about 5 codons (15 nucleotides), more usually at least about 7 to 15 codons, and most preferably at least about 35 codons. This number of nucleotides is usually about the minimal length required for a successful probe that would hybridize specifically with such a sequence.

In preferred embodiments, the DNA "fragment" has a nucleotide length which is at least 50%, preferably at least 70%, and more preferably at least 80% that of the coding sequence of the corresponding down-regulated gene.

The term DNA "variant" means a DNA sequence which has substantial homology or substantial similarity to the coding sequence (or a fragment thereof) of a down-regulated gene. A nucleic acid or fragment thereof is substantially homologous (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 to 98% of the nucleotide bases. Homology determination is performed as described supra for peptides.

Alternatively, a DNA "variant" is substantially homologous (or substantially similar) with the coding sequence (or a fragment thereof of a down-regulated gene when they are capable of hybridizing under selective hybridization conditions. Selectivity of hybridization exists when hybridization occurs which is substantially more selective than total lack of specificity. Typically, selective hybridization will occur when there is at least about 65% homology over a stretch of at least about 14 nucleotides, preferably at least about 70%, more preferably at least about 75%, and most preferably at least about 90%. See, Kanehisa (1984) Nuc. Acids Res. 12:203-213. The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration (eg. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. However, the combination of parameters is much more important than the measure of any single parameter. See, for example, Wetmur and Davidson (1968) J. Mol. Biol. 31:349-370.

The term DNA "derivative" means a DNA polynucleotide which comprises a DNA sequence (or a fragment, or variant thereof) corresponding to the coding sequence of the down-regulated gene and an additional DNA sequence which is not naturally associated with the DNA sequence corresponding to the coding sequence. The comments on peptide derivative supra also apply to DNA "derivative". A "derivative" may, for example, include two or more coding sequences of a mycobacterial operon that is induced during nutrient starvation. Thus, depending on the presence of absence of a non-coding region between the coding sequences, the expression product/s of such as "derivative" may be a fusion protein, or separate peptide products encoded by the individual coding regions.

The above terms DNA "fragment", "variant", and "derivative" have in common with each other that the resulting peptide products have cross-reactive antigenic properties which are substantially the same as those of the corresponding wild-type peptide. Preferably all of the peptide products of the above DNA molecule embodiments of the present invention bind to an antibody which also binds to the wild-type peptide. Alternatively, all of the above peptide products are capable of inducing a "recall response" of a T lymphocyte which has been previously exposed to an antigenic component of a mycobacterial infection.

The promoter and polyadenylation signal are preferably selected so as to ensure that the gene is expressed in a eukaryotic cell. Strong promoters and polyadenylation signals are preferred.

In a related aspect, the present invention provides an isolated RNA molecule that is encoded by a DNA sequence of the present invention, or a fragment or variant or derivative of said DNA sequence.

An "isolated" RNA is an RNA which is substantially separated from other mycobacterial components that naturally accompany the sequences of interest, eg., ribosomes, polymerases, and other mycobacterial polynucleotides such as DNA and other chromosomal sequences.

The above RNA molecule may be introduced directly into a host cell as, for example, a component of a vaccine.

Alternatively the RNA molecule may be incorporated into an RNA vector prior to administration.

The polynucleotide sequences (DNA and RNA) of the present invention include a nucleic acid sequence that has been removed from its naturally occurring environment, and recombinant or cloned DNA isolates and chemically synthesized analogues or analogues biologically synthesized by heterologous systems.

The term "recombinant" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; and (3) does not occur in nature. This artificial combination is often accomplished by either chemical synthesis means, or by the artificial manipulation of isolated segments of nucleic acids, eg., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

In embodiments of the invention the polynucleotides may encode a peptide (or fragment, variant, or derivative) that is down-regulated under nutrient-starving conditions. A nucleic acid is said to "encode" a peptide if, in its native state or when manipulated, it can be transcribed and/or translated to produce the peptide (or fragment, variant or derivative thereof. The anti-sense strand of such a nucleic acid is also said to encode the peptide (or fragment, variant, or derivative).

Also contemplated within the invention are expression vectors comprising the polynucleotide of interest. Expression vectors generally are replicable polynucleotide constructs that encode a peptide operably linked to suitable transcriptional and translational regulatory elements. Examples of regulatory elements usually included in expression vectors are promoters, enhancers, ribosomal binding sites, and transcription and translation initiation and termination sequences. These regulatory elements are operably linked to the sequence to be translated. A nucleic acid sequence is operably linked when it is placed into a functional relationship with another nucleic acid sequence. For instance, a promoter is operably linked to a coding sequence if the promoter affects its transcription or expression. Generally, operably linked means that the DNA sequences being linked are contiguous and, where necessary to join two protein coding regions, contiguous and in reading frame. The regulatory elements employed in the expression vectors containing a polynucleotide encoding a virulence factor are functional in the host cell used for expression.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The polynucleotides of the present invention may also be produced by chemical synthesis, eg. by the phosphoramidite method or the triester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system recognized by the host, including the intended DNA fragment encoding the desired peptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals from polypeptides secreted from the host cell of choice may also be included where appropriate, thus allowing the protein to cross and/or lodge in cell membranes, and thus attain its functional topology or be secreted from the cell.

Appropriate promoter and other necessary vector sequences are selected so as to be functional in the host, and may, when appropriate, include those naturally associated with mycobacterial genes. Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others.

Appropriate non-native mammalian promoters may include the early and late promoters from SV40 or promoters derived from murine moloney leukemia virus, mouse mammary tumour virus, avian sarcoma viruses, adenovirus II, bovine papilloma virus or polyoma. In addition, the construct may be joined to an amplifiable gene (eg. DHFR) so that multiple copies of the gene may be made.

While such expression vectors may replicate autonomously, they may less preferably replicate by being inserted into the genome of the host cell.

Expression and cloning vectors may contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, eg. ampicillin, neomycin, methotrexate, etc.; (b) complement auxotrophic deficiencies; or (c) supply critical nutrients not available from complex media, e.g. the gene encoding D-alanine racemase for Bacilli. The choice of appropriate selectable marker will depend on the host cell.

The vectors containing the nucleic acids of interest can be transcribed in vitro and the resulting RNA introduced into the host cell (eg. by injection), or the vectors can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). The cells into which have been introduced nucleic acids described above are meant to also include the progeny of such cells.

Large quantities of the nucleic acids and peptides of the present invention may be prepared by expressing the nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used.

Mammalian or other eukaryotic host cells, such as those of yeast, filamentous fungi, plant, insect, amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although other cell lines may be appropriate, e.g., to provide higher expression, desirable glycosylation patterns.

Clones are selected by using markers depending on the mode of the vector construction. The marker may be on the same or a different DNA molecule, preferably the same DNA molecule. The transformant may be screened or, preferably, selected by any of the means well known in the art, e.g., by resistance to such antibiotics as ampicillin, tetracycline.

The polynucleotides of the invention may be inserted into the host cell by any means known in the art, including for example, transformation, transduction, and electroporation. As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. "Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

In one embodiment, a DNA plasmid or RNA vector may encode a component of the immune system that is specific to an immune response following challenge with a peptide, wherein said peptide is encoded by a mycobacterial gene that is down-regulated under nutrient-starving culture conditions.

An example of such a component is an antibody to the peptide product of the down-regulated gene. Thus, in one embodiment, the nucleic acid sequence (eg. DNA plasmid or RNA vector) encodes the antibody in question.

In the context of the present invention, the term plasmid is equivalent to vector. Thus, a plasmid may be either linear or circularised nucleic acid.

An eighth aspect provides use of said aforementioned peptide or fragment or variant or derivative thereof, inhibitor, antibody, attenuated *mycobacterium*, attenuated microbial carrier, DNA sequence corresponding to the coding sequence of a mycobacterial gene that is down-regulated under nutrient-starving conditions or a fragment or variant or derivative of said DNA sequence, DNA plasmid comprising said DNA sequence or said fragment or variant or derivative, RNA sequence encoded by said DNA sequence or said fragment or variant or derivative, and/or RNA vector comprising said RNA sequence, in the manufacture of a medicament for treating or preventing a mycobacterial infection.

The term "preventing" includes reducing the severity/intensity of, or initiation of, a mycobacterial infection.

The term "treating" includes post-infection therapy and amelioration of a mycobacterial infection.

In a related aspect, there is provided a method of treating or preventing a mycobacterial infection, comprising administration to a subject of a medicament selected from the group consisting of said aforementioned peptide or fragment or variant or derivative thereof, inhibitor, antibody, attenuated *mycobacterium*, attenuated microbial carrier, DNA sequence corresponding to the coding sequence of a mycobacterial gene that is down-regulated under nutrient-starving conditions or a fragment or variant or derivative of said DNA sequence, DNA plasmid comprising said DNA sequence or said fragment or variant or derivative, RNA sequence encoded by said DNA sequence or said fragment or variant or derivative, and/or RNA vector comprising said RNA sequence.

The immunogenicity of the epitopes of the peptides of the invention may be enhanced by preparing them in mammalian or yeast systems fused with or assembled with particle-forming proteins such as, for example, that associated with hepatitis B surface antigen. Vaccines may be prepared from one or more immunogenic peptides of the present invention.

Typically, such vaccines are prepared as injectables, either as liquid solutions or suspensions; solid forms suitable for solution in, or suspension in, liquid prior to injection may also be prepared. The preparation may also be emulsified, or the peptide encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmito yl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The vaccines are conventionally administered parenterally, by injection, for example, either subcutaneously or intramuscularly. Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

The peptides may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or re-enforce the immune response, for example, at 14 months for a second dose, and if needed, a subsequent dose(s) after several months. The dosage regimen will also, at least in part, be determined by the need of the individual and be dependent upon the judgment of the practitioner.

In addition, the vaccine containing the immunogenic mycobacterial antigen(s) may be administered in conjunction with other immunoregulatory agents, for example, immunoglobulins, as well as antibiotics.

The medicament may be administered by conventional routes, eg. intravenous, intraperitoneal, intranasal routes.

The outcome of administering antibody-containing compositions may depend on the efficiency of transmission of antibodies to the site of infection. In the case of a mycobacterial respiratory infection (eg. a *M. tuberculosis* infection), this may be facilitated by efficient transmission of antibodies to the lungs.

In one embodiment the medicament may be administered intranasally (i.n.). This mode of delivery corresponds to the route of delivery of a *M. tuberculosis* infection and, in the case of antibody delivery, ensures that antibodies are present at the site of infection to combat the bacterium before it becomes intracellular and also during the period when it spreads between cells.

An intranasal composition may be administered in droplet form having approximate diameters in the range of 100-5000 µm, preferably 500-4000 µm, more preferably 1000-3000 µm. Alternatively, in terms of volume, the droplets would be in the approximate range of 0.001-100 µl, preferably 0.1-50 µl, more preferably 1.0-25 µl.

Intranasal administration may be achieved by way of applying nasal droplets or via a nasal spray.

In the case of nasal droplets, the droplets may typically have a diameter of approximately 1000-3000 µm and/or a volume of 1-25 µl.

In the case of a nasal spray, the droplets may typically have a diameter of approximately 100-1000 µm and/or a volume of 0.001-1 µl.

It is possible that, following i.n. delivery of antibodies, their passage to the lungs is facilitated by a reverse flow of mucosal secretions, although mucociliary action in the respiratory tract is thought to take particles within the mucus out of the lungs. The relatively long persistence in the lungs' lavage, fast clearance from the bile and lack of transport to the saliva of some antibodies suggest the role of mucosal site specific mechanisms.

In a different embodiment, the medicament may be delivered in an aerosol formulation. The aerosol formulation may take the form of a powder, suspension or solution.

The size of aerosol particles is one factor relevant to the delivery capability of an aerosol. Thus, smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli.

The aerosol particles may be delivered by way of a nebulizer or nasal spray.

In the case of aerosol delivery of the medicament, the particles may have diameters in the approximate range of 0.1-50 µm, preferably 1-25 µm, more preferably 1-5 µm.

The aerosol formulation of the medicament of the present invention may optionally contain a propellant and/or surfactant.

By controlling the size of the droplets which are to be administered to a patient to within the defined range of the present invention, it is possible to avoid/minimise inadvertent antigen delivery to the alveoli and thus avoid alveoli-associated pathological problems such as inflammation and fibrotic scarring of the lungs.

I.n. vaccination engages both T and B cell mediated effector mechanisms in nasal and bronchus associated mucosal tissues, which differ from other mucosae-associated lymphoid tissues.

The protective mechanisms invoked by the intranasal route of administration may include: the activation of T lymphocytes with preferential lung homing; upregulation of co-stimulatory molecules, eg. B7.2; and/or activation of macrophages or secretory IgA antibodies.

Intranasal delivery of antigens may facilitate a mucosal antibody response is invoked which is favoured by a shift in the T cell response toward the Th2 phenotype which helps antibody production. A mucosal response is characterised by enhanced IgA production, and a Th2 response is characterised by enhanced IL-4 production.

Intranasal delivery of mycobacterial antigens allows targeting of the antigens to submucosal B cells of the respiratory system. These B cells are the major local IgA-producing cells in mammals and intranasal delivery facilitates a rapid increase in IgA production by these cells against the mycobacterial antigens.

In one embodiment administration of the medicament comprising a mycobacterial antigen stimulates IgA antibody production, and the IgA antibody binds to the mycobacterial antigen. In another embodiment, a mucosal and/or Th2 immune response is stimulated.

In another embodiment monoclonal antibodies, in particular, may be used to raise anti-idiotype antibodies. Anti-idiotype antibodies are immunoglobulins which carry an "internal image" of the antigen of the infectious agent against which protection is desired. These anti-idiotype antibodies may also be useful for treatment, vaccination and/or diagnosis of mycobacterial infections.

According to another aspect of the present invention, the peptides (including fragments, variants, and derivatives thereof) of the present invention and antibodies that bind thereto are useful in immunoassays to detect the presence of antibodies to mycobacteria, or the presence of the virulence associated antigens in biological samples. Design of the immunoassays maybe subject to a great deal of variation, and many formats are known in the art. The immunoassay may utilize at least one epitope derived from a peptide of the present invention. In one embodiment, the immunoassay uses a combination of such epitopes. These epitopes may be derived from the same or from different bacterial peptides, and may be in separate recombinant or natural peptide or together in the same recombinant peptide.

An immunoassay may use, for example, a monoclonal antibody directed towards a virulence associated peptide epitope(s), a combination of monoclonal antibodies directed towards epitopes of one mycobacterial antigen, monoclonal antibodies directed towards epitopes of different mycobacterial antigens, polyclonal antibodies directed towards the same antigen, or polyclonal antibodies directed towards different antigens. Protocols may be based, for example, upon competition, or direct reaction, or sandwich type assays. Protocols may also, for example, use solid supports, or may be by immunoprecipitation. Most assays involve the use of labelled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labelled and mediated immunoassays, such as ELISA assays.

Typically, an immunoassay for an antibody(s) to a peptide, will involve selecting and preparing the test sample suspected of containing the antibodies, such as a biological sample, then incubating it with an antigenic (ie. epitope-containing) peptide(s) under conditions that allow antigen-antibody complexes to form, and then detecting the formation of such complexes. The immunoassay may be of a standard or competitive type.

The peptide is typically bound to a solid support to facilitate separation of the sample from the peptide after incubation. Examples of solid supports that can be used are nitrocellulose (eg. in membrane or microtiter well form), polyvinyl chloride (eg. in sheets or microtiter wells), polystyrene latex (eg. in beads or microtiter plates, polyvinylidine fluoride (known as Immulon), diazotized paper, nylon membranes, activated beads, and Protein A beads. For example, Dynatech Immulon microtiter plates or 60 mm diameter polystyrene beads (Precision Plastic Ball) may be used. The solid support containing the antigenic peptide is typically washed after separating it from the test sample, and prior to detection of bound antibodies.

Complexes formed comprising antibody (or, in the case of competitive assays, the amount of competing antibody) are detected by any of a number of known techniques, depending on the format. For example, unlabelled antibodies in the complex may be detected using a conjugate of antixenogeneic Ig complexed with a label (eg. an enzyme label).

In immunoassays where the peptides are the analyte, the test sample, typically a biological sample, is incubated with antibodies directed against the peptide under conditions that allow the formation of antigen-antibody complexes. It may be desirable to treat the biological sample to release putative bacterial components prior to testing. Various formats can be employed. For example, a "sandwich assay" may be employed, where antibody bound to a solid support is incubated with the test sample; washed; incubated with a second, labelled antibody to the analyte, and the support is washed again. Analyte is detected by determining if the second antibody is bound to the support. In a competitive format, a test sample is usually incubated with antibody and a labelled, competing antigen is also incubated, either sequentially or simultaneously.

Also included as an embodiment of the invention is an immunoassay kit comprised of one or more peptides of the invention, or one or more antibodies to said peptides, and a buffer, packaged in suitable containers.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumours, organs, and also samples of in vitro cell culture constituents (including but not limited to conditioned medium resulting from the growth of cells in cell culture medium, putatively virally infected cells, recombinant cells, and cell components).

In a related diagnostic assay, the present invention provides nucleic acid probes for detecting a mycobacterial infection.

Using the polynucleotides of the present invention as a basis, oligomers of approximately 8 nucleotides or more can be prepared, either by excision from recombinant polynucleotides or synthetically, which hybridize with the mycobacterial sequences, and are useful in identification of *mycobacteria*. The probes are a length which allows the detection of the down-regulated sequences by hybridization. While 6-8 nucleotides may be a workable length, sequences of 10-12 nucleotides are preferred, and at least about 20 nucleotides appears optimal. These probes can be prepared using routine methods, including automated oligonucleotide synthetic methods. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic-acids contained therein. The resulting nucleic acid from the sample may be subjected to gel electrophoresis or other size separation techniques; alternatively, the nucleic acid sample may be dot blotted without size separation. The probes are usually labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes may be made completely complementary to the virulence encoding polynucleotide. Therefore, usually high stringency conditions are desirable in order to prevent false positives. The stringency of hybridization is determined by a number of factors during hybridization and during the washing procedure, including temperature, ionic strength, length of time, and concentration of formamide.

It may be desirable to use amplification techniques in hybridization assays. Such techniques are known in the art and include, for example, the polymerase chain reaction (PCR) technique.

The probes may be packaged into diagnostic kits. Diagnostic kits include the probe DNA, which may be labeled; alternatively, the probe DNA may be unlabeled and the ingredients for labeling may be included in the kit in separate containers. The kit may also contain other suitably packaged reagents and materials needed for the particular hybridization protocol, for example, standards, as well as instructions for conducting the test.

In a preferred embodiment, a peptide (or fragment or variant or derivative) of the present invention is used in a diagnostic assay to detect the presence of a T-lymphocyte, which T-lymphocyte has been previously exposed to an antigenic component of a mycobacterial infection in a patient.

In more detail, a T-lymphocyte which has been previously exposed to a particular antigen will be activated on subsequent challenge by the same antigen. This activation provides a means for identifying a positive diagnosis of mycobacterial infection. In contrast, the same activation is not achieved by a T-lymphocyte which has not been previously exposed to the particular antigen.

The above "activation" of a T-lymphocyte is sometimes referred to as a "recall response" and may be measured, for example, by determining the release of interferon (eg. IFN-Y) from the activated T-lymphocyte. Thus, the presence of a mycobacterial infection in a patient may be determined by the release of a minimum concentration of interferon from a T-lymphocyte after a defined time period following in vitro challenge of the T-lymphocyte with a peptide (or fragment or variant or derivative) of the present invention.

In use, a biological sample containing T-lymphocytes is taken from a patient, and then challenged with a peptide (or fragment, variant, or derivative thereof) of the present invention.

The above T-lymphocyte diagnostic assay may include an antigen presenting cell (APC) expressing at least one major histocompatibility complex (MHC) class II molecule expressed by the patient in question. The APC may be inherently provided in the biological sample, or may be added exogenously. In one embodiment, the T-lymphocyte is a CD4 T-lymphocyte.

Brief mention is now made to the Figures of the present application, in which:

FIG. 1 illustrates the viable counts for *M. tuberculosis* during culture under batch fermentation conditions at a DOT of 50% air saturation (37° C.);

FIG. 2 illustrates the concentration of glycerol (as the primary carbon and energy source) during culture of *M. tuberculosis* under batch fermentation conditions at the separate DOT concentrations of 0.5% flow oxygen culture) and 50% (aerobic culture) air saturation (37° C.).

FIG. 3 illustrates the DOT within the medium of the mycobacterial culture described in Example 18; and FIG. 4 illustrates the viable counts for *M. tuberculosis* during the batch fermentation conditions of Example 18 (ie. carbon-starvation, and oxygen limiting conditions).

Two alternative mycobacterial culture methods have been employed to study genes which are down-regulated during mycobacterial latency. The first method is described in Examples 1-8, whereas the second method is described in Example 18.

EXAMPLE 1

In Vitro Model of Mycobacterial Persistence Under Aerobic, Nutrient-Starved Conditions Materials and Methods Strain Studies were performed with *M. tuberculosis* strain H37Rv (NCTC cat. no. 7416)—a representative strain of *M. tuberculosis*. Stock cultures were grown on Middlebrook 7H10+OADC for 3 weeks at 37±2° C.

Culture Medium

Persistence cultures were established in Middlebrook 7H9 medium supplemented with Middlebrook ADC enrichment, 0.2% Tween 80 and 0.2% glycerol (Table 1). The medium was prepared with high quality water from a Millipore water purification system and filter sterilised by passage through a 0.1 μm pore size cellulose acetate membrane filter capsule (Sartorius Ltd). The pH was adjusted to 6.6 with concentrated hydrochloric acid.

Middlebrook 7H10+OADC agar was used to prepare inoculum cultures, enumerate the number of culturable bacteria in samples, and to assess culture purity.

Culture System

We previously developed a process for the culture of *mycobacteria* under controlled and defined conditions—Patent Application No. PCT/GB00/00760 (WO00/52139). We used this culture system operated as a batch fermenter for the following studies of mycobacterial persistence.

Culture experiments were performed in a one liter glass vessel operated at a working volume of 750 ml. The culture was agitated by a magnetic bar placed in the culture vessel coupled to a magnetic stirrer positioned beneath the vessel. Culture conditions were continuously monitored by an Anglicon Microlab Fermentation System (Brighton Systems, Newhaven), linked to sensor probes inserted into the culture through sealed ports in the top plate. The oxygen concentration was monitored with a galvanic oxygen electrode (Uniprobe, Cardiff) and was controlled through sparging the culture with a mixture of air and oxygen free-nitrogen. Temperature was monitored by an Anglicon temperature probe, and maintained by a heating pad positioned beneath the culture vessel. Culture pH was measured using an Ingold pH electrode (Mettler-Toledo, Leicester).

Inoculation and Culture

The vessel was filled with 750 ml of sterile culture medium and parameters were allowed to stabilise at 37° C.∓2° C., pH 6.9∓0.3 and a dissolved oxygen tension of approximately 70% air saturation. A dense inoculum suspension was prepared by resuspending Middlebrook agar cultures; grown at 37° C.∓2° C. for 3 weeks, in sterile deionised water. The inoculum was aseptically transferred to the culture vessel, to provide an initial culture turbidity of approximately 0.25 at 540 nm.

The culture were maintained at 37° C. with an agitation rate of 500 to 750 rpm. The dissolved oxygen tension was maintained between 50-70% air saturation with the aid of culture sparging. The initial culture pH was set at approximately 6.7 and was monitored throughout the experiment. The culture was maintained for 50 days and samples were removed regularly to monitor growth and survival, nutrient utilisation and gene expression.

Growth and Survival

Bacterial growth and survival was assessed by determining the number of viable cells in the culture system at specific time points. This was achieved by preparing a decimal dilution series of the sample in sterile water and plating 100 μl aliquots onto Middlebrook 7H10+OADC plates. The plates were incubated at 37° C. for up to 4 weeks before enumerating the number of colonies formed.

Nutrient Utilisation

Glycerol is the primary carbon and energy source present in Middlebrook 7H9 medium with ADC, 0.2% Tween and 0.2% Glycerol. The rate at which glycerol was utilised was determined using the Glycerol Determination Kit Cat. No. 148 270 Boehringer Mannheim.

Microarray Experiments

RNA was extracted from culture samples collected at different time points during the experiment. A fluorescently-labelled cDNA was then transcribed from each sample of RNA. The cDNA was labelled by the incorporation of either Cy3 or Cy5 labelled dCTP (Dyes are supplied by Amersham Pharmacia Biotech).

Whole *M. tuberculosis* genome arrays were prepared from *M. tuberculosis* genomic DNA using ORF-specific primers. PCR products corresponding to each ORF were spotted in a grid onto a standard glass microscope slide using a BioRobotics microgrid robot (MWG Biotech) at a resolution of >4000 spots/cm$^2$.

In each microarray experiment a whole genome array was hybridised with labelled cDNA from one culture sample (Test sample). Each array was also hybridised with control DNA incorporating a different Cy dye and prepared from DNA extracted from *M. tuberculosis* strain H37Rv (control sample).

Each array was scanned at two different wavelengths corresponding to the excitation maxima of each dye and the intensity of the emitted light was recorded. The ration of the intensity values for the test and control samples was determined for each array. The slides were scanned using an Affymetrix 428 scanner. The raw data was initially analysed by ImaGene software. The scanned images were then transferred to another software package known as GeneSpring to analyse the expression of each gene.

Results

After inoculation the culture entered exponential growth and continued to grow exponentially until 10 days after inoculation (see FIG. 1). Cessation of exponential growth coincided with depletion of the primary carbon and energy source—glycerol (see FIG. 2). As the culture entered stationary phase, viability started to decline and continued to decline steadily over the duration of the study. After 40 days in stationary phase, approximately 1% of the culture was still culturable on Middlebrook agar.

The gene expression profiles for samples collect at day 5 and day 50 were compared. Three arrays were prepared for each sample and the test data were normalised against the control data on each chip. The normalised data for each set of arrays were then averaged and the two sets of data were compared. Those genes that were expressed at least 1.5-fold less at day 50 relative to day 5 were selected. SEQ IDs 1-20 identified by this method are listed in Table 2, together with assigned biological functions for each of the encoded peptide.

The coding sequences (nucleic acid sequences are given from the transcription start site to the stop codon) for these genes and their corresponding amino acid sequences are listed in the accompanying sequence listing, in which the first SEQ ID NO is the amino acid sequence and the second SEQ ID NO is the corresponding nucleic acid coding sequence.

TABLE 1 liquid medium formulation for persistence cultures - Middlebrook 7H9 medium supplemented with ADC, 0.2% Tween 80 and 0.2% Glycerol

| Composition per liter | |
|---|---|
| $Na_2HPO_4$ | 2.5 g |
| $KH_2PO_4$ | 1.0 g |
| Monosodium glutamate | 0.5 g |
| $(NH_4)_2SO_4$ | 0.5 g |
| Sodium citrate | 0.1 g |
| $MgSO_4.7H_2O$ | 0.05 g |
| Ferric ammonium citrate | 0.04 g |
| $CuSO_4.5H_2O$ | 1.0 mg |
| Pyridoxine | 1.0 mg |
| $ZnSO_4.7H_2O$ | 1.0 mg |
| Biotin | 0.5 mg |
| $CaCl_2.2H_2O$ | 0.5 mg |
| Middlebrook ADC enrichment | 100 ml |
| Glycerol | 2.0 ml |
| Tween 80 | 2.0 ml |
| Middlebrook ADC enrichment - per | 100 ml |
| Bovine serum albumin | 5.0 g |
| Glucose | 2.0 g |
| Catalase | 3.0 mg |

GTC lysis solution containing: 5 M guanidine thiocyanate, 0.5% N-lauryl sarcosine, 25 mM tri-sodium citrate, 0.1 M 2-mercaptoethanol, and 0.5% Tween 80.

Chloroform

Isopropanol 3M sodium acetate

70% Ethanol microfuge ribolyser

Sterile plasticware-Falcon tubes, screw capped eppendorfs, gilson tips—all RNase free Glassware—baked at 160° C. for at least 16 hours Method Steps performed at Containment level 3; within a Class III microbiological safety cabinet.

Remove 10 or 20 ml of culture ($10^9$/ml) and immediately add this to 4 volumes of GTC lysis buffer in a plastic specimen pot. Seal the pot tightly.

Incubate the cells in GTC lysis buffer for 1 hour at room temperature. Surface decontaminate the plastic pot with 5% Hycolin for 5 minutes. Transfer the sample to the pass box and place it into a plastic carry tin with a sealable lid. Close the container securely and transport it to a non-toxic cabinet CL3 cabinet.

Equally distribute the lysis mixture between Falcon tubes. Place these tubes into centrifuge buckets and seal the buckets tightly. Surface-decontaminate the buckets for 5 minutes with 5% Hycolin. Then transfer them to the centrifuge (Baird and Tatlock Mark IV refrigerated bench-top centrifuge). Spin the tubes at 3,000 rpm for 30 minutes.

TABLE 2

Genes down-regulated during survival under carbon starvation conditions.

| Gene | Fold-down | Assigned function | SEQ ID NO: |
|---|---|---|---|
| Rv0062; celA (1F8) | 6.9605 | Cellulase CELA1 (endoglucanase) (endo-1,4-beta-glucanase) (Fl-CMASE) (carboxymethyl cellulase) | 1;2 |
| Rv0545c; pitA (4N16) | 5.0523 | Low-affinity inorganic phosphate transporter integral membrane protein PITA | 3;4 |
| Rv0653c; (4P23) | 6.2012 | Transcriptional regulatory protein | 5;6 |
| Rv0701; rplC (3N15) | 5.4226 | 50S ribosomal protein L3 RPLC | 7;8 |
| Rv1630; rpsA (5E24) | 5.815 | Ribosomal protein S1 RpsA | 9;10 |
| Rv1887; (7D11) | 5.8208 | | 11;12 |
| Rv2144c; (9G15) | 6.0519 | Transmembrane protein | 13;14 |
| Rv3284; (4G3) | 5.4896 | | 15;16 |
| Rv3458c; rpsD (4D18) | 5.432 | 30S ribosomal protein S4 RPSD | 17;18 |
| Rv3478; PPE (4H19) | 8.7897 | PE family protein | 19;20 |

EXAMPLE 2

RNA Extraction from *M. tuberculosis* for Microarray Analysis

Materials and Methods

Trizol (Life Technologies)—formulation of phenol and guanidine thiocyanate.

Return the unopened buckets to the cabinet. Remove the centrifuge tubes and pour the supernatant into a waste bottle for GTC lysis buffer.

Resuspend each pellet in 1 ml of Trizol (formulation of phenol and GTC cat no. 15596-026). The manufacturers guidelines recommend lysing cells by repetitive pipetting. Although this action alone will not lyse *M. tuberculosis*, it is important to completely resuspend the pellet in Trizol.

Transfer 1 ml of cells into a FastRNA tube and ribolyse it at power setting 6.5 for 45 seconds.

Leave the tube to incubate at room temperature for 5 minutes.

Remove the aqueous layer from the tube and add this to 200 μl of chloroform in a screw-capped eppendorf tube. Shake each tube vigorously for about 15 seconds. Incubate for 2-3 minutes at room temperature.

Spin the tube at 13,000 rpm for 15 minutes. Following centrifugation, the liquid separates into red phenol/chloroform phase, an interface, and a clear aqueous phase.

Carefully remove the aqueous phase and transfer it to a fresh eppendorf tube containing 500 μl of chloroform/isoamyl alcohol (24:1). Spin the tubes at 13,000 rpm for 15 minutes.

Transfer the aqueous phase to an eppendorf tube containing 50 μl of sodium acetate and 500 μl of isopropanol.

Surface decontaminate the eppendorf tube with 5% Hycolin for 5 minutes. Remove the tube from the CL3 laboratory and continue with the procedure in laboratory 157.

Steps performed at Containment level 2:

Precipitate the RNA at −70° C. for at least 30 minutes—can do this step overnight.

Spin the precipitated RNA down at 13,000 rpm for 10 minutes. Remove the supernatant and wash the pellet in 70% ethanol. Repeat centrifugation.

Remove the 70% ethanol and air-dry the pellet. Dissolve the pellet in RNAse free water.

Freeze the RNA at −70° C. to store it.

EXAMPLE 3

Isolation of Genomic DNA From *Mycobacterium tuberculosis* Grown in Chemostat Culture. DNA Then Used to Generate Cy3 or Cy5 Labelled DNA for Use as a Control in Microarray Experiments Materials and Methods
  Beads 0.5 mm in diameter
  Bead beater
  Bench top centrifuge
  Platform rocker
  Heat block
  Falcon 50 ml centrifuge tubes
  Sorvall RC-5C centrifuge
  250 ml polypropylene centrifuge pots.
  Screw capped eppendorf tubes
  Pipettes 1 ml, 200 μl, 10 ml, 5 ml
  Breaking buffer
  50 mM Tris HCl pH 8.0
  10 mM EDTA
  100 mM NaCl Procedure Mechanical Disruption of *M. tuberculosis* Cells 150 ml of chemostat cells (O.D of 2.5 at 540 nm) are spun down at 15,000 rpm for minutes in 250 ml polypropylene pots using centrifuge Sorvall RC-5C.

The supernatant is discarded.

Cells are re-suspended in 5 ml of breaking buffer in a 50 ml Falcon tube and centrifuged at 15,000 rpm for a further 15 minutes.

The supernatant is removed and additional breaking buffer is added at a volume of 5 ml. Beads are used to disrupt the cells. These are used at a quantity of 1 ml of beads for 1 ml of cells. Place the sample into the appropriate sized chamber. Place in the bead beater and secure the outer unit (containing ice) and process at the desired speed for 30 seconds.

Allow the beads to settle for 10 minutes and transfer cell lysate to a 50 ml Falcon centrifuge tube Wash beads with 2-5 ml of breaking buffer by pipetting washing buffer up and down over the beads.

Add this washing solution to the lysate in the falcon tube

Removal of Proteins and Cellular Components

Add 0.1 volumes of 10% SDS and 0.01 volumes proteinase K.

Mix by inversion and heat at 55° C. in a heat block for 2-3 hours

The resulting mix should be homogenous and viscous. Additional SDS may be added to assist here to bring the concentration up to 0.2%

Add an equal volume of phenol/chloroform/Isoamyl alcohol in the ratio: 25/24/1.

Gently mix on a platform rocker until homogenous

Spin down at 3,000 rpm for 20 minutes

Remove the aqueous phase and place in a fresh tube

Extract the aqueous phase with an equal volume of chloroform to remove traces of cell debris and phenol. Chloroform extractions may need to be repeated to remove all the debris.

Precipitate the DNA with 0.3 M sodium acetate and an equal volume of isopropanol.

Spool as much DNA as you can with a glass rod

Wash the spooled DNA in 70% ethanol followed by 100% ethanol

Leave to air dry

Dissolve the DNA in sterile deionised water (500 μl)

Allow DNA to dissolve at 4° C. for approximately 16 hours.

Add RNase 1 (500 U) to the dissolved DNA

Incubate for 1 hour at 37° C.

Re-extract with an equal volume of phenol/chloroform followed by a chloroform extraction and precipitate as before Spin down the DNA at 13,000 rpm Remove the supernatant and wash the pellet in 70% ethanol Air dry Dissolve in 200-500 μl of sterile water.

EXAMPLE 4

Preparation of Cy3 or Cy5 Labelled DNA from DNA a) Prepare One Cy3 or one Cy5 Labelled DNA Sample per Microarray Slide
  Each sample:

| DNA | 2-5 μg |
|---|---|
| Random primers (3 μg/μl) | 1 μl |
| H$_2$O | to 41.5 μl |

Heat at 95° C. for 5 min, snap cool on ice and briefly centrifuge.

Add to each:

| 10 × REact 2 buffer | 5 μl |
|---|---|
| dNTPs (5 mM dA/GTTP, 2 mM dCTP) | 1 μl |
| Cy3 OR Cy5 dCTP | 1.5 μl |
| Klenow (5 U/μl) | 1 μl | b) Prehybridise Slide

Mix the prehybridisation solution in a Coplin jar and incubate at 65° C. during the labelling reaction to equilibriate.

| | |
|---|---|
| Prehybridisation: 20 × SSC | 8.75 ml (3.5 × SSC) |
| 20% SDS | 250 µl (0.1% SDS) |
| BSA (100 mg/ml) | 5 ml (10 mg/ml) |
| H$_2$O | to 50 ml |

Incubate the microarray slide in the pre-heated prehybridisation solution at 65° C. for 20 min. Rinse slide thoroughly in 400 ml H$_2$O for 1 min followed by rinse in 400 ml propan-2-ol for 1 min and centrifuge slide in 50 ml centrifuge tube at 1,500 rpm for 5 min to dry. Store slide in dark, dust-free box until hybridisation (<1 h).

c) Purify Cy3/Cy5 Labelled DNA—Qiagen MinElute Purification

Combine Cy3 and Cy5 labelled DNA samples in single tube and add 500 µl Buffer PB.

Apply to MinElute column in collection tube and centrifuge at 13,000 rpm for 1 min.

Discard flow-through and place MinElute column back into same collection tube.

Add 500 µl Buffer PE to MinElute column and centrifuge at 13,000 rpm for 1 min.

Discard flow-through and place MinElute column back into same collection tube.

Add 250 µl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 µl H$_2$O to the centre of the membrane and allow to stand for 1 min.

Centrifuge at 13,000 rpm for 1 min.

EXAMPLE 5

Preparation of Cy3 or Cy5 Label cDNA from RNA a) Prepare one Cy3 and One Cy5 Labelled cDNA Sample per Microarray Slide Each sample:

| | |
|---|---|
| RNA | 2-10 µg |
| Random primers (3 µg/µl) | 1 µl |
| H$_2$O | to 11 µl |

Heat at 95° C. for 5 min, snap cool on ice and briefly centrifuge.

| | |
|---|---|
| Add to each: 5lFirst Strand Buffer | 5 µl |
| DTT (100 mM) | 2.5 µl |
| dNTPs (5 mM dA/G/TTP, 2 mM dCTP) | 2.3 µl |
| Cy3 OR Cy5 dCTP | 1.7 µl |
| SuperScript II (200 U/µl) | 2.5 µl |

Incubate at 25° C. in dark for 10 min followed by 42° C. in dark for 90 min.

b) Prehybridise Slide

Mix the prehybridisation solution in a Coplin jar and incubate at 65° C. during the labelling reaction to equilibriate.

Prehybridisation:

| | |
|---|---|
| 20 × SSC | 8.75 ml (3.5 × SSC) |
| 20% SDS | 250 µl (0.1% SDS) |
| BSA (100 mg/ml) | 5 ml (10 mg/ml) |
| H$_2$O | to 50 ml |

Incubate the microarray slide in the pre-heated prehybridisation solution at 65° C. for 20 min. Rinse slide thoroughly in 400 ml H$_2$O for 1 min followed by rinse in 400 ml propan-2-ol for 1 min and centrifuge slide in 50 ml centrifuge tube at 1500 rpm for 5 min to dry. Store slide in dark, dust-free box until hybridisation (<1 h).

c) Purify Cy3/Cy5 Labelled cDNA—Qiagen MinElute Purification

Combine Cy3 and Cy5 labelled DNA samples in single tube and add 250 µl Buffer PB.

Apply to MinElute column in collection tube and centrifuge at 13,000 rpm for 1 min.

Discard flow-through and place MinElute column back into same collection tube.

Add 500 µl Buffer PE to MinElute column and centrifuge at 13,000 rpm for 1 min.

Discard flow-through and place MinElute column back into same collection tube.

Add 250 µl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 µl H$_2$O to the centre of the membrane and allow to stand for 1 min.

Centrifuge at 13,000 rpm for 1 min.

EXAMPLE 6

Hybridise Slide with Cy3/Cy5 Labelled cDNA/DNA

Place the prehybridise microarray slide in the hybridisation cassette and add two 15 ml aliquots of H$_2$O to the wells in the cassette. Mix resuspended Cy3/Cy5 labelled cDNA/DNA sample with hybridisation solution.

| | | |
|---|---|---|
| Hybridisation: | Cy3/Cy5 labelled cDNA sample | 10.5 ml |
| | 20 × SSC | 3.2 ml (4 × SSC) |
| | 2% SDS | 2.3 ml (0.3% SDS) |

Heat hybridisation solution at 95° C. for 2 min. Do not snap cool on ice but allow to cool slightly and briefly centrifuge. Pipette the hybridisation solution onto the slide at the edge of the arrayed area avoiding bubble formation. Using forceps carefully drag the edge of a cover slip along the surface of the slide towards the arrayed area and into the hybridisation solution at the edge of the array. Carefully lower the cover slip down over the array avoiding any additional movement once in place. Seal the hybridisation cassette and submerge in a water bath at 60° C. for 16-20 h.

Wash slide.

Remove microarray slide from hybridisation cassette and initially wash slide carefully in staining trough of Wash A to remove cover slip. Once cover slip is displaced place slide(s) in slide rack and continue agitating in Wash A for a further 2 min.

| Wash A: | 20 × SSC | 20 ml (1 × SSC) |
|---|---|---|
| | 20% SDS | 1 ml (0.05% SDS) |
| | H$_2$O | to 400 ml |

Transfer slide(s) to a clean slide rack and agitate in first trough of Wash B for 2 min. Wash in second trough of Wash B with agitation for 2 min.

| Wash B (x2): | 20 × SSC | 1.2 ml(0.06 × SSC) |
|---|---|---|
| | H$_2$O | to 400 ml |

Place slide into a 50 ml centrifuge tube and centrifuge at 1500 rpm for 5 mins to dry slide, and then scan fluorescence using a ScanArray 3000 dual-laser confocal scanner and analyse data.

EXAMPLE 7

Preparation of the Arrays

PCR-amplified products are generated from *M. tuberculosis* genomic DNA using ORF-specific primers. Each gene of the genome is represented. These are spotted in a grid onto a standard glass microscope slide using a BioRobotics microgrid robot (MWG Biotech) at a resolution of >4000 spots/cm$^2$.

EXAMPLE 8

Scanning and Analysis of Data

The slides were scanned using an Affymetrix 428 scanner.

Dual fluorescence is used, allowing simultaneous detection of two cDNA samples. The output of the arrays is read using a confocal laser scanner (Affymetrix 428 scanner from MWG Biotech). More detailed information can be found web site www.sghms.ac.uk/depts/medmicro/bugs; Mujumdar, R. B. (1993) Bioconjugate Chemistry, 4 (2), pp. 105-111; Yu, H. (1994) Nucl. Acids Res. 22, pp. 3226-3232; and Zhu, Z. (1994) Nucl. Acids Res. 22, pp. 3418-3422.

The raw data were initially analysed in software known as ImaGene, which was supplied with the scanner. The scanned images were then transferred to another software package known as GeneSpring. This is a very powerful tool, which draws information from many databases allowing the complete analysis of the expression of each gene.

EXAMPLE 9

Delete One or More of the Genes from *M. tuberculosis* in Order to Attenuate its Virulence While Retaining Immunogenicity One or more genes that are identified may be disrupted using allelic exchange. In brief, the gene of interest is cloned with 1-2 kb of flanking DNA either side and is inactivated by deletion of part of the coding region and insertion of an antibiotic resistance marker, such as hygromycin.

The manipulated fragment is then transferred to a suitable suicide vector e.g. pPR23 and is transformed into the wild-type parent strain of *M. tuberculosis*. Mutants are recovered by selecting for antibiotic resistant strains. Genotypic analysis (Southern Blotting with a fragment specific to the gene of interest) is performed on the selected strains to confirm that the gene has been disrupted.

The mutant strain is then studied to determine the effect of the gene disruption on the phenotype. In order to use it as a vaccine candidate it would be necessary to demonstrated attenuated virulence. This can be done using either a guinea pig or mouse model of infection. Animals are infected with the mutant strain and the progression of disease is monitored by determining the bacterial load in different organs, in particular the lung and spleen, at specific time points post infection, typically up to 16 weeks.

Comparison is made to animals infected with the wild-type strain which should have a significantly higher bacterial load in the different organs. Long-term survival studies and histopathology can also be used to assess virulence and pathogenicity.

Once attenuated virulence has been established, protection and immunogenicity studies can be performed to assess the potential of the strain as a vaccine. Suitable references for allelic exchange and preparation of TB mutants are McKinney et al., 2000 and Pelicic et al., 1997, [1, 2].

EXAMPLE 10

Select One or More of the Genes Identifiable by the Present Invention, Which Encode Proteins that are Immunogenic, and Put Them into BCG or an Attenuated Strain of *M. tuberculosis* to Enhance its Overall Immunogenicity The gene of interest is amplified from the *M. tuberculosis* genome by PCR. The amplified product is purified and cloned into a plasmid (pMV306) that integrates site specifically into the mycobacterial genome at the attachment site (attB) for mycobacteriophage L5 [3].

BCG is transformed with the plasmid by electroporation, which involves damaging the cell envelope with high voltage electrical pulses, resulting in uptake of the DNA. The plasmid integrates into the BCG chromosome at the attB site generating stable recombinants. Recombinants are selected and are checked by PCR or Southern blotting to ensure that the gene has been integrated. The recombinant strain is then used for protection studies.

EXAMPLE 11

Use of Recombinant Carriers such as Attenuated *salmonella* and the Vaccinia Virus to Express and Present TB Genes One of the best examples of this type of approach is the use of Modified Vaccinia virus Ankara (MVA) [4]. The gene of interest is cloned into a vaccinia virus shuttle vector, e.g. pSC11. Baby Hamster Kidney (BHK) cells are then infected with wild-type MVA and are transfected with the recombinant shuttle vector. Recombinant virus is then selected using a suitable selection marker and viral plaques, selected and purified.

Recombinant virus is normally delivered as part of a prime-boost regime where animals are vaccinated initially with a DNA vaccine encoding the TB genes of interest under the control of a constitutive promoter. The immune response is boosted by administering recombinant MVA carrying the genes of interest to the animals at least 2 weeks later.

EXAMPLE 12

Sub-unit Vaccines Containing a Single Peptide/Protein or a Combination of Proteins To prepare sub-unit vaccines with one or more peptides or proteins it is first of all necessary to obtain a supply of protein or peptide to prepare the vaccine. Up to now, this has mainly been achieved in mycobacterial studies by purifying proteins of interest from TB culture. However, it is becoming more common to clone the gene of interest and produce a recombinant protein.

The coding sequence for the gene of interest is amplified by PCR with restriction sites inserted at the N terminus and C terminus to permit cloning in-frame into a protein expression vector such as pET-15b. The gene is inserted behind an inducible promoter such as lacZ. The vector is then transformed into E. coli which is grown in culture. The recombinant protein is over-expressed and is purified.

One of the common purification methods is to produce a recombinant protein with an N-terminal His-tag. The protein can then be purified on the basis of the affinity of the His-tag for metal ions on a Ni-NTA column after which the His-tag is cleaved. The purified protein is then administered to animals in a suitable adjuvant [5].

EXAMPLE 13

Plasmid DNA Vaccines Carrying One or More of the Identified Genes

DNA encoding a specific gene is amplified by PCR, purified and inserted into specialised vectors developed for vaccine development, such as pVAX1. These vectors contain promoter sequences, which direct strong expression of the introduced DNA (encoding candidate antigens) in eukaryotic cells (eg. CMV or SV40 promoters), and polyadenlyation signals (eg. SV40 or bovine growth hormone) to stabilise the mRNA transcript.

The vector is transformed into E. coli and transformants are selected using a marker, such as kanamycin resistance, encoded by the plasmid. The plasmid is then recovered from transformed colonies and is sequenced to check that the gene of interest is present and encoded properly without PCR generated mutations.

Large quantities of the plasmid is then produced in E. coli and the plasmid is recovered and purified using commercially available kits (e.g. Qiagen Endofree-plasmid preparation). The vaccine is then administered to animals for example by intramuscular injection in the presence or absence of an adjuvant.

EXAMPLE 14

Preparation of DNA Expression Vectors

DNA vaccines consist of a nucleic acid sequence of the present invention cloned into a bacterial plasmid. The plasmid vector pVAX1 is commonly used in the preparation of DNA vaccines. The vector is designed to facilitate high copy number replication in E. coli and high level transient expression of the peptide of interest in most mammalian cells (for details see manufacturers protocol for pVAX1 (catalog No. V260-20 www.invitrogen.com).

The vector contains the following elements:

Human cytomegalovirus immediate-early (CMV) promoter for high-level expression in a variety of mammalian cells T7 promoter/priming site to allow in vitro transcription in the sense orientation and sequencing through the insert Bovine growth hormone (BGH) polyadenylation signal for efficient transcription termination and polyadenylation of mRNA Kanamycin resistance gene for selection in E. coli A multiple cloning site pUC origin for high-copy number replication and growth in E. coli BGH reverse priming site to permit sequencing through the insert Vectors may be prepared by means of standard recombinant techniques which are known in the art, for example Sambrook et al. (1989). Key stages in preparing the vaccine are as follows:

The gene of interest is ligated into pVAX1 via one of the multiple cloning sites The ligation mixture is then transformed into a competent E. coli strain (e.g. TOP10) and LB plates containing 50 µg/ml kanamycin are used to select transformants.

Clones are selected and may be sequenced to confirm the presence and orientation of the gene of interest.

Once the presence of the gene has been verified, the vector can be used to transfect a mammalian cell line to check for protein expression. Methods for transfection are known in the art and include, for example, electroporation, calcium phosphate, and lipofection.

Once peptide expression has been confirmed, large quantities of the vector can be produced and purified from the appropriate cell host, e.g E. coli.

pVAX1 does not integrate into the host chromosome. All non-essential sequences have been removed to minimise the possibility of integration. When constructing a specific vector, a leader sequence may be included to direct secretion of the encoded protein when expressed inside the eukaryotic cell.

Other examples of vectors that have been used are V1Jns.tPA and pCMV4 (Lefevre et al., 2000 and Vordermeier et al., 2000).

Expression vectors may be used that integrate into the genome of the host, however, it is more common and more preferable to use a vector that does not integrate. The example provided, pVAX1, does not integrate. Integration would lead to the generation of a genetically modified host which raises other issues.

EXAMPLE 15

RNA Vaccine

As discussed on page 15 of U.S. Pat. No. 5,783,386, one approach is to introduce RNA directly into the host.

Thus, the vector construct (Example 14) may be used to generate RNA in vitro and the purified RNA then injected into the host. The RNA would then serve as a template for translation in the host cell. In this embodiment, integration would not normally occur.

Another option is to use an infectious agent such as the retroviral genome carrying RNA corresponding to the gene of interest. In this embodiment, integration into the host genome will occur.

Another option is the use of RNA replicon vaccines which can be derived from virus vectors such as Sindbis virus or Semliki Forest virus. These vaccines are self-replicating and self-limiting and may be administered as either RNA or DNA which is then transcribed into RNA replicons in vivo. The vector eventually causes lysis of the transfected cells thereby reducing concerns about integration into the host genome. Protocols for RNA vaccine construction are detailed in Cheng et al., (2001).

EXAMPLE 16

Diagnostic Assays Based on Assessing T Cell Responses

For a diagnostic assay based on assessing T cell responses it would be sufficient to obtain a sample of blood from the patient. Mononuclear cells (monocytes, T and B lymphocytes) can be separated from the blood using density gradients such as Ficoll gradients.

Both monocytes and B-lymphocytes are both able to present antigen, although less efficiently than professional antigen presenting cells (APCs) such as dendritic cells. The latter are more localised in lymphoid tissue.

The simplest approach would be to add antigen to the separated mononuclear cells and incubate for a week and then assess the amount of proliferation. If the individual had been exposed to the antigen previously through infection, then T-cell closes specific to the antigen should be more prevalent in the sample and should respond.

It is also possible to separate the different cellular populations should it be desired to control the ratio of T cells to APC's.

Another variation of this type of assay is to measure cytokine production by the responding lymphocytes as a measure of response. The ELISPOT assay described below in Example 17 is a suitable example of this variation.

EXAMPLE 17

Detection of Latent *Mycobacteria*

A major problem for the control of *tuberculosis* is the presence of a large reservoir of asymptomatic individuals infected with tubercle bacilli. Dormant bacilli are more resistant to front-line drugs.

The presence of latent *mycobacteria*-associated antigen may be detected indirectly either by detecting antigen specific antibody or T-cells in blood samples.

The following method is based on the method described in Lalvani et al. (2001) in which a secreted antigen, ESAT-6, was identified as being expressed by members of the *M. tuberculosis* complex but is absent from *M. Bovis* BCG vaccine strains and most environmental *mycobacteria*. 60-80% of patients also have a strong cellular immune response to ESAT-6. An ex-vivo ELISPOT assay was used to detect ESAT-6 specific T cells.

As applied to the present invention:

A 96 well plate is coated with cytokine (e.g. interferon-γ, IL-2) -specific antibody. Peripheral blood monocytes are then isolated from patient whole blood and are applied to the wells.

Antigen (ie. one of the peptides, fragments, derivatives or variants of the present invention) is added to stimulate specific T cells that may be present and the plates are incubated for 24 h. The antigen stimulates cytokine production which then binds to the specific antibody.

The plates are washed leaving a footprint where antigen-specific T cells were present.

A second antibody coupled with a suitable detection system, e.g. enzyme, is then added and the number of spots are enumerated after the appropriate substrate has been added.

The number of spots, each corresponding to a single antigen-specific T cell, is related to the total number of cells originally added.

The above Example also describes use of an antigen that may be used to distinguish TB infected individuals from BCG vaccinated individuals. This could be used in a more discriminative diagnostic assay.

EXAMPLE 18

In Vitro Model for Mycobacterial Persistence Under the Joint Conditions of Carbon-Starvation and Oxygen-Limitation (a Variation on Examples 1-8)

Materials and Methods

Studies were performed with *M. tuberculosis* strain H37Rv (NCTC cat. No. 7416)—a representative strain of *M. tuberculosis*. Stock cultures were grown on Middlebrook 7H10+OADC for 3 weeks at 37±2° C.

Culture Medium

Persistence cultures were established in Middlebrook 7H9 medium supplemented with Middlebrook ADC enrichment, 0.2% Tween 80 and 0.2% glycerol (see below). The medium was prepared with high quality water from a Millipore water purification system and filter sterilised by passage through a 0.1 μm pore size cellulose acetate membrane filter capsule (Sartorius Ltd). The pH was adjusted to 6.6 with concentrated hydrochloric acid.

Middlebrook 7H10+OADC agar was used to prepare inoculum cultures, enumerate the number of culturable bacteria in samples, and to assess culture purity.

Culture System

We used the culture system described in WO00/52139, operated as a batch fermenter, for this Example.

Culture experiments were performed in a one liter glass vessel operated at a working volume of 750 ml. The culture was agitated by a magnetic bar placed in the culture vessel coupled to a magnetic stirrer positioned beneath the vessel. Culture conditions were continuously monitored by an Anglicon Microlab Fermentation System (Brighton Systems, Newhaven), linked to sensor probes inserted into the culture through sealed ports in the top plate. The oxygen concentration was monitored with a galvanic oxygen electrode (Uniprobe, Cardiff) and was controlled through sparging the culture with a mixture of air and oxygen free-nitrogen. Temperature was monitored by an Anglicon temperature probe, and maintained by a heating pad positioned beneath the culture vessel. Culture pH was measured using an Ingold pH electrode (Mettler-Toledo, Leicester).

Inoculation and Culture

The vessel was filled with 750 ml of sterile culture medium and parameters were allowed to stabilise at 37° C.±2° C., pH 6.9±0.3 and a dissolved oxygen tension of approximately 70% air saturation. A dense inoculum suspension was prepared by resuspending Middlebrook agar cultures, grown at 37±2° C. for 3 week, in sterile deionised water. The inoculum was aseptically transferred to the culture vessel, to provide an initial culture turbidity of approximately 0.25 at 540 nm. The culture was maintained at 37° C. with an agitation rate of 500 to 750 rpm.

Figure 3:
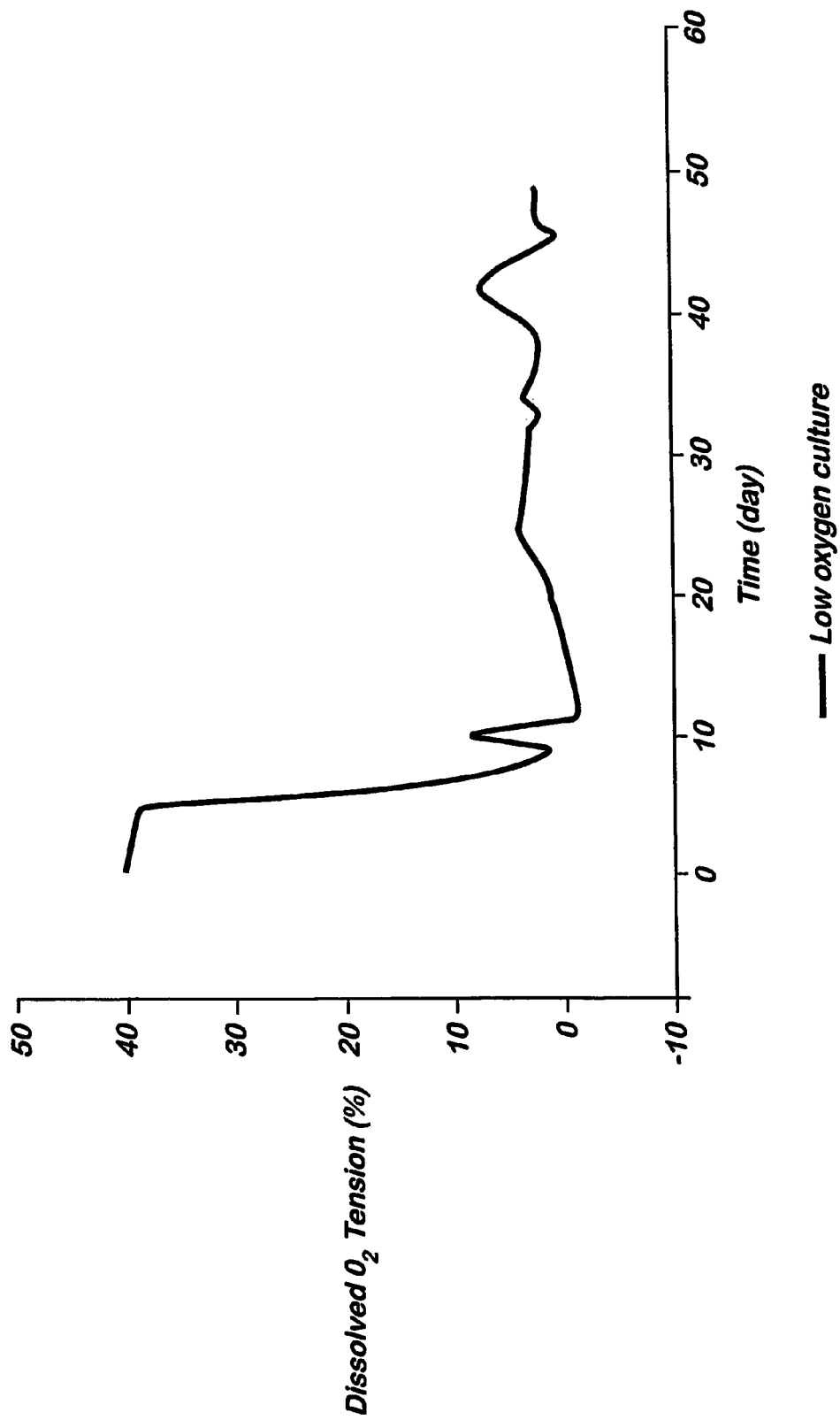

After inoculation, the dissolved oxygen tension (DOT) of the culture was maintained at approximately 40% air saturation at 37° C. until the culture had entered early exponential growth. The DOT was then lowered in increments down to 1% air saturation over a six day period (FIG. 3). The culture was then maintained at a DOT of 0-5% until 50 days after inoculation and samples were removed regularly to monitor growth and survival, nutrient utilisation and gene expression.

Growth and Survival

Bacterial growth and survival was assessed by determining the number of viable cells in the culture system at specific time points. This was achieved by preparing a decimal dilution series of the sample in sterile water and plating 100 (I aliquots onto Middlebrook 7H10+OADC plates. The plates were incubated at 37° C. for up to 4 weeks before enumerating the number of colonies formed.

Nutrient Utilisation

Glycerol is the primary carbon and energy source present in Middlebrook 7H9 medium with ADC, 0.2% Tween and Glycerol. The rate at which glycerol was utilised was determined using the Glycerol Determination Kit Cat. No. 148 270 Boehringer Mannheim.

Microarray Experiments

RNA was extracted from culture samples collected at different time points during the experiment. A fluorescently-labelled cDNA was then transcribed from each sample of RNA. The cDNA was labelled by the incorporation of either Cy3 or Cy5 labelled dCTP (Dyes are supplied by Amersham Pharmacia Biotech).

Whole *M. tuberculosis* genome arrays were prepared from *M. tuberculosis* genomic DNA using ORF-specific primers. PCR products corresponding to each ORF were spotted in a grid onto a standard glass microscope slide using a BioRobotics microgrid robot (MWG Biotech) at a resolution of >4000 spots/cm$^2$. Arrays were supplied by Dr P Butcher, St George's Hospital Medical School London.

In each microarray experiment a whole genome array was hybridised with labelled cDNA from one culture sample (Test sample). Each array was also hybridised with control DNA incorporating a different Cy dye and prepared from DNA extracted from *M. tuberculosis* strain H37Rv (control sample). Each array was scanned, using an Affymetrix 428 scanner, at two different wavelengths corresponding to the excitation maxima of each dye and the intensity of the emitted light was recorded. The raw data was processed by ImaGene software before performing comparative analysis using GeneSpring.

Results

Figure 2:
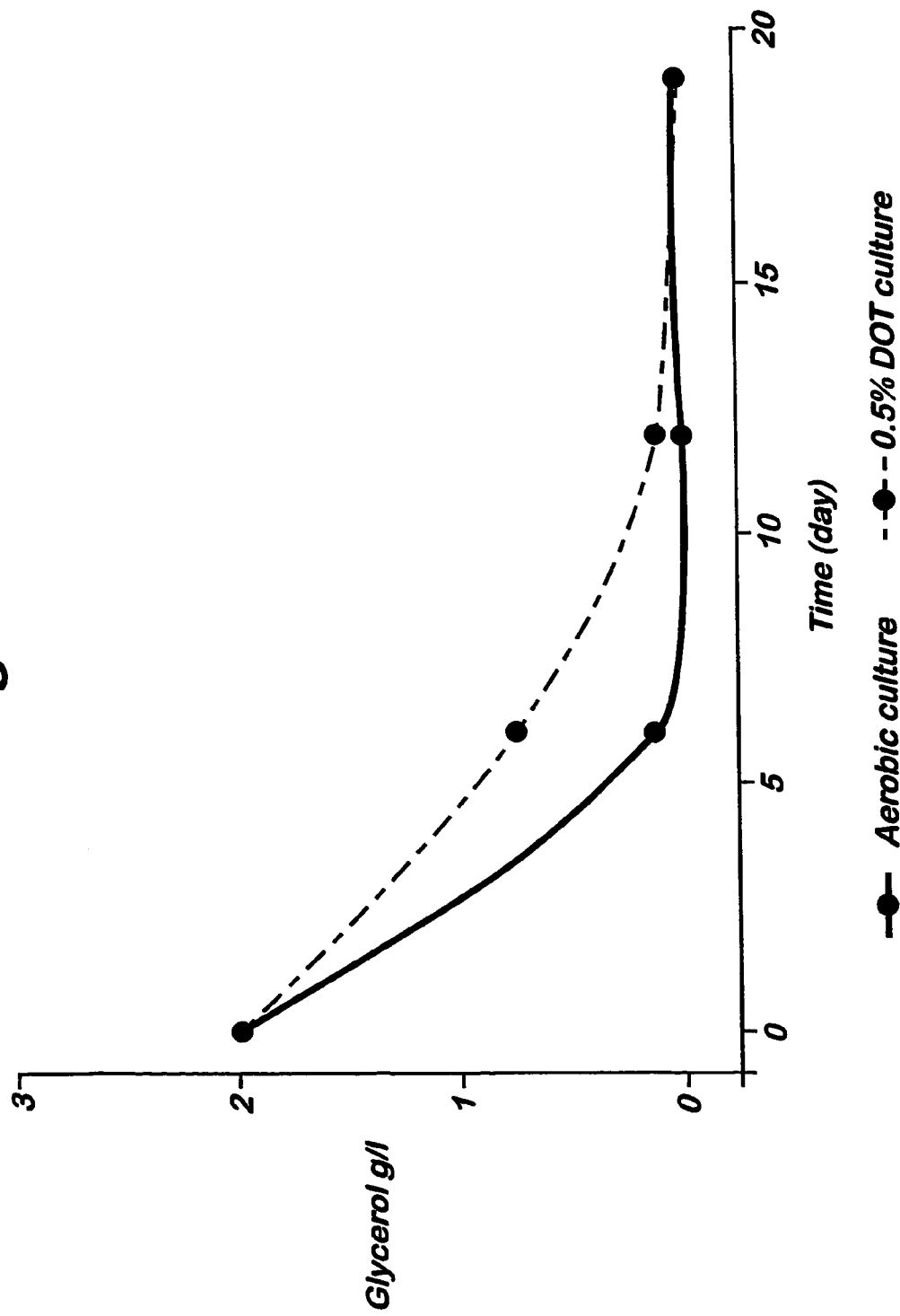
Figure 4:
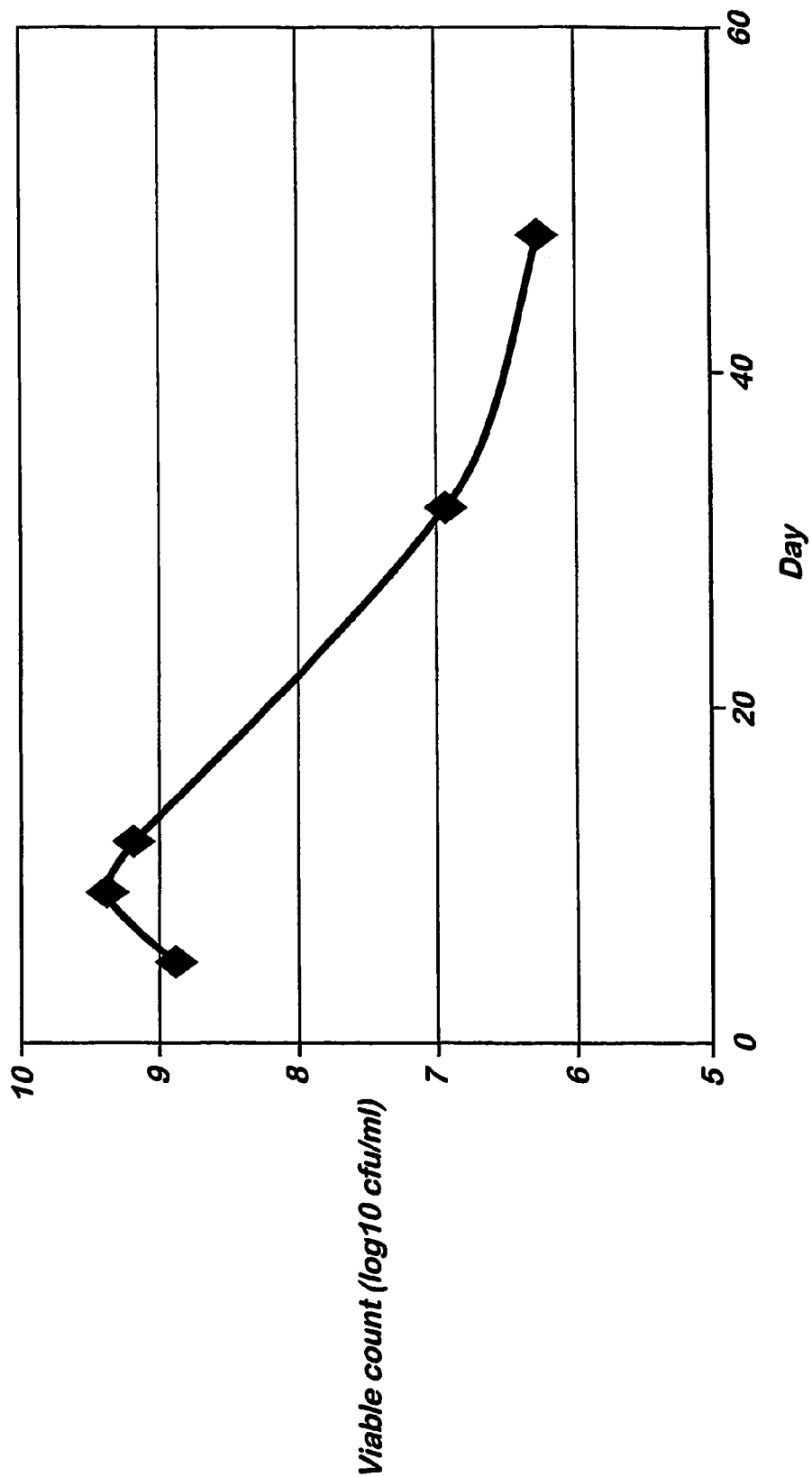

Analysis of viable count data indicated that the culture grew exponentially until 10 to 12 days post infection (FIG. 4). As the culture entered stationary phase, viability started to decline and continued to decline steadily over the duration of the study. After 40 days in stationary phase, approximately 0.1% of the culture was still culturable on Middlebrook agar. The rate of glycerol utilisation was slower than observed in the culture established under aerobic conditions, indicating that the metabolic activity of the low-oxygen culture was restricted by limited oxygen availability. Nevertheless, the principal carbon and energy source was depleted within 15 days after inoculation (FIG. 2).

Samples were collected for microarray analysis as outlined. The gene expression profiles for samples collected at day 5 and 50 were compared. Three arrays were prepared for each sample and the test data was normalised against the control data on each chip. The normalised data for each set of arrays was then averaged and the two data sets were compared. Those genes that were expressed 5-fold higher at day 5 relative to day 50 were selected. The gene list was compared with the list generated from the carbon starvation model (ie. Table 2), and a sub-list of genes which were only down-regulated under the combined conditions of carbon starvation and oxygen-limitation was generated (see Table 3).

Liquid medium formulation for persistence cultures—Middlebrook 7H9 medium supplemented with ADC, 0.2% Tween 80 and 0.2% Glycerol

| Composition per liter | |
|---|---|
| $Na_2HPO_4$ | 2.5 g |
| $KH_2PO_4$ | 1.0 g |
| Monosodium glutamate | 0.5 g |
| $(NH4)_2SO_4$ | 0.5 g |
| Sodium citrate | 0.1 g |
| $MgSO_4.7H_2O$ | 0.05 g |
| Ferric ammonium citrate | 0.04 g |
| $CuSO_4.5H_2O$ | 1.0 mg |
| Pyridoxine | 1.0 mg |
| $ZnSO_4.7H_2O$ | 1.0 mg |
| Biotin | 0.5 mg |
| $CaCl_2.2H_2O$ | 0.5 mg |
| Middlebrook ADC enrichment | 100 ml |
| Glycerol | 2.0 ml |
| Tween 80 | 2.0 ml |
| Middlebrook ADC enrichment - per | 100 ml |
| Bovine serum albumin | 5.0 g |
| Glucose | 2.0 g |
| Catalase | 3.0 mg |

Microarray Protocols

1. RNA Extraction from *M. tuberculosis* for Microarray Analysis

Materials and Methods

Trizol (Life Technologies)—formulation of phenol and guanidine thiocyanate.

GTC lysis solution containing: 5 M guanidine thiocyanate, 0.5% N-lauryl sarcosine, 25 mM tri-sodium citrate, 0.1 M 2-mercaptoethanol, and 0.5% Tween 80.

Chloroform
Isopropanol
3 M sodium acetate
70% Ethanol
microfuge
ribolyser
Sterile plasticware-Falcon tubes, screw capped eppendorfs, gilson tips—all RNase free
Glassware—baked at 160° C. for at least 16 hours Method Steps performed at Containment level 3; within a Class III microbiological safety cabinet.

Remove 10 or 20 ml of culture ($10^9$/ml) and immediately add this to 4 volumes of GTC lysis buffer in a plastic specimen pot. Seal the pot tightly.

Incubate the cells in GTC lysis buffer for 1 hour at room temperature. Surface decontaminate the plastic pot with 5% Hycolin for 5 minutes. Transfer the sample to the pass box and place it into a plastic carry tin with a sealable lid. Close the container securely and transport it to a non-toxic cabinet CL3 cabinet.

Equally distribute the lysis mixture between Falcon tubes. Place these tubes into centrifuge buckets and seal the buckets tightly. Surface-decontaminate the buckets for 5 minutes with 5% Hycolin. Then transfer them to the centrifuge (Baird and Tatlock Mark IV refrigerated bench-top centrifuge). Spin the tubes at 3,000 rpm for 30 minutes.

Return the unopened buckets to the cabinet. Remove the centrifuge tubes and pour the supernatant into a waste bottle for GTC lysis buffer.

Resuspend each pellet in 5 ml of Trizol (formulation of phenol and GTC cat No. 15596-026). The manufacturers guidelines recommend lysing cells by repetitive pipetting. Although this action alone will not lyse *M. tuberculosis*, it is important to completely resuspend the pellet in Trizol.

Transfer 1 ml of cells into each FastRNA tube and ribolyse them at power setting 6.5 for 45 seconds.

Leave the tubes to incubate at room temperature for 5 minutes.

Remove the aqueous layer from each tube and add this to 200 µl of chloroform in a screw-capped eppendorf tube. Shake each tube vigorously for about 15 seconds. Incubate for 2-3 minutes at room temperature.

Spin the tubes at 13,000 rpm for 15 minutes. Following centrifugation, the liquid separates into red phenol/chloroform phase, an interface, and a clear aqueous phase.

Carefully remove the aqueous phase and transfer it to fresh eppendorf tubes containing 500 µl of chloroform/isoamyl alcohol (24:1). Spin the tubes at 13,000 rpm for 15 minutes.

Transfer the aqueous phase to eppendorf tubes containing 50 µl of sodium acetate and 500 µl of isopropanol.

Surface decontaminate the eppendorf tubes with 5% Hycolin for 5 minutes. Remove the tubes from the CL3 laboratory and continue with the procedure in laboratory 157.

Steps performed at Containment level 2:

Precipitate the RNA at −70° C. for at least 30 minutes (optionally overnight).

Spin the precipitated RNA down at 13,000 rpm for 10 minutes. Remove the supernatant and wash the pellet in 70% ethanol. Repeat centrifugation.

Remove the 70% ethanol and air-dry the pellet. Dissolve the pellet in RNAse free water.

Freeze the RNA at −70° C. to store it.

2. Isolation of Genomic DNA from *Mycobacterium tuberculosis* Grown in Chemostat Culture. DNA Then Used to Generate Cy3 or Cy5 Labelled DNA for Use as a Control in Microarray Experiments Materials and Methods
Beads 0.5 mm in diameter
Bead beater
Bench top centrifuge
Platform rocker
Heat block
Falcon 50 ml centrifuge tubes
Sorvall RC-5C centrifuge
250 ml polypropylene centrifuge pots.
Screw capped eppendorf tubes
Pipettes 1 ml, 200 µl, 10 ml, 5 ml
Breaking buffer
50 mM Tris HCL pH 8.0
10 mM EDTA
100 mM NaCl Procedure Mechanical Disruption of Mtb Cells 150 ml of chemostat cells (O.D of 2.5 at 540 nm) are spun down at 15,000 rpm for 15 minutes in 250 ml polypropylene pots using centrifuge Sorvall RC-5C.

The supernatant is discarded.

Cells are re-suspended in 5 ml of breaking buffer in a 50 ml Falcon tube and centrifuged at 15,000 rpm for a further 15 minutes.

The supernatant is removed and additional breaking buffer is added at a volume of 5 ml. Beads are used to disrupt the cells. These are used at a quantity of 1 ml of beads for 1 ml of cells. Place the sample into the appropriate sized chamber. Place in the bead beater and secure the outer unit (containing ice) and process at the desired speed for 30 seconds.

Allow the beads to settle for 10 minutes and transfer cell lysate to a 50 ml Falcon centrifuge tube Wash beads with 2-5 ml of breaking buffer by pipetting washing buffer up and down over the beads.

Add this washing solution to the lysate in the falcon tube

Removal of Proteins and Cellular Components.

Add 0.1 volumes of 10% SDS and 0.01 volumes proteinase K.

Mix by inversion and heat at 55° C. in a heat block for 2-3 hours

The resulting mix should be homogenous and viscous. If it isn't then add more SDS to bring the concentration up to 0.2%

Add an equal volume of phenol/chloroform/Isoamyl alcohol in the ratio: 25/24/1.

Gently mix on a platform rocker until homogenous

Spin down at 3,000 rpm for 20 minutes

Remove the aqueous phase and place in a fresh tube

Extract the aqueous phase with an equal volume of chloroform to remove traces of cell debris and phenol. Chloroform extractions may need to be repeated to remove all the debris.

Precipitate the DNA with 0.3 M sodium acetate and an equal volume of isopropanol.

Spool as much DNA as you can with a glass rod

Wash the spooled DNA in 70% ethanol followed by 100% ethanol

Leave to air dry

Dissolve the DNA in sterile deionised water (500 µl)

Allow DNA to dissolve at 4° C. for approximately 16 hours.

Add RNase 1 (500 U) to the dissolved DNA

Incubate for 1 hour at 37° C.

Re-extract with an equal volume of phenol/chloroform followed by a chloroform extraction and precipitate as before Spin down the DNA at 13,000 rpm Remove the supernatant and wash the pellet in 70% ethanol Air dry Dissolve in 200-500 µl of sterile water.

3. Preparation of Cy3 or Cy5 Labelled DNA from DNA a) Prepare One Cy3 or One Cy5 Labelled DNA Sample per Microarray Slide.

| | |
|---|---|
| Each sample: DNA | 2-5 µg |
| Random primers (3 µg/µl) | 1 µl |
| H₂O | to 41.5 µl |

Heat at 95° C. for 5 min, snap cool on ice and briefly centrifuge.

| | |
|---|---|
| Add to each: 10 * REact 2 buffer | 5 µl |
| dNTPs (5 mM dA/G/TTP, 2 mM dCTP) | 1 µl |
| Cy3 OR Cy5 dCTP | 1.5 µl |
| Klenow (5 U/µl) | 1 µl |

Incubate at 37° C. in dark for 90 min.

b) Prehybridise Slide

Mix the prehybridisation solution in a Coplin jar and incubate at 65° C. during the labelling reaction to equilibriate.

| Prehybridisation: 20 * SSC | 8.75 ml(3.5 * SSC) |
|---|---|
| 20% SDS | 250 µl(0.1% SDS) |
| BSA (100 mg/ml) | 5 ml(10 mg/ml) |
| $H_2O$ | to 50 ml |

Incubate the microarray slide in the pre-heated prehybridisation solution at 65° C. for min. Rinse slide thoroughly in 400 ml $H_2O$ for 1 min followed by rinse in 400 ml propan-2-ol for 1 min and centrifuge slide in 50 ml centrifuge tube at 1,500 rpm for 5 min to dry. Store slide in dark, dust-free box until hybridisation (<1 h).

c) Purify Cy3/Cy5 Labelled DNA—Qiagen MinElute Purification

Combine Cy3 and Cy5 labelled DNA samples in single tube and add 500 µl Buffer PB.

Apply to MinElute column in collection tube and centrifuge at 13,000 rpm for 1 min.

Discard flow-through and place MinElute column back into same collection tube.

Add 500 µl Buffer PE to MinElute column and centrifuge at 13,000 rpm for 1 min.

Discard flow-through and place MinElute column back into same collection tube.

Add 250 µl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 µl $H_2O$ to the centre of the membrane and allow to stand for 1 min.

Centrifuge at 13,000 rpm for 1 min.

4. Preparation of Cy3 or Cy5 Label cDNA from RNA.

a) Prepare One Cy3 and One Cy5 Labelled cDNA Sample per Microarray Slide.

| Each sample: RNA | 2-10 µg |
|---|---|
| Random primers (3 µg/µl) | 1 µl |
| $H_2O$ | to 11 µl |

Heat at 95° C. for 5 min, snap cool on ice and briefly centrifuge.

| Add to each: 5 * First Strand Buffer | 5 µl |
|---|---|
| DTT (100 mM) | 2.5 µl |
| dNTPs (5 mM dA/G/TTP, 2 mM dCTP) | 2.3 µl |
| Cy3 OR Cy5 dCTP | 1.7 µl |
| SuperScript II (200 U/µl) | 2.5 µl |

Incubate at 25° C. in dark for 10 min followed by 42° C. in dark for 90 min.

b) Prehybridise Slide

Mix the prehybridisation solution in a Coplin jar and incubate at 65° C. during the labelling reaction to equilibriate.

Prehybridisation:

| 20 * SSC | 8.75 ml (3.5 * SSC) |
|---|---|
| 20% SDS | 250 µl (0.1% SDS) |
| BSA (100 mg/ml) | 5 ml (10 mg/ml) |
| $H_2O$ | to 50 ml |

Incubate the microarray slide in the pre-heated prehybridisation solution at 65° C. for 20 min. Rinse slide thoroughly in 400 ml $H_2O$ for 1 min followed by rinse in 400 ml propan-2-ol for 1 min and centrifuge slide in 50 ml centrifuge tube at 1500 rpm for 5 min to dry. Store slide in dark, dust-free box until hybridisation (<1 h).

c) Purify Cy3/Cy5 Labelled cDNA—Qiagen MinElute Purification

Combine Cy3 and Cy5 labelled DNA samples in single tube and add 250 µl Buffer PB.

Apply to MinElute column in collection tube and centrifuge at 13,000 rpm for 1 min.

Discard flow-through and place MinElute column back into same collection tube.

Add 500 µl Buffer PE to MinElute column and centrifuge at 13,000 rpm for 1 min.

Discard flow-through and place MinElute column back into same collection tube.

Add 250 µl Buffer PE to MinElute column and centrifuge at 13,000 rpm for 1 min.

Discard flow-through and place MinElute column back into same collection tube.

Centrifuge at 13,000 rpm for an additional 1 min to remove residual ethanol.

Place the MinElute column into a fresh 1.5 ml tube.

Add 10.5 µl $H_2O$ to the centre of the membrane and allow to stand for 1 min.

Centrifuge at 13,000 rpm for 1 min.

5. Hybridise Slide with Cy3/Cy5 Labelled cDNA/DNA

Place the prehybridise microarray slide in the hybridisation cassette and add two 15 µl aliquots of $H_2O$ to the wells in the cassette. Mix resuspended Cy3/Cy5 labelled cDNA sample with hybridisation solution.

| Hybridisation: | Cy3/Cy5 labelled cDNA sample | 10.5 µl |
|---|---|---|
| | 20 × SSC | 3.2 µl (4 × SSC) |
| | 2% SDS | 2.3 µl (0.3% SDS) |

Heat hybridisation solution at 95° C. for 2 min. Do NOT snap cool on ice but allow to cool slightly and briefly centrifuge. Pipette the hybridisation solution onto the slide at the edge of the arrayed area avoiding bubble formation. Using forceps carefully drag the edge of a cover slip along the surface of the slide towards the arrayed area and into the hybridisation solution at the edge of the array. Carefully lower the cover slip down over the array avoiding any additional movement once in place. Seal the hybridisation cassette and submerge in a water bath at 65° C. for 16-20 hours.

Wash Slide

Remove microarray slide from hybridisation cassette and initially wash slide carefully in staining trough of Wash A preheated to 65° C. to remove cover slip. Once cover slip is displaced place slide(s) in slide rack and continue agitating in Wash A for a further 2 min.

| Wash A: | 20 × SSC | 20 ml (1 × SSC) |
| | 20% SDS | 1 ml (0.05% SDS) |
| | H₂O | to 400 ml |

Transfer slide(s) to a clean slide rack and agitate in first trough of Wash B for 2 min. Wash in second trough of Wash B with agitation for 2 min.

| Wash B (x2): | 20 × SSC | 1.2 ml (0.06 × SSC) |
| | H₂O | to 400 ml |

Place slide into a 50 ml centrifuge tube and centrifuge at 1500 rpm for 5 mins to dry slide and then scan fluorescence.

The genes identified in accordance with Example 18 are listed in Table 3. Those genes overlapping with Table 2 have been omitted from Table 3. The coding sequences for these genes (nucleic acid sequences are given from the transcription start site to the stop codon) and corresponding amino acid sequences are listed in the accompanying Sequence Listing starting from SEQ ID NO. 21 et seq (amino acid sequences are followed immediately by corresponding coding sequences for each gene).

TABLE 3

Genes down-regulated during survival under the combined conditions of carbon starvation and oxygen limitation (excluding those genes which are down-regulated in response to the single stimulus of carbon starvation - Table 2)

| Genes | Fold- | Assigned function | SEQ ID NO: |
|---|---|---|---|
| Rv0511; cysG (9O15) | 5.7679 | Uroporphyrin-III C-methyltransferase HEMD (uroporphyrinogen III methylase) (urogen III methylase) (SUMT) (urogen III methylase) | 21;22 |
| Rv1079; metB (5G11) | 6.1459 | Cystathionine gamma-synthase METB (CGS) (O-succinylhomoserine [Thiol]-lyase)23;24 | 23;24 |
| Rv0206c; mmpL3 (1K8) | 5.3012 | Transmembrane transport protein MMPL3 | 25;26 |
| Rv2942; mmpL7 (2K8) | 5.0236 | Transmembrane transport protein MMPL7 | 27;28 |
| Rv0055; rpsR (1G7) | 5.0654 | 30S ribosomal protein S18-1 RPSR1 | 29;30 |
| Rv0144; (8P3) | 8.3578 | Transcriptional regulatory protein | 31;32 |
| Rv0198c; (1K7) | 5.4541 | Zinc metalloprotease | 33;34 |
| Rv0361; (2L23) | 5.8502 | Membrane protein | 35;36 |
| Rv0635; (4L23) | 7.212 | | 37;38 |
| Rv0805; (3O23) | 6.3055 | | 39;40 |
| Rv1871c; (10O15) | 5.495 | | 41;42 |
| Rv3599c; (11C1) | 19.6683 | | 43;44 |
| Rv3661; (2C23) | 5.2733 | | 45;46 |

The invention claimed is:

1. An isolated *M. tuberculosis* peptide, wherein said peptide is selected from the group consisting of:
   (i) (a) SEQ ID NO: 1, 5, 11, 15, 21, 25, 27, 31, 33, 35, 37, 41, 43, or 45; or a fusion protein comprising said SEQ ID NO;

(b) a fragment of SEQ ID NO: 1, 5, 11, 15, 21, 25, 27, 31, 33, 35, 37, 41, 43, or 45, wherein said fragment has at least 35 amino acid residues; or a fusion protein comprising said fragment; wherein said fragment has a common antigenic cross-reactivity to SEQ ID NO: 1, 5, 11, 15, 21, 25, 27, 31, 33, 35, 37, 41, 43, or 45; or (c) a variant of SEQ ID NO: 1, 5, 11, 15, 21, 25, 27, 31, 33, 35, 37, 41, 43, or 45 wherein the full-length amino acid sequence of said variant has at least 70% amino acid homology with the full-length amino acid sequence of SEQ ID NO: 1, 5, 11, 15, 21, 25, 27, 31, 33, 35, 37, 41, 43, or 45; or a fusion protein comprising said variant; wherein said variant has a common antigenic cross-reactivity to SEQ ID NO: 1, 5, 11, 15, 21, 25, 27, 31, 33, 35, 37, 41, 43, or 45;

(ii) (a) SEQ ID NO: 7 or 17, or a fusion protein comprising SEQ ID NO: 7 or 17; or (b) a variant of SEQ ID NO: 7 or 17, wherein the full-length amino acid sequence of said variant has at least 70% amino acid homology with the full-length amino acid sequence of SEQ ID NO: 7 or 17; or a fusion protein comprising said variant; wherein said variant has a common antigenic cross-reactivity to SEQ ID NO: 7 or 17;

(iii) (a) SEQ ID NO: 3; or a fusion protein comprising SEQ ID NO: 3; or (b) a variant of SEQ ID NO: 3, wherein the full-length amino acid sequence of said variant has at least 80% amino acid homology with the full-length amino acid sequence of SEQ ID NO: 3; or a fusion protein comprising said variant; wherein said variant has a common antigenic cross-reactivity to SEQ ID NO: 3;

(iv) (a) SEQ ID NO: 23 or 39 or a fusion protein comprising SEQ ID NO: 23 or 29;

(b) a fragment of SEQ ID NO: 23 or 39, wherein said fragment has at least 35 amino acid residues; or a fusion protein comprising said fragment; wherein said fragment has a common antigenic cross-reactivity to SEQ ID NO: 23 or 39; or (c) a variant of SEQ ID NO: 23 or 39, wherein the full-length amino acid sequence of said variant has at least 90% amino acid homology with the full-length amino acid sequence of SEQ ID NO: 23 or 39; or a fusion protein comprising said variant; wherein said variant has a common antigenic cross-reactivity to SEQ ID NO: 23 or 39; and (v) SEQ ID NO: 19, or a fusion protein comprising SEQ ID NO: 19;

wherein the peptide is encoded by an *M. tuberculosis* gene the expression of which is down-regulated during a stationary phase culture of *M. tuberculosis* under nutrient-starving culture conditions when compared with an exponential phase culture of *M. tuberculosis* under culture conditions that are not nutrient-starving and that support exponential growth of said *M. tuberculosis*.

2. A diagnostic kit for identifying a mycobacterial infection, comprising an isolated *M. tuberculosis* peptide, wherein the peptide is selected from the group consisting of:

(i) (a) SEQ ID NO: 1, 5, 11, 15, 21, 25, 27, 31, 33, 35, 37, 41, 43, or 45; or a fusion protein comprising said SEQ ID NO;

(b) a fragment of SEQ ID NO: 1, 5, 11, 15, 21, 25, 27, 31, 33, 35, 37, 41, 43, or 45, wherein said fragment has at least 35 amino acid residues; or a fusion protein comprising said fragment; wherein said fragment has a common antigenic cross-reactivity to SEQ ID NO: 1, 5, 11, 15, 21, 25, 27, 31, 33, 35, 37, 41, 43, or 45; or (c) a variant of SEQ ID NO: 1, 5, 11, 15, 21, 25, 27, 31, 33, 35, 37, 41, 43, or 45 wherein the full-length amino acid sequence of said variant has at least 70% amino acid homology with the full-length amino acid sequence of SEQ ID NO: 1, 5, 11, 15, 21, 25, 27, 31, 33, 35, 37, 41, 43, or 45; or a fusion protein comprising said variant; wherein said variant has a common antigenic cross-reactivity to SEQ. ID NO: 1, 5, 11, 15, 21, 25, 27, 31, 33, 35, 37, 41, 43, or 45;

(ii) (a) SEQ ID NO: 7 or 17, or a fusion protein comprising SEQ ID NO: 7 or 17; or (b) a variant of SEQ ID NO: 7 or 17, wherein the full-length amino acid sequence of said variant has at least 70% amino acid homology with the full-length amino acid sequence of SEQ ID NO: 7 or 17; or a fusion protein comprising said variant; wherein said variant has a common antigenic cross-reactivity to SEQ ID NO: 7 or 17;

(iii) (a) SEQ ID NO: 3; or a fusion protein comprising SEQ ID NO: 3; or (b) a variant of SEQ ID NO: 3, wherein the full-length amino acid sequence of said variant has at least 80% amino acid homology with the full-length amino acid sequence of SEQ ID NO: 3; or a fusion protein comprising said variant; wherein said variant has a common antigenic cross-reactivity to SEQ ID NO: 3;

(iv) (a) SEQ ID NO: 23 or 39 or a fusion protein comprising SEQ ID NO: 23 or 29;

(b) a fragment of SEQ ID NO: 23 or 39, wherein said fragment has at least 35 amino acid residues; or a fusion protein comprising said fragment; wherein said fragment has a common antigenic cross-reactivity to SEQ ID NO: 23 or 39; or (c) a variant of SEQ ID NO: 23 or 39, wherein the full-length amino acid sequence of said variant has at least 90% amino acid homology with the full-length amino acid sequence of SEQ ID NO: 23 or 39; or a fusion protein comprising said variant; wherein said variant has a common antigenic cross-reactivity to SEQ ID NO: 23 or 39; and (v) SEQ ID NO: 19, or a fusion protein comprising SEQ ID NO: 19;

wherein the peptide is encoded by an *M. tuberculosis* gene the expression of which is down-regulated during a stationary phase culture of *M. tuberculosis* under nutrient-starving culture conditions when compared with an exponential phase culture of *M. tuberculosis* under culture conditions that are not nutrient-starving and that support exponential growth of said *M. tuberculosis* and a buffer; wherein said kit is packaged in one or more suitable containers.

3. A method of diagnosing a mycobacterial infection, comprising the steps of (a) incubating a biological sample with an isolated *M. tuberculosis* peptide selected from the group consisting of:

(i) (a) SEQ ID NO: 1, 5, 11, 15, 21, 25, 27, 31, 33, 35, 37, 41, 43, or 45; or a fusion protein comprising said SEQ ID NO;

(b) a fragment of SEQ ID NO: 1, 5, 11, 15, 21, 25, 27, 31, 33, 35, 37, 41, 43, or 45, wherein said fragment has at least 35 amino acid residues; or a fusion protein comprising said fragment; wherein said fragment has a common antigenic cross-reactivity to SEQ ID NO: 1, 5, 11, 15, 21, 25, 27, 31, 33, 35, 37, 41, 43, or 45; or (c) a variant of SEQ ID NO: 1, 5, 11, 15, 21, 25, 27, 31, 33, 35, 37, 41, 43, or 45 wherein the full-length amino acid sequence of said variant has at least 70% amino acid homology with the full-length amino acid sequence of SEQ ID NO: 1, 5, 11, 15, 21, 25, 27, 31, 33, 35, 37, 41, 43, or 45; or a fusion protein comprising said variant; wherein said variant has a common antigenic cross-reactivity to SEQ. ID NO: 1, 5, 11, 15, 21, 25, 27, 31, 33, 35, 37, 41, 43, or 45;

(ii) (a) SEQ ID NO: 7 or 17, or a fusion protein comprising SEQ ID NO: 7 or 17; or (b) a variant of SEQ ID NO: 7 or 17, wherein the full-length amino acid sequence of said variant has at least 70% amino acid homology with the full-length amino acid sequence of SEQ ID NO: 7 or 17; or a fusion protein comprising said variant; wherein said variant has a common antigenic cross-reactivity to SEQ ID NO: 7 or 17;

(iii) (a) SEQ ID NO: 3; or a fusion protein comprising SEQ ID NO: 3; or (b) a variant of SEQ ID NO: 3, wherein the full-length amino acid sequence of said variant has at least 80% amino acid homology with the full-length amino acid sequence of SEQ ID NO: 3; or a fusion protein comprising said variant; wherein said variant has a common antigenic cross-reactivity to SEQ ID NO: 3;

(iv) (a) SEQ ID NO: 23 or 39 or a fusion protein comprising SEQ ID NO: 23 or 29;

(b) a fragment of SEQ ID NO: 23 or 39, wherein said fragment has at least 35 amino acid residues; or a fusion protein comprising said fragment; wherein said fragment has a common antigenic cross-reactivity to SEQ ID NO: 23 or 39; or (c) a variant of SEQ ID NO: 23 or 39, wherein the full-length amino acid sequence of said variant has at least 90% amino acid homology with the full-length amino acid sequence of SEQ ID NO: 23 or 39; or a fusion protein comprising said variant; wherein said variant has a common antigenic cross-reactivity to SEQ ID NO: 23 or 39; and (v) SEQ ID NO: 19, or a fusion protein comprising SEQ ID NO: 19; wherein the peptide is encoded by an *M. tuberculosis* gene the expression of which is down-regulated during a stationary phase culture of *M. tuberculosis* under nutrient-starving culture conditions when compared with an exponential phase culture of *M. tuberculosis* under culture conditions that are not nutrient-starving and that support exponential growth of said *M. tuberculosis*, and (b) detecting antibodies to mycobacteria, and thereby mycobacterial infection.

4. The peptide of claim 1, wherein said peptide is selected from the group consisting of:

(i) (a) SEQ ID NO: 33 or a fusion protein comprising SEQ ID NO: 33;

(b) a fragment of SEQ ID NO: 33, wherein said fragment has at least 35 amino acid residues; or a fusion protein comprising said fragment; wherein said fragment has a common antigenic cross-reactivity to SEQ ID NO: 33; or (c) a variant of SEQ ID NO: 33, wherein the full-length amino acid sequence of said variant has at least 70% amino acid homology with the full-length amino acid sequence of SEQ ID NO: 33; or a fusion protein comprising said variant; wherein said variant has a common antigenic cross-reactivity to SEQ ID NO: 33;

(iii) (a) SEQ ID NO: 3; or a fusion protein comprising SEQ ID NO: 3; or (b) a variant of SEQ ID NO: 3, wherein the full-length amino acid sequence of said variant has at least 80% amino acid homology with the full-length amino acid sequence of SEQ ID NO: 3; or a fusion protein comprising said variant; wherein said variant has a common antigenic cross-reactivity to SEQ ID NO: 3.

5. The diagnostic kit of claim 2, wherein the peptide is selected from the group consisting of:

(i) (a) SEQ ID NO: 33; or a fusion protein comprising SEQ ID NO: 33;

(b) a fragment of SEQ ID NO: 33, wherein said fragment has at least 35 amino acid residues; or a fusion protein comprising said fragment; wherein said fragment has a common antigenic cross-reactivity to SEQ ID NO: 33; or (c) a variant of SEQ ID NO: 33, wherein the full-length amino acid sequence of said variant has at least 70% amino acid homology with the full-length amino acid sequence of SEQ ID NO: 33; or a fusion protein comprising said variant; wherein said variant has a common antigenic cross-reactivity to SEQ. ID NO: 33;

(iii) (a) SEQ ID NO: 3; or a fusion protein comprising SEQ ID NO: 3; or (b) a variant of SEQ ID NO: 3, wherein the full-length amino acid sequence of said variant has at least 80% amino acid homology with the full-length amino acid sequence of SEQ ID NO: 3; or a fusion protein comprising said variant; wherein said variant has a common antigenic cross-reactivity to SEQ ID NO: 3.

6. The method of claim 3, wherein said peptide is selected from the group consisting of:
- (i) (a) SEQ ID NO: 33; or a fusion protein comprising SEQ ID NO: 33;
  - (b) a fragment of SEQ ID NO: 33, wherein said fragment has at least 35 amino acid residues; or a fusion protein comprising said fragment; wherein said fragment has a common antigenic cross-reactivity to SEQ ID NO: 33; or
  - (c) a variant of SEQ ID NO: 33, wherein the full-length amino acid sequence of said variant has at least 70% amino acid homology with the full-length amino acid sequence of SEQ ID NO: 33; or a fusion protein comprising said variant; wherein said variant has a common antigenic cross-reactivity to SEQ. ID NO: 33;
- (iii) (a) SEQ ID NO: 3; or a fusion protein comprising SEQ ID NO: 3; or
  - (b) a variant of SEQ ID NO: 3, wherein the full-length amino acid sequence of said variant has at least 80% amino acid homology with the full-length amino acid sequence of SEQ ID NO: 3; or a fusion protein comprising said variant; wherein said variant has a common antigenic cross-reactivity to SEQ ID NO: 3.

* * * * *

UNITED STATES PATENT AND TRADEMARK OFFICE
CERTIFICATE OF CORRECTION

| | | |
|---|---|---|
| PATENT NO. | : 7,811,588 B2 | |
| APPLICATION NO. | : 10/493462 | |
| DATED | : October 12, 2010 | |
| INVENTOR(S) | : Brian William James | |

It is certified that error appears in the above-identified patent and that said Letters Patent is hereby corrected as shown below:

On the Front Page:

Item (56) Other Publications,
Please delete "Nutter" and insert --Hutter--.

Page 2:
Col. 2, line 2, please insert --)-- after "2002".

Signed and Sealed this

Thirtieth Day of August, 2011

David J. Kappos
*Director of the United States Patent and Trademark Office*